United States Patent
Whitcomb

(10) Patent No.: US 6,653,081 B2
(45) Date of Patent: Nov. 25, 2003

(54) METHODS FOR MONITORING ANTIRETROVIRAL THERAPY AND GUIDING THERAPEUTIC DECISION IN THE TREATMENT OF HIV/AIDS

(75) Inventor: Jeannette Whitcomb, San Mateo, CA (US)

(73) Assignee: ViroLogic, Inc., South San Francisco, CA (US)

( * ) Notice: Subject to any disclaimer, the term of this patent is extended or adjusted under 35 U.S.C. 154(b) by 0 days.

(21) Appl. No.: 09/881,033

(22) Filed: Jun. 12, 2001

(65) Prior Publication Data

US 2002/0037500 A1 Mar. 28, 2002

Related U.S. Application Data

(60) Provisional application No. 60/211,245, filed on Jun. 12, 2000.

(51) Int. Cl.[7] .................... C12Q 1/68; C12P 19/34; C12N 15/01; C12N 15/09; C12N 15/48
(52) U.S. Cl. ............... 435/6; 435/4; 435/5; 435/8; 435/91.1; 435/91.2; 435/69.1; 435/235.1; 435/238; 435/441; 435/442; 424/188.1
(58) Field of Search ...................... 435/235.1, 238, 435/441, 442, 91.1, 91.2, 69.1, 4, 5, 6, 8; 424/188.1

(56) References Cited

U.S. PATENT DOCUMENTS 5,917,033 A 6/1999 Modak et al.

OTHER PUBLICATIONS

Boyer et al. J. Virol. 1993, vol. 67, pp. 2412–2420.*
Hammond et al. Mutations in Retroviral Genes Associated with Drug Resistance 1998, pp. 36–98.*
Petropoulos et al. Anti. Agents and Chemoth. 2000, vol. 44, pp. 920–928.*

* cited by examiner

Primary Examiner—James Housel
Assistant Examiner—Bao Qun Li
(74) Attorney, Agent, or Firm—Pennie & Edmonds LLP

(57) ABSTRACT

This invention relates to antiviral drug susceptibility and resistance tests to be used in identifying effective drug regimens for the treatment of human immunodeficiency virus (HIV) infection and acquired immunodeficiency syndrome (AIDS) and further relates to the means and methods of monitoring the clinical progression of HIV infection and its response to antiretroviral therapy, particularly nucleoside reverse transcriptase inhibitor therapy using phenotypic susceptibility assays or genotypic assays.

12 Claims, 21 Drawing Sheets

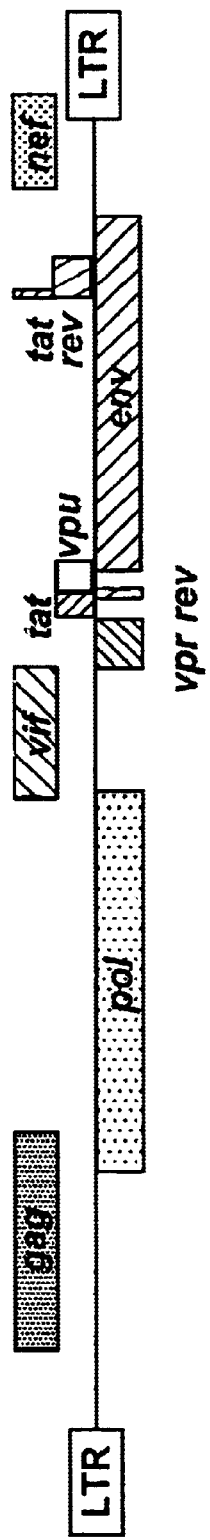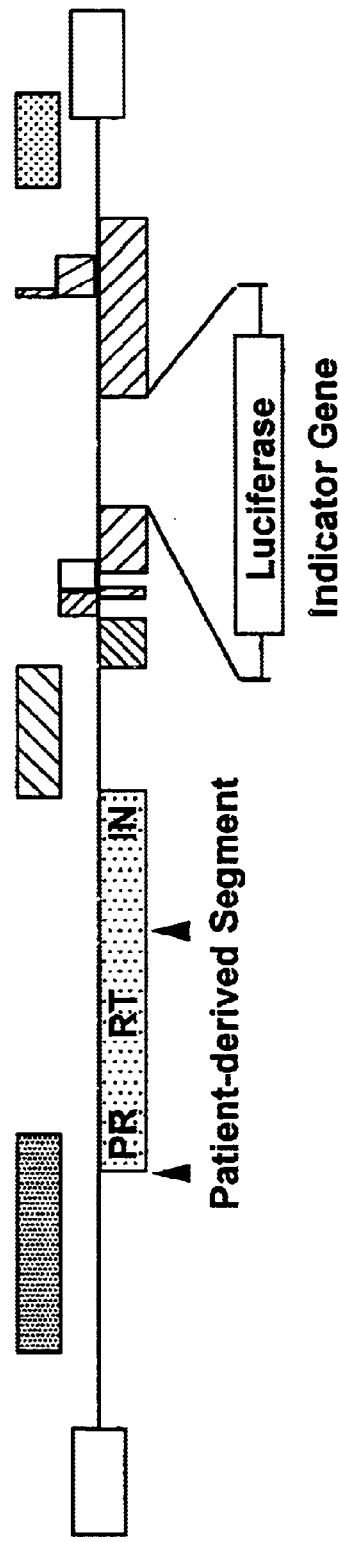
Fig. 1

Table of patient viruses containing M230L mutations (example 3, 4, and 5)

| ACCESSION # | Date of Draw | Mutations Observed in Reverse Transcriptase | DLV | EFV | NVP |
|---|---|---|---|---|---|
| ARG-014 (Example 3) | | | | | |
| 98-773 | 11/18/97 | M41L, L74I, M184V, L210W, R211K, T215Y, L228R, T296S | 0.3 | 0.3 | 0.4 |
| 98-1046 | 1/13/98 | M41L, L74I, <u>Y181C</u>, M184V, H198L, L210W, R211K, T215Y, L228R, <u>M230L</u>, T296S | >250 | 5.3 | >600 |
| 98-887 | 3/17/98 | M41L, L74I, <u>Y181C</u>, M184V, L210W, R211K, T215Y, L228R, <u>M230L</u>, T296S | 160.9 | 6.7 | >600 |
| CCTG-2165 (Example 4) | | | | | |
| 99-2-009089 | 11/10/99 | K49R, Q102K, K122E, E169D, I178M, M184V, I195T, T200A, R211K, V245M, D250E, K275Q, V276I, R277K, T286A, P294T | 0.9 | 0.2 | 1.1 |
| 00-2-010835 | 1/26/00 | K49R, Q102K, <u>K103N</u>, K122E, E169D, I178M, M184V, I195T, T200A, R211K, <u>M230L</u>, V245M, D250E, K275Q, V276I, R277K, T286A, P294T | >250 | 269.7 | >600 |
| CCTG-1025 (Example 5) | | | | | |
| AA2919 | 3/30/99 | D67D/N, D86E, Q102K, V118I, K122P, A158S, C162S, Q174H, D177E, R211K, F214L, T215Y, A272P, K275N, V276I/A/I/T, R277K, Q278H, K281R, T286A, V293I | 0.4 | 0.5 | 0.7 |
| 00-2-012090 | 2/29/00 | D67N, D86E, K101K/E, Q102K/R, K103K/N, V118I, K122P, A158S, C162S, Q174H/R, D177E, <u>G190G/S</u>, <u>L210U/R/W</u>, R211K, <u>F214L</u>, T215Y, <u>H221H/Y</u>, <u>M230M/L</u>, <u>K238K/T</u>, A272P/S, K275K/Q, V276V/A/I/T, R277K, Q278Q/H, K281K/R, T286A, V293I | 144.0 | >450 | >600 |

Fig. 5

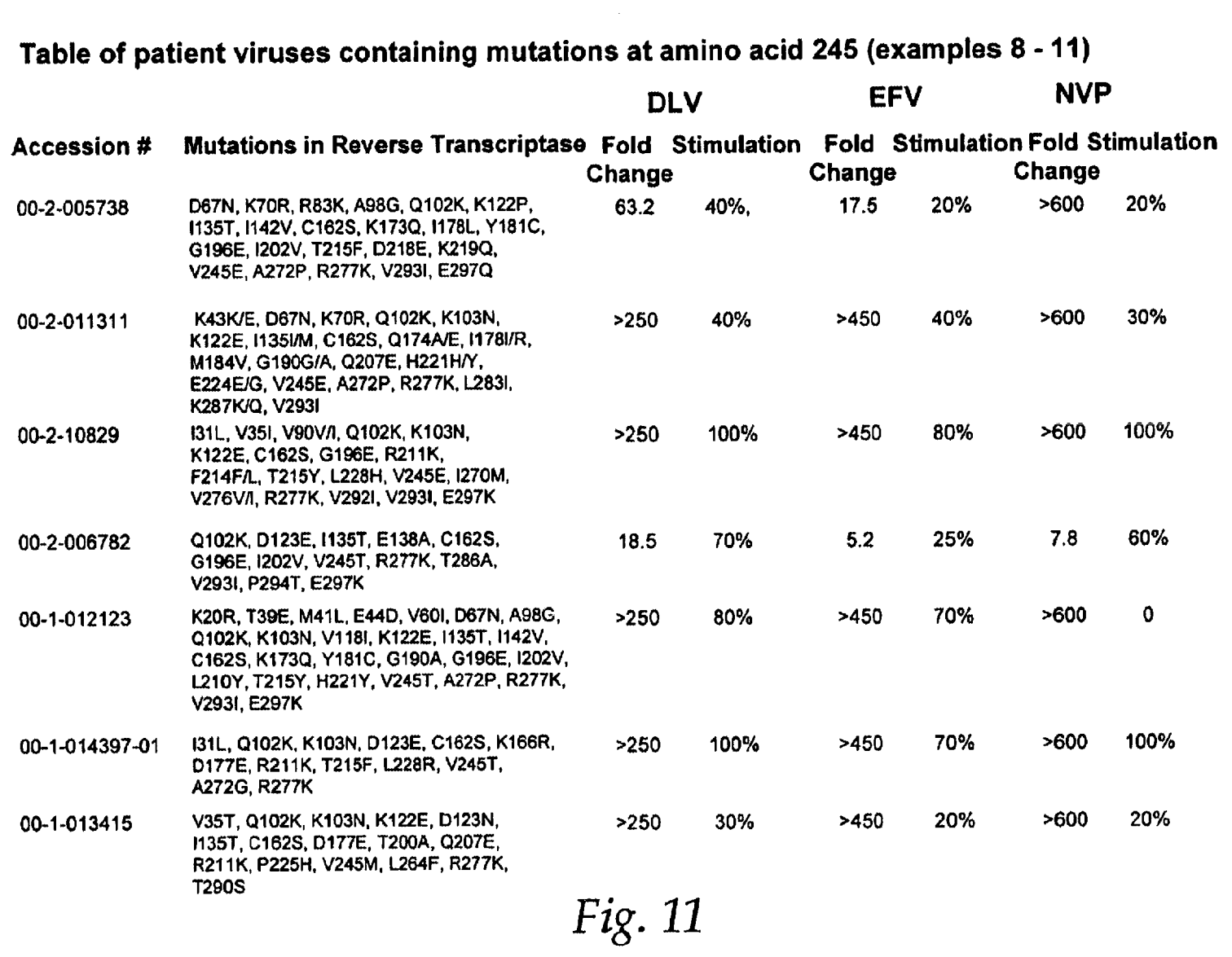

Table of patient viruses containing mutations at amino acid 245 (examples 8 - 11)

| Accession # | Mutations in Reverse Transcriptase | DLV Fold Change | DL

Patient 13522, reduced susceptibility to NNRTI and drug dependent stimulation of viral replication associated with a mutation at 270 (example 12)

Reduced Susceptibility and drug-dependent Stimulation of Viral Replication: Site Directed Mutants I270S

Clinical History of Patient 1033

| Sample ID | Date of Draw | Drug treatment | Duration | Viral load | NVP | DLV | EFV |
|---|---|---|---|---|---|---|---|
| 97-309 | 09/17/97 | AZT, 3TC, IDV | 2 yrs. | 545000 | 1.78 | 0.97 | 1.03 |
| 98-754 | 09/22/97 | " | 2 yrs. | 801000 | 1.19 | 1.16 | |
| | 10/03/97 | ABC, d4T, NFV, SQV | start | 900000 | | | |
| 98-1032 | 10/10/97 | NVP, d4T, NFV, SQV | start | 1160000 | 1.37 | 0.79 | 0.93 |
| | 10/15/97 | | | 2120000 | | | |
| 00-2-011658 | 11/12/97 | " | | 13300 | 2.6 | 1.1 | 1.4 |
| 00-2-011659 | 11/19/97 | " | | 84500 | 272 | 3.1 | 4.5 |
| | 12/03/97 | | | 329000 | | | |
| 98-1033 | 12/29/97 | d4T, NFV, SQV | start | 1220000 | *, dip-250% | 13.2, dip--180% | 214, dip-170% |
| 99-2-8973 | 01/28/98 | " | 12wks | 277000 | *, dip-180% | 18.4, dip-100% | 300, dip-150% |
| 98-757 | 02/26/98 | " | 16 wks | 488000 | *, dip-80% | 5.2, dip-20%? | 16.1, dip-80% |
| | 03/25/98 | | | 831000 | | | |
| 99-2-8980 | 04/22/98 | " | 24 wks | 607000 | *, dip-40% | 9.3, dip-25% | 28, dip-30% |
| | 05/20/98 | | | 572000 | | | |
| | 06/17/98 | | | 397000 | | | |
| 98-1080 | 07/15/98 | AZT, 3TC, IDV | start | 354000 | *, dip-45% | 2.77, dip-20% | 21.86, dip-50% |
| | 08/24/98 | | | 100000 | | | |
| AA1264 | 12/17/98 | " | | | 8.7 | 0.4 | 2.5 |
| 99-2-6174 | 05/20/99 | " | | | 9.87 | 0.07 | 1.59 |

*Fig. 16*

Sequences of Reverse Transcriptase of Patient 1033 Virus Samples

| Sample ID | RT Sequence |
|---|---|
| 97-309 (9/17/97) | V35I, D67N, T69D, K70R, L109I, M184V, V189I, T200A, I202T, H208Y, R211K, T215F, D218E, K219Q, H221Y, L228H, L283I, R284K, V293I, E297K |
| 98-754 (9/22/97) | V35I, D67N, T69D, K70R, L109I, M184V, V189L, T200A, I202T, H208Y, R211K,T215F, D218E, K219Q, H221Y, L228H, L283I, R284K, V293I, E297K |
| 98-1032 (10/10/97) | V35I, D67N, T69D, K70R, L109I, M184V, V189L, T200A, I202T, H208Y, R211K, T215F, D218E, K219Q, H221Y, L228H, L283I, R284K, V293I, E297K |
| 00-2-011658 (11/12/97) | V35I, D67N, T69D, K70R, L109L/MI, M184V, Y181Y/C, V189V/L, T200A, I202T, H208H/Y, R211K, T215F, D218E, K219Q, H221H/Y, L228H, L283I, R284K, T286T/A, V293I, E297K |
| 00-2-011659 (11/19/97) | V35I, D67N, T69D, K70R, L109L/I/MI, V179V/I, Y181Y/C, M184M/V, V189V/L, T200A, I202T, H208Y, R211K, T215F, D218E, K219Q, H221Y, F227F/L, L228H, L283I, R284K, T286T/A, V293I, E297K |
| 98-1033 (12/29/97) | V35I, D67N, T69D, K70R, V106A, V189L, T200A, I202T, H208Y, R211K, T215F, D218E, K219Q, H221Y, F227L, L228H, L283I, R284K, T286A, V293I, E297K |
| 99-2-008973 (1/28/98) | V35I, D67N, T69D, K70R, V106V/A, V108V/I, L109L/V, Y181C, V189L, T200A, I202T, H208Y, R211K, T215F, D218E, K219Q, H221Y, F227L, L228H, L283I, R284K, T286A, V293I, E297K |
| 98-757 (2/26/98) | V35I, D67N, T69D, K70R, V108I, L109V, Y181C, D121D/Y, Y181C, V189L, T200A, I202T, H208Y, R211K, T215F, D218E, K219Q, H221Y, F227L, L228H, L283I, R284K, T286T/A, V293I, E297K |
| 99-2-8980 (4/22/98) | V35I, D67N, T69D, K70R, V108I, L109V, Y181C, V189L, T200A, I202T, H208Y, R211K, T215F, D218E, K219Q, H221Y, F227L, L228H, L283I, R284K, T286T/A, V293I, E297K |
| 98-1080 (7/15/98) | (V35I), D67N, T69D, K70R, V108I, L109V, Y181C, V189L, T200A, I202T, H208Y, R211K, T215F, D218E, K219Q, H221Y, F227L, L228H, L283I, R284K, T286T/A, V293I, E297K |
| AA1264 (12/17/98) | V35M/I, D67N, T69D, K70R, V108V/I, L109?, D121D/Y, M184V, V189L, T200A, I202T, H208Y, R211K,T215Y, D218E, K219Q, H221Y, F227F/L, L228H, L283I, R284K, T286A, V293V/I, E297K |
| 99-2-006174 (5/20/99) | V35M, D67N, T69D, K70R, L109I, D121Y, M184V, V189X, T200A, I202T, H208Y, R211K, T215F, D218E, K219Q, H221Y, F227L, L228H, L283I, R284K, T286A, E297K |
| 00-2-011720 (2/14/00) | V35M, D67N, T69D, K70R, V108I, L109V, D121Y, Y181C, V189L, G190A, T200A, I202T, H208Y, R211K, T215F, D218E, K219Q, H221Y, F227L, L228H, L283I, R284K, T286A, V293V/I, E297K |

Fig. 17

METHODS FOR MONITORING ANTIRETROVIRAL THERAPY AND GUIDING THERAPEUTIC DECISION IN THE TREATMENT OF HIV/AIDS

This application claims the benefit of U.S. Provisional Application No. 60/211,245, filed Jun. 12, 2000, the content of which is incorporated herein by reference in its entirety.

Throughout this application, various publications are referenced by author and date within the text. Full citations for these publications may be found listed alphabetically at the end of the specification immediately preceding the claims. All patents, patent applications and publications cited herein, whether supra or infra, are hereby incorporated by reference in their entirety. The disclosures of these publications in their entireties are hereby incorporated by reference into this application in order to more fully describe the state of the art as known to those skilled therein as of the date of the invention described and claimed herein.

TECHNICAL FIELD

This invention relates to antiretroviral drug susceptibility and resistance tests to be used in identifying effective drug regimens for the treatment of human immunodeficiency virus (HIV) infection and acquired immunodeficiency syndrome (AIDS). The invention further relates to the means and methods of monitoring the clinical progression of HIV infection and its response to antiretroviral therapy using phenotypic or genotypic susceptibility assays. The invention also relates to novel vectors, host cells and compositions for carrying out phenotypic susceptibility tests. The invention further relates to the use of various genotypic methodologies to identify patients whose infection has become less susceptible ("resistant") to a particular antiretroviral drug regimen. This invention also relates to the screening of candidate antiretroviral drugs for their capacity to inhibit viruses, selected viral sequences and/or viral proteins. More particularly, this invention relates to using phenotypic susceptibility tests and/or genotypic tests to identify patients whose virus/viruses exhibit drug-dependent stimulation of replication in the presence of anti-retroviral agents.

BACKGROUND OF THE INVENTION

HIV infection is characterized by high rates of viral turnover throughout the disease process, eventually leading to CD4 depletion and disease progression (Wei X, Ghosh S K, Taylor M E, et al. (1995) *Nature* 343, 117–122) (Ho D D, Naumann A U, Perelson A S, et al. (1995) *Nature* 373, 123–126). The aim of antiretroviral therapy is to achieve substantial and prolonged suppression of viral replication. Achieving sustained viral control is likely to involve the use of sequential therapies, generally each therapy comprising combinations of three or more antiretroviral drugs. Choice of initial and subsequent therapy should, therefore, be made on a rational basis, with knowledge of resistance and cross-resistance patterns being vital to guiding those decisions. The primary rationale of combination therapy relates to synergistic or additive activity to achieve greater inhibition of viral replication. The tolerability of drug regimens will remain critical, however, as therapy will need to be maintained over many years.

In an untreated patient, some $10^{10}$ new viral particles are produced per day. Coupled with the failure of HIV reverse transcriptase (RT) to correct transcription errors by exonucleolytic proofreading, this high level of viral turnover results in $10^4$ to $10^5$ mutations per day at each position in the HIV genome. The result is the rapid establishment of extensive genotypic variation. While some template positions may be more error prone, (Mansky L M, Temin H M (1995) *J Virol* 69, 5087–5094) (Schinazi R F, Lloyd R M, Ramanathan C S, et al. (1994) *Antimicrob Agents Chemother* 38, 268–274), mathematical modeling suggests that, at every nucleotide position, mutation may occur $10^4$ times per day in infected individuals.

For antiretroviral drug resistance to occur, the target enzyme must be modified while preserving its function in the presence of the inhibitor. Point mutations leading to an amino acid substitution may result in changes in shape, size, or charge of the active site, substrate binding site, or surrounding regions of the enzyme. Mutants resistant to antiretroviral agents have been detected at low levels before the initiation of therapy (Mohri H, Singh M K, Ching W T W, et al. (1993) *Proc Natl Acad Sci USA* 90, 25–29) (Nájera I, Richman D D, Olivares I, et al. (1994) *AIDS Res Hum Retroviruses* 10, 1479–1488) (Nájera I, Holguin A, Quiñones-Mateu E, et al. (1995) *J Virol* 69, 23–31). However, these mutant strains represent only a small proportion of the total viral load and may have a replication or competitive disadvantage compared with wildtype virus (Coffin J M (1995) *Science* 267, 483–489). The selective pressure of antiretroviral therapy provides these drug-resistant mutants with a competitive advantage and thus they come to represent the dominant quasispecies (Frost S D W, McLean A R (1994) *AIDS* 8, 323–332) (Kellam P, Boucher C A B, Tijnagal J M G H (1994) *J Gen Virol* 75, 341–351) ultimately leading to drug resistance and virologic failure in the patient.

A mutation or mutations that results in virus that can not only replicate in the presence of drug (i.e. resistant virus) but could actually replicate more efficiently in the presence of drug than in the absence of drug (i.e. drug-dependent stimulation of virus), would present an especially important phenotype to identify. In this case, a drug could actually accelerate the rate of destruction to the immune system and progression of disease.

Non-Nucleoside Reverse Transcriptase Inhibitors (NNRTIs)

Non-nucleoside reverse transcriptase inhibitors (NNRTIs) are a chemically diverse group of compounds which are potent inhibitors of HIV-1 Reverse Transcriptase (RT) in vitro. These compounds include pyridinone derivatives, bis(heteroaryl) piperazines (BHAPs) such as delavirdine and atevirdine, the dipyridodiazepinone (nevirapine), the thymine derivative groups (TSAO and HEPT), an a-anilino phenylacetamide (a-APA) compound (loviride), the quinoxaline-class inhibitors (HBY-097), the benzodiazepinone and -thione (TIBO) compounds, and the pyridinone derivatives (L-697,661). For overviews, see (DeClercq E. (1996) *Rev Med Virol* 6, 97–117) (Emini E A (1996) *Antiviral Drug Resistance*, ed. D D Richman, John Wiley & Sons, Ltd). Three NNRTIs: nevirapine (NVP, Viramune, Boehringer Ingelheim, Ingelheim am Rhein, Germany), delavirdine (DLV, Rescriptor, Pharmacia & Upjohn, Kalamazoo, Mich., USA), and efavirenz (EFV, Sustiva, Dupont, Wilmington, Del., USA) are licensed for use in the USA.

High-level resistance to individual compounds appears to develop rapidly, often within a few weeks of initiating monotherapy, frequently involving only single-point mutations, and in many cases leading to considerable cross-resistance to other NNRTIs. Most mutations reported occur in the codon groups 100–108 and 181–190 which encode for the two b-sheets adjacent to the catalytic site of the RT enzyme (Kohlstaedt L A, Wang J, Friedman J M, et al. (1992) *Science* 256, 1783–90). The NNRTI binding pocket, as it has been described, is a hydrophobic non-substrate binding region of RT where these agents directly interact with RT. They inhibit activity by interfering with mobility of the 'thumb' subdomain, or disrupting the orientation of conserved aspartic acid side chains essential for catalytic activity (D'Aquilla R T. (1994) *Clin Lab Med* 14, 393–423) (Arnold E., Ding J., Hughes S H, et al. (1995) *Curr Opin Struct Biol* 5, 27–38).

Mutations conferring reduced susceptibility to nevirapine have been described at HIV RT codons 98, 100, 103, 106, 108, 181, 188 and 190 (Richman D D, Havlir D, Corbeil J. (1994) *J Virol* 68, 1660–1666). The most frequently selected variant during nevirapine monotherapy is a $Tyr^{181}aCys$ (Y181C) mutation, which results in a 100-fold reduction in sensitivity to this agent, and with reduced susceptibility to the pyridinone derivatives (L-696,229 and L-697,661) (Arnold, Ibid). TSAO also has limited activity in the presence of the Y181C mutation, but maintains activity in the presence of mutations HIV RT at codons 100 and 103, and in vitro selects for a unique mutation, $GLU^{138}aLys$ (E138K), in the region where it most closely interacts with RT (Richman, D D, Ibid) (Richman D D, Shih C K, Lowy I, et al. (1991) *Proc Natl Acad Sci USA* 88, 11241–11245).

Resistance to loviride when used as monotherapy develops in most patients by week 24. It has been mapped to a range of HIV RT codons 100–110; 181–190), most commonly codon 103 (Staszewski S, Miller V, Kober A, et al. (1996) *Antiviral Ther* 1, 42–50). During combination therapy using loviride with zidovudine or zidovudine plus lamivudine, variants at codons 98 and 103 were the most frequent mutations detected at 24 weeks (Staszewski S, Miller V, Rehmet S, et al. (1996) *AIDS* 10, F1-7).

Although the K101E, K103N, and Y181C, mutations also confer cross-resistance to BHAPs, (Balzarini J, Karlsson A, Pérez-Pérez M-J, et al. (1992) *Virology* 192, 246–253) the characteristic P236L substitution selected for by these agents in vitro appears to sensitize RT to some other NNRTIs, reducing the IC50 for nevirapine, for example, 7- to 10-fold, without influencing sensitivity to nucleoside analogues (Staszewski S., Ibid). This mutation at codon 236 has been observed in clinical isolates during atevirdine therapy, although other resistance-conferring mutations at codons 103 and 181 have been reported during monotherapy as well as at codons 101, 188, 233 and 238 during combination therapy with zidovudine.

While HBY-097 may initially select for a mutation at HIV RT codon 190 in vitro, further passage consistently selects for mutations at HIV RT codons 74 and 75, with some mutant viruses showing decreased sensitivity to didanosine and stavudine, but not zidovudine (Kleim J-P, Rösner M, Winkler I, et al. (1995) *J Acquir Immune Defic Syndr* 10 Suppl 3, 2).

Mutation at codon 181 has been reported to antagonize zidovudine resistance due to the typical 41 and 215 codon mutations, (Zhang D, Caliendo A M, Eron J J, et al. (1994) *Antimicrob Agents Chemother* 38, 282–287) suggesting that combination therapy with some NNRTIs and zidovudine may be feasible. Although an HIV mutant with triple resistance to zidovudine, didanosine and nevirapine has been described in vitro, (Larder B A, Kellam P, Kemp S D (1993) *Nature* 365, 451–453) treatment with this triple combination does provide superior immunological and virological responses than treatment with zidovudine plus didanosine alone over a 48-week period in patients with CD4 cell counts $<350/mm^3$.

Combination therapy with zidovudine and the pyridinone derivative L-697,661 prevents the appearance of the codon 181 mutation typically selected during monotherapy with this NNRTI, delaying the appearance of high-level resistance to this compound. Changes in susceptibility to zidovudine were not examined in this study (Staszewski S, Massari F E, Kober A, et al. (1995) *J Infect Dis* 171, 1159–1165). Concomitant or alternating zidovudine therapy does not delay the appearance of resistance during nevirapine therapy (Richman D D, Ibid) (Nunberg J H, Schleif W A, Boots E J, et al. (1990) *J Virol* 65, 4887–4892) (DeJong M D, Loewenthl M, Boucher C A B, et al. (1994) *J Infect Dis* 169, 1346–1350) (Cheeseman S H, Havlir D, McLaughlin M M, et al. (1995) *J Acquir Immune Defic Syndr* 8, 141–151. However, the 181 mutant is not being observed during treatment with this combination, and the most common mutation occurs at 190 (Richman D D, Ibid). This suggests that the codon 181 mutation, which is antagonistic to zidovudine resistance in vitro, is not compatible, or not preferred in vivo, with selection favoring other mutations which allow for reduced susceptibility to nevirapine concomitant with zidovudine resistance.

The rapid development of reduced susceptibility to the NNRTIs suggests limited utility of these agents, particularly as monotherapies, and has led to the modification of these molecules in an attempt to delay the appearance of drug-resistant virus. A 'second generation' NNRTI, the pyridinone derivative L-702,019, demonstrated only a 3-fold change in $IC_{50}$ between wild-type and codon 181 mutant HIV-1, and required multiple mutations to engender high-level resistance (Goldman M E, O'Brien J A, Ruffing T L, et al. (1993) *Antimicrob Agents Chemother* 37, 947–949).

Similarly, Efavirenz (EFZ) was introduced as a second generation NNRTI relatively recently. Efavirenz has a unique profile in that it retains activity against viruses containing the common RT mutation, Y181C. In vitro, efavirenz selects for mutations at codons 100, 101, 103, 108, 179, 181, and 188. This is similar to the in vivo resistance profile, which includes mutations at codons 100, 103, 108, 190 and 225, (and possibly 101, 179, 181 and 188). (Winslow D L, Garber S, Reid C, it al. Fourth International Antiviral Therapy 1977; 1(Suppl.1): 6. Conference on HIV Drug Resistance Sardinia, Italy, (1995) (Winslow D L, Garber S, Reid C, et al. *Antiviral Therapy* 1997; 1(suppl.1) :6) (Young S D, Britcher S F, Tran L O, et al. Antimicrobial Agents & Chemotherapy 1995; 39.2602–2609.) (Bacheler L T, Anton E, Jeffrey S, et. al. Antiviral Therapy 1998; 3(Suppl.1): 15–16) (Bacheler L T, Weislow O, Snyder S & Hanna G. $12^{th}$ World AIDS Conference, 1998, Geneva, Switzerland, Abstract 41213.)

It is an object of this invention to provide a drug susceptibility and resistance test capable of showing whether a viral population in a patient is resistant to a given prescribed drug. Another object of this invention is to provide a test that will enable the physician to substitute one or more drugs in a therapeutic regimen for a patient that has become resistant to a given drug or drugs after a course of therapy. Yet another object of this invention is to provide a test that will enable selection of an effective drug regimen for the treatment of HIV infections and/or AIDS. Yet another object of this invention is to provide the means for identifying the drugs to which a patient has become resistant, in particular identifying resistance to non-nucleoside reverse transcriptase inhibitors. (NNRTIs) Still another object of this invention is to provide a test and methods for evaluating the biological effectiveness of candidate drug compounds which act on specific viruses, viral genes and/or viral proteins particularly with respect to viral drug resistance associated with non-nucleoside reverse transcriptase inhibitors (NNRTIs). It is also an object of this invention to provide the means and compositions for evaluating HIV antiretroviral drug resistance and susceptibility. Still another object of this invention is to provide a means of determining whether a candidate anti-retroviral drug will cause increased or stimulated viral replication. This and other objects of this invention will be apparent from the specification as a whole.

SUMMARY OF THE INVENTION

The present invention relates to methods, using phenotypic and genotypic methods to monitor the clinical progression of human immunodeficiency virus infection and its response to antiviral therapy. The invention is also based, in part, on the discovery that genetic changes in HIV reverse transcriptase (RT), which confer resistance to antiretroviral therapy, may be rapidly determined directly from patient plasma HIV RNA using phenotypic or genotypic methods. The methods utilize polymerase chain reaction (PCR) based assays. Alternatively, methods evaluating viral nucleic acid or viral protein in the absence of an amplification step could utilize the teaching of this invention to monitor and/or modify antiretroviral therapy. This invention is based in part on the discovery of a mutation at codon 230 either alone or in combination with a mutation at codon 103 or 181 of HIV RT in NNRTI inhibitor treated patients, in which the presence of the mutations correlates with decreased susceptibility to delavirdine, nevirapine and efavirenz, and with drug-dependent stimulation of viral replication in the presence of delavirdine, nevirapine or efavirenz. The mutations were found in plasma HIV RNA after a period of time following initiation of therapy. The development of the mutation at codon 230, in addition to the mutation at codon 103 or 181 in HIV RT, was found to be an indicator of the development of resistance, and ultimately of immunological decline. Resistance test vectors containing the single site mutation at codon 230 (M230L), and M230L in combination with a mutation at either 103 (K103N) or 181 (Y181C) in reverse transcriptase were constructed using site directed mutagenesis (Sarkar G, Sommer S S. (1990). Biotechniques 8:404–407). These mutations were observed to be associated with decreased susceptibility to the NNRTI and, in some combinations, drug-dependent stimulation of viral replication.

This invention is based in part on the discovery of a mutation at codon 230 in combination with mutations at codons 101, 103, 190, 221 and 238 of HIV RT in NNRTI treated patients, in which the presence of the mutations correlates with a decrease in susceptibility to delavirdine, nevirapine and efavirenz, and with drugdependent stimulation of viral replication in the presence of delavirdine, nevirapine or efavirenz.

This invention is based in part on the discovery of a mutation at codon 241 of RT that was discovered to occur in NNRTI-treated patients. The presence of the mutation at 241, in addition to other NNRTI-resistance mutations (these mutations may include previously described NNRTI-resistance mutations such as: K101E, K103N, V106M, I135T, E138A and G190A) correlates with decreased susceptibility to delavirdine, nevirapine and efavirenz. Resistance test vectors containing patient sequences with these mutations exhibited reduced susceptibility to delavirdine, nevirapine and efavirenz as well as drug dependent stimulation of replication in the presence of all three drugs.

This invention is based in part on the discovery of mutations at codon 245 of RT that was discovered to occur in NNRTI-treated patients. The presence of the mutation at 245, in addition to other NNRTI-resistance mutations (which may include previously described NNRTI-resistance mutations such as: A98G, K101E, K103N, I135T, E138A, Y181C, G190A and P225H) correlates with decreased susceptibility to delavirdine, nevirapine and efavirenz. Resistance test vectors containing patient sequences with these mutations exhibited reduced susceptibility to delavirdine, nevirapine and efavirenz as well as drug dependent stimulation of replication in the presence of all three drugs. Resistance test vectors containing a single site mutation at codon 245 (V245E or T), and as well as test vectors containing V245E or T in combination with mutations at 103 (K103N) and 135 (I135T) in RT were constructed using site directed mutagenesis. While V245E alone had no effect on susceptibility to the NNRTI, The triple combination of mutations (K103N, I135T and 245 E or T) was observed to be associated with decreased susceptibility to the NNRTI and drug-dependent stimulation of viral replication.

This invention is based in part on the discovery of a mutation at codon 270 of RT that was discovered to occur in NNRTI-treated patients. The presence of the mutation at 270 in addition to other NNRTI-resistance mutations (which may include previously described NNRTI-resistance mutations such as: K103N, I135T and P225H) correlates with decreased susceptibility to delavirdine, nevirapine and efavirenz, and drug-dependent stimulation of viral replication. This invention is based in part on the discovery of a patient-derived segment containing multiple mutations at HIV RT codons 35, 67, 69, 70, 106, 189, 200, 202, 208, 211, 215, 218, 219, 221, 227, 228, 283, 284, 286, 293 and 297 of RT that was discovered in an NNRTI-treated patient. Resistance test vectors containing patient sequences with these mutations exhibited reduced susceptibility to delavirdine, nevirapine and efavirenz as well as drug dependent stimulation of replication in the presence of all three drugs. Site-directed reversion of specific mutations demonstrated that many of the mutations play a role in the drug-dependent stimulation of viral replication, but that none of the mutations is sufficient on it's own to cause such an effect. Specifically, mutations at 106, 189, 227, 283, 284 and 286 are observed to modulate the resistance and stimulation of viral replication seen with this.

BRIEF DESCRIPTION OF THE FIGURES

FIG. 1. Resistance Test Vector. Schematic representations of the HIV-1 genome (top panel) and the resistance test vector (bottom panel), comprising a patient derived segment and an indicator gene viral vector.

FIG. 5. Table of patient viruses containing mutations at HIV RT codon position 230, as described in Examples 3, 4, and 5.

FIG. 11. Reverse mutagenesis of HIV RT codon positions 245, 270, 277, 292, 293, and 297 in Patient 010829, as described in Example 11. The results from each mutant are compared to results obtained from a drug susceptible virus control, such as PNL4-3, or HXB-2. The top panel of the figure shows the graphs from the patient sample, containing the mutations at codon positions 245, 270, 277, 292, 293, and 297. In these graphs, stimulation of viral replication manifests as percent inhibition less than zero (i.e. negative inhibition) for all three NNRTIs (delavirdine, efavirenz, and nevirapine). The second panel of graphs shows the site-directed reversion of the mutation at codon 245, followed by the reversion of the mutation at codon 270. Both single reverse mutants retain profiles consistent with drug-dependent stimulation of viral replication (negative inhibition) in the presence of any of the NNRTIs (delavirdine, efavirenz, or nevirapine). The bottom panel shows the reversion of HIV-RT mutations at codons 245, 270, 277, 292, 293, and 297. In this final panel of graphs, there is no longer negative inhibition (stimulation of viral replication) in any of the three NNRTIs (delavirdine, efavirenz, or nevirapine), although this site-directed mutant retains reduced drug susceptibility (drug resistance).

FIG. 16. Effect of specific mutations on 1033-3 virus as discussed in Example 14, as determined by sitedirected mutagenesis. The results from each mutant are compared to results obtained from a drug susceptible virus control, such as PNL4-3, or HXB-2. In these graphs, stimulation of viral replication manifests as percent inhibition less than zero (i.e. negative inhibition).

FIG. 17. Effect of M184V mutation on stimulation phenotype as described in Example 14, as determined by site-directed mutagenesis. Reversion of the mutation at HIV RT codon 184 results in increasing levels of drug-dependent stimulation of viral replication, as manifested by percent inhibition less than zer0 (i.e. negative inhibition).

DETAILED DESCRIPTION OF THE INVENTION

Figure 2:
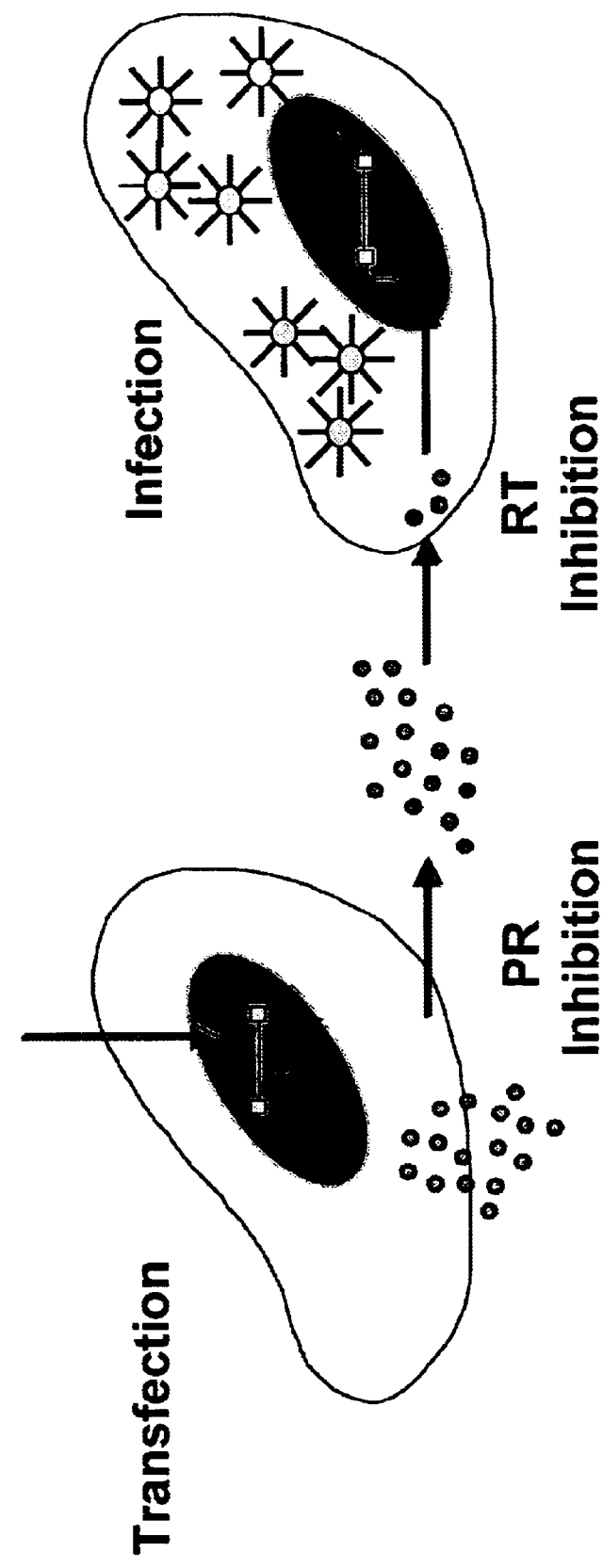
FIG. 2. Two Cell Assay. Schematic Representation of the Assay. A resistance test vector is generated by cloning the patient-derived segment (PDS) into an indicator gene viral vector. Using defective PR and RT sequences, it was shown that luciferase activity is dependent on functional PR and RT. The resistance test vector is co-transfected with an expression vector that produces amphotropic murine leukemia virus (MLV) envelope protein or other viral or cellular proteins, which enable infection. Pseudotyped viral particles are produced containing the protease (PR) and the reverse transcriptase (RT) gene products encoded by the patient-derived segment (PDS). The particles are then harvested and used to infect fresh cells. The assay is performed in the absence of drug and in the presence of drug over a wide range of concentrations. Protease PR inhibitors are added to the cells following transfection, and are thus present during particle maturation. In contrast, RT inhibitors are added to the cells at the time of, or prior to, viral particle infection. The amount of luciferase is determined and the percentage (%) inhibition is calculated at the different drug concentrations tested.

The present invention relates to methods of monitoring the clinical progression of HIV infection in patients receiving antiretroviral therapy, particularly non-nucleoside reverse transcriptase inhibitor (NNRTI) antiretroviral therapy, and to the detection of variants of HIV that exhibit drug-dependent stimulation of replication in the presence of one or more NNRTIs.

In one embodiment, the present invention provides for a method of assessing the effectiveness of antiretroviral therapy of a patient comprising (i) collecting a biological sample from an HIV-infected patient; and (ii) determining whether the biological sample comprises nucleic acid encoding HIV RT having a mutation at one or more positions codon in the RT. The mutation(s) correlate positively with changes in phenotypic susceptibility/resistance.

In a specific embodiment, the invention provides for a method of assessing the effectiveness of NNRTI antiretroviral therapy of a patient comprising (i) collecting a biological sample from an HIV-infected patient; and (ii) determining whether the biological sample comprises nucleic acid encoding HIV RT having a mutation at codon 230 and 103 or 181. Using a phenotypic susceptibility assay, this invention established that mutations at codon 230, either alone or in combination with a mutation at codon 103 or 181 of HIV RT, correlate with a decreased susceptibility to delavirdine, nevirapine and efavirenz. Patient derived resistance test vectors containing the mutation M230L, either alone or in combination with other NNRTI-resistance mutations show reductions in susceptibility that range from 10-fold to >450-fold for delavirdine, from 5-fold to >250-fold for efavirenz, and from 10-fold to >600-fold for nevirapine. The percent stimulation of viral replication in patient derived resistance test vectors containing mutations at codon 230 in HIV RT ranges from 0% to ~100% for all three NNRTIs. Site-directed resistance test vectors containing mutations at 230, either alone or in combination with 103 or 181 were constructed. The mutation at 230 alone causes reduced susceptibility to delavirdine (58-fold), nevirapine (40-fold) and efavirenz (23-fold), and drug-dependent stimulation of replication in the presence of nevirapine (~50%) and delavirdine (~50%). The combination of mutations at 230 and 103 causes reduced susceptibility to delavirdine (>250-fold), nevirapine (>600-fold) and efavirenz (>470-fold) and drug-dependent stimulation of replication in the presence of delavirdine (~100%) nevirapine (~70%), and efaviraenz (~40%). The combination of mutations at 230 and 181 causes reduced susceptibility to delavirdine (>250-fold), nevirapine (>800-fold) and efavirenz (25-fold) but no drug-dependent stimulation of replication in the presence of delavirdine, nevirapine, or efaviraenz.

In another specific embodiment, the invention provides for a method of evaluating the effectiveness of NNRTI antiretroviral therapy of a patient comprising (i) collecting a biological sample from an HIV-infected patient; and (ii) determining whether the biological sample comprises nucleic acid encoding HIV RT having a mutation at codon 241, 103 and 135 or at codon 241 in combination with mutations at 101, 106, 135, 138 and 190. Using a phenotypic susceptibility assay, this invention established that mutations at codon 241, in combination with a mutation at codon 103, or mutations at 101, 106 and 190 of HIV RT are correlated with decreased susceptibility (increased resistance) to delavirdine, nevirapine and efavirenz. Patient-derived resistance test vectors containing mutations at 241 in addition to other NNRTI-resistance mutations (e.g. 101, 103, 106, 135, 138 and 190) displayed reductions in susceptibility ranging from 41-fold to >250-fold for delavirdine, and showed high level reductions in susceptibility to nevirapine (>600-fold) and efavirenz (>470-fold). Patient-derived resistance test vectors containing mutations at 241 in combination with other NNRTI-resistance mutations (e.g. 101, 103, 106, 135, 138 and 190) displayed drug-dependent stimulation of viral replication ranging from 70–100% for all three NNRTIs.

In another specific embodiment, the invention provides for a method of assessing the effectiveness of NNRTI antiretroviral therapy of a patient comprising (i) collecting a biological sample from an HIV-infected patient; and (ii) determining whether the biological sample comprises nucleic acid encoding HIV RT having a mutation at codon 245, 103 and 135 or having a mutation at codon 245 in combination with additional mutations that could include 98, 101, 103, 135, 138, 181, 190 and/or 225. Using a phenotypic susceptibility assay, this invention established that a mutation at codon 245 in combination with mutations at codons 103 and 135, or a mutation at codon 245 with additional mutations that may include 98, 101, 103, 135, 138, 181, 190 and 225 of HIV RT correlated with decreased susceptibility to delavirdine, nevirapine and efavirenz. Patient-derived resistance test vectors containing mutations at 245 and additional NNRTI-resistance mutations as described above exhibited reductions in susceptibility ranging from 20-fold to >250-fold for delavirdine, from 8-fold to >600-fold for nevirapine and from 5-fold to >470-fold for efavirenz. Patient-derived resistance test vectors containing mutations at 245 and additional NNRTI-resistance mutations as described above exhibited drug-dependent stimulation in viral replication ranging from 20–100% for all three NNRTIs. Site-directed resistance test vectors were constructed containing mutations at 245, 103 and 135 and in various combinations as described above. Mutations at HIV RT codon 245 (V245E or V245T) alone cause no significant reduction in susceptibility to delavirdine, nevirapine or efavirenz. The combination of mutations at 245 (V245E)

with 103 (K103N) and 135 (I135T) causes reduced susceptibility to delavirdine (169-fold), nevirapine (244-fold) and efavirenz (93-fold) and drug-dependent stimulation of replication in the presence of delavirdine (~20%) and nevirapine (~15%) but not efavirenz. The combination of mutations at 245 (V245T) with 103 (K103N) and 135 (I135T) causes reduced susceptibility to delavirdine (>250-fold), nevirapine (544-fold) and efavirenz (174-fold) and drug-dependent stimulation of replication in the presence of delavirdine (~50%), nevirapine (~40%), and efavirenz (~25%).

In another specific embodiment, the invention provides for a method of evaluating the effectiveness of NNRTI antiretroviral therapy of a patient comprising (i) collecting a biological sample from an HIV-infected patient; and (ii) determining whether the biological sample comprises nucleic acid encoding HIV RT having a mutation at codon 270 and additional mutations at codons 103 and 135, with or without mutation at codon 225. Using a phenotypic susceptibility assay, this invention established that mutation at codon 270 in combination with mutations at codon 103 and 135 with or without mutation at codon 225 of HIV RT are correlated with a decreased susceptibility to delavirdine, nevirapine, and efavirenz, and drug-dependent stimulation of replication in the presence of delavirdine, nevirapine and efavirenz. Patient-derived resistance test vectors containing mutations at 270 in addition to other NNRTI-resistance mutations (e.g. 103, 135, with or without 225) displayed high-level reductions in susceptibility to all three NNRTIs and drug-dependent Stimulations in viral replication ranging from 80–110% for all three NNRTIs.

Under the foregoing circumstances, the phenotypic susceptibility/resistance profile and genotypic profile of the HIV virus infecting the patient has been altered, reflecting some change in the response to the antiretroviral agent. In the case of NNRTI antiretroviral therapy, the HIV virus infecting the patient may be resistant to any combination of the three NNRTIs described herein. Furthermore, the virus may be found to replicate more efficiently in the presence of one or more drug(s) than in the absence of those drugs. It therefore may be desirable after detecting the mutation, to either increase the dosage of the antiretroviral agent, change to another antiretroviral agent, or add one or more additional antiretroviral agents to the patient's therapeutic regimen. For example, if the patient was being treated with efavirenz (DMP-266) when the 230 and 103 mutation arose, the patient's therapeutic regimen may desirably be altered by eliminating NNRTI antiretroviral agents, such as delavirdine, efavirenz or nevirapine; and/or (ii) adding another antiretroviral agent to the patient's therapeutic regimen. The effectiveness of the modification in therapy may be evaluated by monitoring viral burden such as by HIV RNA copy number. A decrease in HIV RNA copy number correlates positively with the effectiveness of a treatment regimen.

The phrase "correlates positively," as used herein, indicates that a particular result renders a particular conclusion more likely than other conclusions.

Another preferred, non-limiting, specific embodiment of the invention is as follows: A method of assessing the effectiveness of NNRTI therapy of a patient, comprising: (i) collecting a biological sample from an HIV-infected patient; (ii) transcribing the HIV-encoding RNA in the biological sample to cDNA; (iii) amplifying a patient-derived segment (PDS) using HIV PCR primers that result in a product comprising the RT gene; (iv) performing sequencing reactions using primers that yield sequences comprising wild type or mutant amino acids at codons 230, 103 and 181; and (v) determining the presence or absence of mutations at codons 230, 103 and 181 from the sequences.

Yet another preferred, non-limiting, specific embodiment of the invention is as follows: A method of assessing the effectiveness of NNRTI therapy of a patient, comprising: (i) collecting a biological sample from an HIV-infected patient; (ii) transcribing the HIV-encoding RNA in the biological sample to cDNA; (iii) amplifying a patient-derived segment (PDS) using HIV PCR primers that result in a product comprising the RT gene; (iv) performing sequencing reactions using primers that yield sequences comprising wild type or mutant amino acids at codons 230, 101, 103, 190, 221, and 238; and (v) determining the presence or absence of mutations at codons 230, 101, 103, 190, 221, and 238 from the sequences.

This invention also provides for a method of assessing the effectiveness of non nucleoside reverse transcriptase antiretroviral therapy of an HIV-infected patient comprising: (a) collecting a biological sample from an HIV-infected patient; and (b) evaluating whether the biological sample comprises nucleic acid encoding HIV reverse transcriptase having a mutation at codon 230 alone or in combination with a mutation at codon 103 or a mutation at codon 181, wherein the presence of such a mutation correlates with a decrease in non-nucleoside reverse transcriptase inhibitor susceptibility and drug-dependent stimulation of viral replication.

This invention also provides for a method for assessing the biological effectiveness of a candidate HIV antiretroviral drug compound comprising: (a) introducing a resistance test vector comprising a patient-derived segment further comprising a mutation at codon 230 alone or in combination with a mutation at codon 103 or a mutation at codon 181 and an indicator gene into a host cell; (b) culturing the host cell from step (a); (c) measuring the expression of the indicator gene in a target host cell; and (d) comparing the measurement of the expression of the indicator gene from step (c) with the measurement of the expression of the indicator gene measured when steps (a)–(c) are carried out in the absence of the candidate antiretroviral drug compound; wherein a test concentration of the candidate antiretroviral drug compound is present at steps (a)–(c); at steps (b)–(c); or at step (c) and wherein a decrease in expression of the indicator gene measured in the persence of the candidate antiretroviral drug compound is indicative of the biological effectiveness of the compound.

This invention provides for a resistance test vector comprising: (i) an HIV patient-derived segment which comprises reverse transcriptase having a mutation in at least one of codons 230, 103 or 181, and (ii) and an indicator gene, wherein the expression of the indicator gene is dependent upon the patient derived segment.

This invention also provides for a method of assessing the effectiveness of non nucleoside reverse transcriptase antiretroviral therapy of an HIV-infected patient comprising:
 (a) collecting a biological sample from an HIV-infected patient; and
 (b) evaluating whether the biological sample comprises nucleic acid encoding HIV reverse transcriptase having a mutation at codon 230 alone or in combination with at least one mutation at a codon selected from the group consisting of: codon 101, codon 103, codon 190, codon 221 and codon 238, wherein the presence of the mutations correlate with a decrease in non-nucleoside reverse transcriptase inhibitor susceptibility and drug-dependent stimulation of viral replication.

Yet another preferred, non-limiting, specific embodiment of the invention is as follows: A method of assessing the effectiveness of NNRTI therapy of a patient, comprising: (i) collecting a biological sample from an HIV-infected patient; (ii) transcribing the HIV-encoding RNA in the biological sample to CDNA; (iii) amplifying a patient-derived segment (PDS) using HIV PCR primers that result in a product comprising the RT gene; (iv) performing sequencing reactions using primers that yield sequences comprising wild type or mutant amino acids at codons 241, 103 and 135; and (v) determining the presence or absence of mutations at codons 241, 103 and 135 from the sequences.

Yet another preferred, non-limiting, specific embodiment of the invention is as follows: A method of assessing the effectiveness of NNRTI therapy of a patient, comprising: (i) collecting a biological sample from an HIV-infected patient; (ii) transcribing the HIV-encoding RNA in the biological sample to cDNA; (iii) amplifying a patient-derived segment (PDS) using HIV PCR primers that result in a product comprising the RT gene; (iv) performing sequencing reactions using primers that yield sequences comprising wild type or mutant amino acids at codons 241, 101, 106, 135, 138, and 190; and (v) determining the presence or absence of mutations at codons 241, 101, 106, 135, 138, and 190 from the sequences.

Yet another preferred, non-limiting, specific embodiment of the invention is as follows: A method of assessing the effectiveness of NNRTI therapy of a patient, comprising: (i) collecting a biological sample from an HIV-infected patient; (ii) transcribing the HIV-encoding RNA in the biological sample to cDNA; (iii) amplifying a patient-derived segment (PDS) using HIV PCR primers that result in a product comprising the RT gene; (iv) performing sequencing reactions using primers that yield sequences comprising wild type or mutant amino acids at codons 245, 98, 135 and 181; and (v) determining the presence or absence of mutations at codons 245, 98, 135 and 181 from the sequences.

Yet another preferred, non-limiting, specific embodiment of the invention is as follows: A method of assessing the effectiveness of NNRTI therapy of a patient, comprising: (i) collecting a biological sample from an HIV-infected patient; (ii) transcribing the HIV-encoding RNA in the biological sample to cDNA; (iii) amplifying a patient-derived segment (PDS) using HIV PCR primers that result in a product comprising the RT gene; (iv) performing sequencing reactions using primers that yield sequences comprising wild type or mutant amino acids at codons 245, 101, 103, 135 and 190; and (v) determining the presence or absence of mutations at codons 245, 101, 103, 135, and 190 from the sequences.

Yet another preferred, non-limiting, specific embodiment of the invention is as follows: A method of assessing the effectiveness of NNRTI therapy of a patient, comprising: (i) collecting a biological sample from an HIV-infected patient; (ii) transcribing the HIV-encoding RNA in the biological sample to cDNA; (iii) amplifying a patient-derived segment (PDS) using HIV PCR primers that result in a product comprising the RT gene; (iv) performing sequencing reactions using primers that yield sequences comprising wild type or mutant amino acids at codons 245, 103, 225, and 270; and (v) determining the presence or absence of mutations at codons 245, 103, 225 and 270 from the sequences.

Yet another preferred, non-limiting, specific embodiment of the invention is as follows: A method of assessing the effectiveness of NNRTI therapy of a patient, comprising: (i) collecting a biological sample from an HIV-infected patient; (ii) transcribing the HIV-encoding RNA in the biological sample to cDNA; (iii) amplifying a patient-derived segment (PDS) using HIV PCR primers that result in a product comprising the RT gene; (iv) performing sequencing reactions using primers that yield sequences comprising wild type or mutant amino acids at codons 245, 135 and 138; and (v) determining the presence or absence of mutations at codons 245, 135 and 138 from the sequences.

Yet another preferred, non-limiting, specific embodiment of the invention is as follows: A method of assessing the effectiveness of NNRTI therapy of a patient, comprising: (i) collecting a biological sample from an HIV-infected patient; (ii) transcribing the HIV-encoding RNA in the biological sample to cDNA; (iii) amplifying a patient-derived segment (PDS) using HIV PCR primers that result in a product comprising the RT gene; (iv) performing sequencing reactions using primers that yield sequences comprising wild type or mutant amino acids at codons 245, 98, 103, 135, 181, and 190; and (v) determining the presence or absence of mutations at codons 245, 98, 103, 135, 181, and 190 from the sequences.

Yet another preferred, non-limiting, specific embodiment of the invention is as follows: A method of assessing the effectiveness of NNRTI therapy of a patient, comprising: (i) collecting a biological sample from an HIV-infected patient; (ii) transcribing the HIV-encoding RNA in the biological sample to cDNA; (iii) amplifying a patient-derived segment (PDS) using HIV PCR primers that result in a product comprising the RT gene; (iv) performing sequencing reactions using primers that yield sequences comprising wild type or mutant amino acids at codons 245, and 103; and (v) determining the presence or absence of mutations at codons 245, and 103 from the sequences.

Yet another preferred, non-limiting, specific embodiment of the invention is as follows: A method of assessing the effectiveness of NNRTI therapy of a patient, comprising: (i) collecting a biological sample from an HIV-infected patient; (ii) transcribing the HIV-encoding RNA in the biological sample to cDNA; (iii) amplifying a patient-derived segment (PDS) using HIV PCR primers that result in a product comprising the RT gene; (iv) performing sequencing reactions using primers that yield sequences comprising wild type or mutant amino acids at codons 245, 103, 135 and 225; and (v) determining the presence or absence of mutations at codons 245, 103, 135 and 225 from the sequences.

Yet another preferred, non-limiting, specific embodiment of the invention is as follows: A method of assessing the effectiveness of NNRTI therapy of a patient, comprising: (i) collecting a biological sample from an HIV-infected patient; (ii) transcribing the HIV-encoding RNA in the biological sample to cDNA; (iii) amplifying a patient-derived segment (PDS) using HIV PCR primers that result in a product comprising the RT gene; (iv) performing sequencing reactions using primers that yield sequences comprising wild type or mutant amino acids at codons 270, 103 and 135; and (v) determining the presence or absence of mutations at codons 270, 103 and 135 from the sequences.

The presence of the mutations at codons 230 and either 103 or 181 of HIV RT indicates that the effectiveness of the current or prospective NNRTI therapy has been diminished. As shown by this invention, a mutation at codon 230, in combination with mutations at either 103 or 181 reduces drug susceptibility, and results in drug-dependent stimulation of viral replication. Using the methods of this invention, change in the NNRTI therapy would be indicated.

Similarly, using the means and methods of this invention the presence of mutations at codons 230, 101, 103, 190, 221, and 238 of the HIV RT gene indicates that the effectiveness of the current or prospective NNRTI therapy has been diminished. As shown by this invention, mutations at codons 230, 101, 103, 190, 221 and 238, reduce drug susceptibility, and result in drug-dependent stimulation of viral replication. Using the methods of this invention, change in the NNRTI therapy would be indicated.

Similarly, using the means and methods of this invention the presence of mutations at codons 241, 103, and 135 of the HIV RT gene indicates that the effectiveness of the current or prospective NNRTI therapy has been diminished. As shown by this invention, mutations at codons 241, 103, and 135 reduce drug susceptibility, and result in drug-dependent stimulation of viral replication. Using the methods of this invention, change in the NNRTI therapy would be indicated.

Similarly, using the means and methods of this invention the presence of mutations at codons 241, 101, 106, 135, 138, and 190 of the HIV RT indicates that the effectiveness of the current or prospective NNRTI therapy has been diminished. As shown by this invention, mutations at codons 241, 101, 106, 135, 138, and 190 reduce drug susceptibility, and result in drug-dependent stimulation of viral replication. Using the methods of this invention, change in the NNRTI therapy would be indicated.

Similarly, using the means and methods of this invention the presence of mutations at codons 245, 98, 135, and 181 of the HIV RT indicates that the effectiveness of the current or prospective NNRTI therapy has been diminished. As shown by this invention, mutations at codons 245, 98, 135, and 181 reduce drug susceptibility, and result in drug-dependent stimulation of viral replication. Using the methods of this invention, change in the NNRTI therapy would be indicated.

Similarly, using the means and methods of this invention the presence of mutations at codons 245, 101, 103, 135, and 190 of the HIV RT indicates that the effectiveness of the current or prospective NNRTI therapy has been diminished. As shown by this invention, mutations at codons 245, 101, 103, 135, and 190 reduce drug susceptibility, and result in drug-dependent stimulation of viral replication. Using the methods of this invention, change in the NNRTI therapy would be indicated.

Similarly, using the means and methods of this invention the presence of mutations at codons 245, 103, 225, and 270 of the HIV RT indicates that the effectiveness of the current or prospective NNRTI therapy has been diminished. As shown by this invention, mutations at codons 245, 103, 225, and 270 reduce drug susceptibility, and result in drug-dependent stimulation of viral replication. Using the methods of this invention, change in the NNRTI therapy would be indicated.

Similarly, using the means and methods of this invention the presence of mutations at codons 245, 135, and 138 of the HIV RT indicates that the effectiveness of the current or prospective NNRTI therapy has been diminished. As shown by this invention, mutations at codons 245, 135, and 138 reduce drug susceptibility, and result in drug-dependent stimulation of viral replication. Using the methods of this invention, change in the NNRTI therapy would be indicated.

Similarly, using the means and methods of this invention the presence of mutations at codons 245, 98, 103, 135, 181, and 190 of the HIV RT indicates that the effectiveness of the current or prospective NNRTI therapy has been diminished. As shown by this invention, mutations at codons 245, 98, 103, 135, 181, and 190 reduce drug susceptibility, and result in drug-dependent stimulation of viral replication. Using the methods of this invention, change in the NNRTI therapy would be indicated.

Similarly, using the means and methods of this invention the presence of mutations at codons 245 and 103 of the HIV RT indicates that the effectiveness of the current or prospective NNRTI therapy has been diminished. As shown by this invention, mutations at codons 245 and 103 reduce drug susceptibility, and result in drug-dependent stimulation of viral replication. Using the methods of this invention, change in the NNRTI therapy would be indicated.

Similarly, using the means and methods of this invention the presence of mutations at codons 245, 103, 135, and 225 of the HIV RT indicates that the effectiveness of the current or prospective NNRTI therapy has been diminished. As shown by this invention, mutations at codons 245, 103, 135, and 225 reduce drug susceptibility, and result in drug-dependent stimulation of viral replication. Using the methods of this invention, change in the NNRTI therapy would be indicated.

Similarly, using the means and methods of this invention the presence of mutations at codons 270, 103, and 135 of the HIV RT indicates that the effectiveness of the current or prospective NNRTI therapy has been diminished. As shown by this invention, mutations at codons 270, 103, and 135 reduce drug susceptibility, and result in drug-dependent stimulation of viral replication. Using the methods of this invention, change in the NNRTI therapy would be indicated.

Another preferred, non-limiting, specific embodiment of the invention is as follows: A method of evaluating the effectiveness of antiretroviral therapy of an HIV-infected patient comprising: (i) collecting a biological sample from an HIV-infected patient; and (ii) determining whether the biological sample comprises nucleic acid encoding the HIV RT gene, and having a mutation at codon 230 and either codon 103 or 181. Using the phenotypic susceptibility assay, it was observed that the presence of mutations at codons 230 and either 103 and 181 correlates positively with decreased susceptibility to delavirdine, nevirapine, and efavirenz and results in drug-dependent stimulation of viral replication. In another specific embodiment, the mutated codon 230 of HIV RT encodes leucine (L), while the mutated codon 103 encodes an asparagine (N). In a still further specific embodiment, the mutated codon 230 or HIV RT encodes leucine (L) and the mutated codon at 181 encodes a cysteine (C).

Yet another preferred, non-limiting, specific embodiment of the invention is as follows: A method of evaluating the effectiveness of antiretroviral therapy of an HIVinfected patient comprising: (i) collecting a biological sample from an HIV-infected patient; and (ii) determining whether the biological sample comprises nucleic acid encoding the HIV RT gene, and having mutations at codons 230, 101, 103, 190, 221, and 238. Using the phenotypic susceptibility assay, it was observed that the presence of mutations at codons 230, 101, 103, 190, 221, and 238 correlates positively with decreased susceptibility to delavirdine, nevirapine, and efavirenz and results in drug-dependent stimulation of viral replication. In another specific embodiment, the mutated codon 230 of HIV RT encodes a leucine (L), the mutated 01 encodes a glutamic acid (E), the mutated codon 103 encodes an asparagine (N), the mutated codon 190 encodes a serine (S), the mutated codon 221 encodes a tyrosine (Y), and the mutated codon 238 encodes a threonine (T).

Yet another preferred, non-limiting, specific embodiment of the invention is as follows: A method of evaluating the effectiveness of antiretroviral therapy of an HIV-infected patient comprising: (i) collecting a biological sample from an HIV-infected patient; and (ii) determining whether the biological sample comprises nucleic acid encoding the HIV RT gene, and having mutations at codons 241, 103, and 135. Using the phenotypic susceptibility assay, it was observed that the presence of mutations at codons 241, 103, and 135 correlates positively with decreased susceptibility to delavirdine, nevirapine, and efavirenz and results in drug-dependent stimulation of viral replication. In another specific embodiment, the mutated codon 241 of HIV RT encodes a serine (S), the mutated codon 103 encodes an asparagine (N), and the mutated codon 135 encodes a threonine (T).

Yet another preferred, non-limiting, specific embodiment of the invention is as follows: A method of evaluating the effectiveness of antiretroviral therapy of an HIV-infected patient comprising: (i) collecting a biological sample from an HIV-infected patient; and (ii) determining whether the biological sample comprises nucleic acid encoding the HIV RT gene, and having mutations at codons 241, 101, 106, 135, 138, and 190. Using the phenotypic susceptibility assay, it was observed that the presence of mutations at codons 241, 101, 106, 135, 138, and 190 correlates positively with decreased susceptibility to delavirdine, nevirapine, and efavirenz and results in drug-dependent stimulation of viral replication. In another specific embodiment, the mutated codon 241 of HIV RT encodes an isoleucine (I), the mutated codon 101 encodes a glutamic acid (E), the mutated codon 106 encodes an methionine (M), the mutated codon 135 encodes a threonine (T), the mutated codon 138 encodes an alanine (A), and the mutated codon 190 encodes an alanine (A).

Yet another preferred, non-limiting, specific embodiment of the invention is as follows: A method of evaluating the effectiveness of antiretroviral therapy of an HIV-infected patient comprising: (i) collecting a biological sample from an HIV-infected patient; and (ii) determining whether the biological sample comprises nucleic acid encoding the HIV RT gene, and having mutations at codons 245, 98, 135, and 181. Using the phenotypic susceptibility assay, it was observed that the presence of mutations at codons 245, 98, 135, and 181 correlates positively with decreased susceptibility to delavirdine, nevirapine, and efavirenz and results in drug-dependent stimulation of viral replication. In another specific embodiment, the mutated codon 245 of HIV RT encodes a glutamic acid (E), the mutated codon 98 encodes a Glycine (G), the mutated codon 135 encodes a threonine (T), and the mutated codon 181 encodes a cysteine (C).

Yet another preferred, non-limiting, specific embodiment of the invention is as follows: A method of evaluating the effectiveness of antiretroviral therapy of an HIV-infected patient comprising: (i) collecting a biological sample from an HIV-infected patient; and (ii) determining whether the biological sample comprises nucleic acid encoding the HIV RT gene, and having mutations at codons 245, 101, 103, 135, and 190. Using the phenotypic susceptibility assay, it was observed that the presence of mutations at codons 245, 101, 103, 135, and 190 correlates positively with decreased susceptibility to delavirdine, nevirapine, and efavirenz and results in drug-dependent stimulation of viral replication. In another specific embodiment, the mutated codon 245 of HIV RT encodes a glutamic acid (E), the mutated codon 101 encodes a glutamic acid (E), the mutated codon 103 encodes asparagine (N), the mutated codon 135 encodes a threonine (T), and the mutated codon 190 encodes an alanine (A).

Yet another preferred, non-limiting, specific embodiment of the invention is as follows: A method of evaluating the effectiveness of antiretroviral therapy of an HIV-infected patient comprising: (i) collecting a biological sample from an HIV-infected patient; and (ii) determining whether the biological sample comprises nucleic acid encoding the HIV RT gene, and having mutations at codons 245, 103, 225, and 270. Using the phenotypic susceptibility assay, it was observed that the presence of mutations at codons 245, 103, 225, and 270 correlates positively with decreased susceptibility to delavirdine, nevirapine, and efavirenz and results in drug-dependent stimulation of viral replication. In another specific embodiment, the mutated codon 245 of HIV RT encodes a glutamic acid (E), the mutated codon 103 encodes asparagine (N), the mutated codon 225 encodes a histidine (H), and the mutated codon 270 encodes a methionine (M).

Yet another preferred, non-limiting, specific embodiment of the invention is as follows: A method of evaluating the effectiveness of antiretroviral therapy of an HIV-infected patient comprising: (i) collecting a biological sample from an HIV-infected patient; and (ii) determining whether the biological sample comprises nucleic acid encoding the HIV RT gene, and having mutations at codons 245, 135, and 138. Using the phenotypic susceptibility assay, it was observed that the presence of mutations at codons 245, 135, and 138 correlates positively with decreased susceptibility to delavirdine, nevirapine, and efavirenz and results in drug-dependent stimulation of viral replication. In another specific embodiment, the mutated codon 245 of HIV RT encodes a threonine (T), the mutated codon 135 encodes a threonine (T), and the mutated codon 138 encodes an glycine (G).

Yet another preferred, non-limiting, specific embodiment of the invention is as follows: A method of evaluating the effectiveness of antiretroviral therapy of an HIV-infected patient comprising: (i) collecting a biological sample from an HIV-infected patient; and (ii) determining whether the biological sample comprises nucleic acid encoding the HIV RT gene, and having mutations at codons 245, 98, 103, 135, 181, and 190. Using the phenotypic susceptibility assay, it was observed that the presence of mutations at codons 245, 98, 103, 135, 181, and 190 correlates positively with decreased susceptibility to delavirdine, nevirapine, and efavirenz and results in drug-dependent stimulation of viral replication. In another specific embodiment, the mutated codon 245 of HIV RT encodes a threonine (T), the mutated codon 98 encodes a glutamic acid (G), the mutated codon 103 encodes a asparagine (N), the mutated codon 135 encodes a threonine (T), the mutated codon 181 encodes a cysteine (C), and the mutated codon 190 encodes an alanine (A).

Yet another preferred, non-limiting, specific embodiment of the invention is as follows: A method of evaluating the effectiveness of antiretroviral therapy of an HIV-infected patient comprising: (i) collecting a biological sample from an HIV-infected patient; and (ii) determining whether the biological sample comprises nucleic acid encoding the HIV RT gene, and having mutations at codons 245 and 103. Using the phenotypic susceptibility assay, it was observed that the presence of mutations at codons 245 and 103 correlates positively with decreased susceptibility to delavirdine, nevirapine, and efavirenz and results in drug-dependent stimulation of viral replication. In another specific embodiment, the mutated codon 245 of HIV RT encodes a threonine (T), and the mutated codon 103 encodes a asparagine (N).

Yet another preferred, non-limiting, specific embodiment of the invention is as follows: A method of evaluating the effectiveness of antiretroviral therapy of an HIV-infected patient comprising: (i) collecting a biological sample from an HIV-infected patient; and (ii) determining whether the biological sample comprises nucleic acid encoding the HIV RT gene, and having mutations at codons 245, 103, 135, and 225. Using the phenotypic susceptibility assay, it was observed that the presence of mutations at codons 245, 103, 135, and 225 correlates positively with decreased susceptibility to delavirdine, nevirapine, and efavirenz and results in drug-dependent stimulation of viral replication. In another specific embodiment, the mutated codon 245 of HIV RT encodes a methionine (M), the mutated codon 103 encodes an asparagine (N), the mutated codon 135 encodes a threonine (T), and the mutated codon 225 encodes a histidine (H).

Yet another preferred, non-limiting, specific embodiment of the invention is as follows: A method of evaluating the effectiveness of antiretroviral therapy of an HIV-infected patient comprising: (i) collecting a biological sample from an HIV-infected patient; and (ii) determining whether the biological sample comprises nucleic acid encoding the HIV RT gene, and having mutations at codons 270, 103, and 135. Using the phenotypic susceptibility assay, it was observed that the presence of mutations at codons 270, 103, and 135 correlates positively with decreased susceptibility to delavirdine, nevirapine, and efavirenz and results in drug-dependent stimulation of viral replication. In another specific embodiment, the mutated codon 270 of HIV RT encodes a serine (S), the mutated codon 103 encodes asparagine (N), and the mutated codon 135 encodes a threonine (T).

This invention also provides the means and methods to use the resistance test vector comprising an HIV gene further comprising an NNRTI mutation for drug screening. More particularly, the invention describes the resistance test vector comprising the HIV reverse transcriptase having mutations at codons 230 and either 103 or 181 for drug screening. The invention also describes the resistance test vector comprising the HIV reverse transcriptase having mutations at codons 230 and 101, 103, 190, 221, and 238. The invention also describes the resistance test vector comprising the HIV reverse transcriptase having mutations at codons 241, 103, and 135. The invention also describes the resistance test vector comprising the HIV reverse transcriptase having mutations at codons 241, 101, 106, 190, 135, and 138. The invention also describes the resistance test vector comprising the HIV reverse transcriptase having mutations at codons 245, 98, 135, and 181. The invention also describes the resistance test vector comprising the HIV reverse transcriptase having mutations at codons 245, 101, 103, 135, and 190. The invention also describes the resistance test vector comprising the HIV reverse transcriptase having mutations at codons 245, 103, 225, and 270. The invention also describes the resistance test vector comprising the HIV reverse transcriptase having mutations at codons 245, 135 and 138. The invention also describes the resistance test vector comprising the HIV reverse transcriptase having mutations at codons 245, 98, 103, 135, 181, and 190. The invention also describes the resistance test vector comprising the HIV reverse transcriptase having mutations at codons 245 and 103. The invention also describes the resistance test vector comprising the HIV reverse transcriptase having mutations at codons 245, 103, 135, and 225. The invention also describes the resistance test vector comprising the HIV reverse transcriptase having mutations at codons 270, 103 and 135.

The structure, life cycle and genetic elements of the viruses which could be tested in the drug susceptibility and resistance test of this invention would be known to one of ordinary skill in the art. It is useful to the practice of this invention, for example, to understand the life cycle of a retrovirus, as well as the viral genes required for retrovirus rescue and infectivity. Retrovirally infected cells shed a membrane virus containing a diploid RNA genome. The virus, studded with an envelope glycoprotein (which serves to determine the host range of infectivity), attaches to a cellular receptor in the plasma membrane of the cell to be infected. After receptor binding, the virus is internalized and uncoated as it passes through the cytoplasm of the host cell. Either on its way to the nucleus or in the nucleus, the reverse transcriptase molecules resident in the viral core drive the synthesis of the double-stranded DNA provirus, a synthesis that is primed by the binding of a tRNA molecule to the genomic viral RNA. The double-stranded DNA provirus is subsequently integrated in the genome of the host cell, where it can serve as a transcriptional template for both mRNAs encoding viral proteins and virion genomic RNA, which will be packaged into viral core particles. On their way out of the infected cell, core particles move through the cytoplasm, attach to the inside of the plasma membrane of the newly infected cell, and bud, taking with them tracts of membrane containing the virally encoded envelope glycoprotein gene product. This cycle of infection-reverse transcription, transcription, translation, virion assembly, and budding-repeats itself over and over again as infection spreads.

The viral RNA and, as a result, the proviral DNA encode several cis-acting elements that are vital to the successful completion of the viral lifecycle. The virion RNA carries the viral promoter at its 3' end. Replicative acrobatics place the viral promoter at the 5' end of the proviral genome as the genome is reverse transcribed. Just 3' to the 5' retroviral LTR lies the viral packaging site. The retroviral lifecycle requires the presence of virally encoded transacting factors. The viral-RNA-dependent DNA polymerase (pol)-reverse transcriptase is also contained within the viral core and is vital to the viral life cycle in that it is responsible for the conversion of the genomic RNA to the integrative intermediate proviral DNA. The viral envelope glycoprotein, env, is required for viral attachment to the uninfected cell and for viral spread. There are also transcriptional trans-activating factors, so called transactivators, that can serve to modulate the level of transcription of the integrated parental provirus. Typically, replication-competent (non-defective) viruses are self-contained in that they encode all of these trans-acting factors. Their defective counterparts are not self-contained.

In the case of a DNA virus, such as a hepadnavirus, understanding the life cycle and viral genes required for infection is useful to the practice of this invention. The process of HPV entry has not been well defined. Replication of HBV uses an RNA intermediate template. In the infected cell the first step in replication is the conversion of the asymmetric relaxed circle DNA (rc-DNA) to covalently closed circle DNA (cccDNA). This process, which occurs within the nucleus of infected liver cells, involves completion of the DNA positive-strand synthesis and ligation of the DNA ends. In the second step, the cccDNA is transcribed by the host RNA polymerase to generate a 3.5 kB RNA template (the pregenome). This pregenome is complexed with protein in the viral core. The third step involves the synthesis of the first negative-sense DNA strand by copying the pregenomic RNA using the virally encoded P protein reverse transcriptase. The P protein also serves as the minus strand DNA primer. Finally, the synthesis of the second positive-sense DNA strand occurs by copying the first DNA strand, using the P protein DNA polymerase activity and an oligomer of viral RNA as primer. The pregenome also transcribes MRNA for the major structural core proteins.

The following flow chart illustrates certain of the various vectors and host cells which may be used in this invention. It is not intended to be all inclusive.

Flow Chart:
Vectors

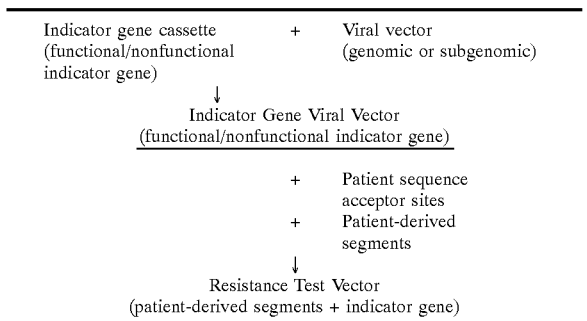

Host Cells

Packaging Host Cell—transfected with packaging expression vectors

Resistance Test Vector Host Cell—a packaging host cell transfected with a resistance test vector Target Host Cell—a host cell to be infected by a resistance test vector viral particle produced by the resistance test vector host cell Resistance Test Vector "Resistance test vector" means one or more vectors which taken together contain DNA or RNA comprising a patient-derived segment and an indicator gene. In the case where the resistance test vector comprises more than one vector the patient-derived segment may be contained in one vector and the indicator gene in a different vector. Such a resistance test vector comprising more than one vector is referred to herein as a resistance test vector system for purposes of clarity but is nevertheless understood to be a resistance test vector. The DNA or RNA of a resistance test vector may thus be contained in one or more DNA or RNA molecules. In one embodiment, the resistance test vector is made by insertion of a patient-derived segment into an indicator gene viral vector. In another embodiment, the resistance test vector is made by insertion of a patient-derived segment into a packaging vector while the indicator gene is contained in a second vector, for example an indicator gene viral vector. As used herein, "patient-derived segment" refers to one or more viral segments obtained directly from a patient using various means, for example, molecular cloning or polymerase chain reaction (PCR) amplification of a population of patient-derived segments using viral DNA or complementary DNA (cDNA) prepared from viral RNA, present in the cells (e.g. peripheral blood mononuclear cells, PBMC), serum or other bodily fluids of infected patients. When a viral segment is "obtained directly" from a patient it is obtained without passage of the virus through culture, or if the virus is cultured, then by a minimum number of passages to essentially eliminate the selection of mutations in culture. The term "viral segment" refers to any functional viral sequence or viral gene encoding a gene product (e.g., a protein) that is the target of an anti-viral drug. The term "functional viral sequence" as used herein refers to any nucleic acid sequence (DNA or RNA) with functional activity such as enhancers, promoters, polyadenylation sites, sites of action of trans-acting factors, such as tar and RRE, packaging sequences, integration sequences, or splicing sequences. If a drug were to target more than one functional viral sequence or viral gene product then patient-derived segments corresponding to each said viral gene would be inserted in the resistance test vector. In the case of combination therapy where two or more anti-virals targeting two different functional viral sequences or viral gene products are being evaluated, patient-derived segments corresponding to each functional viral sequence or viral gene product would be inserted in the resistance test vector. The patient-derived segments are inserted into unique restriction sites or specified locations, called patient sequence acceptor sites, in the indicator gene viral vector or for example, a packaging vector depending on the particular construction being used as described herein.

As used herein, "patient-derived segment" encompasses segments derived from human and various animal species. Such species include, but are not limited to chimpanzees, horses, cattles, cats and dogs.

Patient-derived segments can also be incorporated into resistance test vectors using any of several alternative cloning techniques. For example, cloning via the introduction of class II restriction sites into both the plasmid backbone and the patient-derived segments or by uracil DNA glycosylase primer cloning (refs).

The patient-derived segment may be obtained by any method of molecular cloning or gene amplification, or modifications thereof, by introducing patient sequence acceptor sites, as described below, at the ends of the patient-derived segment to be introduced into the resistance test vector. For example, in a gene amplification method such as PCR, restriction sites corresponding to the patient-sequence acceptor sites can be incorporated at the ends of the primers used in the PCR reaction. Similarly, in a molecular cloning method such as cDNA cloning, said restriction sites can be incorporated at the ends of the primers used for first or second strand cDNA synthesis, or in a method such as primer-repair of DNA, whether cloned or uncloned DNA, said restriction sites can be incorporated into the primers used for the repair reaction. The patient sequence acceptor sites and primers are designed to improve the representation of patient-derived segments. Sets of resistance test vectors having designed patient sequence acceptor sites provide representation of patient-derived segments that would be underrepresented in one resistance test vector alone.

Resistance test vectors are prepared by modifying an indicator gene viral vector (described below) by introducing patient sequence acceptor sites, amplifying or cloning patient-derived segments and inserting the amplified or cloned sequences precisely into indicator gene viral vectors at the patient sequence acceptor sites. The resistance test vectors are constructed from indicator gene viral vectors which are in turn derived from genomic viral vectors or subgenomic viral vectors and an indicator gene cassette, each of which is described below. Resistance test vectors are then introduced into a host cell. Alternatively, a resistance test vector (also referred to as a resistance test vector system) is prepared by introducing patient sequence acceptor sites into a packaging vector, amplifying or cloning patient-derived segments and inserting the amplified or cloned sequences precisely into the packaging vector at the patient sequence acceptor sites and co-transfecting this packaging vector with an indicator gene viral vector.

In one preferred embodiment, the resistance test vector may be introduced into packaging host cells together with packaging expression vectors, as defined below, to produce resistance test vector viral particles that are used in drug resistance and susceptibility tests that are referred to herein as a "particle-based test." In an alternative preferred embodiment, the resistance test vector may be introduced into a host cell in the absence of packaging expression vectors to carry out a drug resistance and susceptibility test that is referred to herein as a "non-particle-based test." As used herein a "packaging expression vector" provides the factors, such as packaging proteins (e.g. structural proteins such as core and envelope polypeptides), transacting factors, or genes required by replication-defective retrovirus or hepadnavirus. In such a situation, a replication-competent viral genome is enfeebled in a manner such that it cannot replicate on its own. This means that, although the packaging expression vector can produce the trans-acting or missing genes required to rescue a defective viral genome present in a cell containing the enfeebled genome, the enfeebled genome cannot rescue itself.

Indicator or Indicator Gene

"Indicator or indicator gene" refers to a nucleic acid encoding a protein, DNA or RNA structure that either directly or through a reaction gives rise to a measurable or noticeable aspect, e.g. a color or light of a measurable wavelength or in the case of DNA or RNA used as an indicator a change or generation of a specific DNA or RNA structure. Preferred examples of an indicator gene is the *E. coli* lacZ gene which encodes beta-galactosidase, the luc gene which encodes luciferase either from, for example, *Photonis pyralis* (the firefly) or *Renilia reniformis* (the sea pansy), the *E. coli* phoA gene which encodes alkaline phosphatase, green fluorescent protein and the bacterial CAT gene which encodes chloramphenicol acetyltransferase. Additional preferred examples of an indicator gene are secreted proteins or cell surface proteins that are readily measured by assay, such as radioimmunoassay (RIA), or fluorescent activated cell sorting (FACS), including, for example, growth factors, cytokines and cell surface antigens (e.g. growth hormone, Il-2 or CD4, respectively). "Indicator gene" is understood to also include a selection gene, also referred to as a selectable marker. Examples of suitable selectable markers for mammalian cells are dihydrofolate reductase (DHFR), thymidine kinase, hygromycin, neomycin, zeocin or *E. coli* gpt. In the case of the foregoing examples of indicator genes, the indicator gene and the patient-derived segment are discrete, i.e. distinct and separate genes. In some cases a patient-derived segment may also be used as an indicator gene. In one such embodiment in which the patient-derived segment corresponds to more than one viral gene which is the target of an anti-viral, one of said viral genes may also serve as the indicator gene. For example, a viral protease gene may serve as an indicator gene by virtue of its ability to cleave a chromogenic substrate or its ability to activate an inactive zymogen which in turn cleaves a chromogenic substrate, giving rise in each case to a color reaction. In all of the above examples of indicator genes, the indicator gene may be either "functional" or "non-functional" but in each case the expression of the indicator gene in the target cell is ultimately dependent upon the action of the patient-derived segment.

Functional Indicator Gene

In the case of a "functional indicator gene" the indicator gene may be capable of being expressed in a "packaging host cell/resistance test vector host cell" as defined below, independent of the patient-derived segment, however the functional indicator gene could not be expressed in the target host cell, as defined below, without the production of functional resistance test vector particles and their effective infection of the target host cell. In one embodiment of a functional indicator gene, the indicator gene cassette, comprising control elements and a gene encoding an indicator protein, is inserted into the indicator gene viral vector with the same or opposite transcriptional orientation as the native or foreign enhancer/promoter of the viral vector. One example of a functional indicator gene in the case of HIV or HBV, places the indicator gene and its promoter (a CMV IE enhancer/promoter) in the same or opposite transcriptional orientation as the HIV-LTR or HBV enhancer-promoter, respectively, or the CMV IE enhancer/promoter associated with the viral vector.

Non-Functional Indicator Gene

Alternatively the indicator gene, may be "non-functional" in that the indicator gene is not efficiently expressed in a packaging host cell transfected with the resistance test vector, which is then referred to a resistance test vector host cell, until it is converted into a functional indicator gene through the action of one or more of the patient-derived segment products. An indicator gene is rendered non-functional through genetic manipulation according to this invention.

1. Permuted Promoter

In one embodiment an indicator gene is rendered non-functional due to the location of the promoter, in that, although the promoter is in the same transcriptional orientation as the indicator gene, it follows rather than precedes the indicator gene coding sequence. This misplaced promoter is referred to as a "permuted promoter." In addition to the permuted promoter the orientation of the non-functional indicator gene is opposite to that of the native or foreign promoter/enhancer of the viral vector. Thus the coding sequence of the non-functional indicator gene can neither be transcribed by the permuted promoter nor by the viral promoters. The non-functional indicator gene and its permuted promoter is rendered functional by the action of one or more of the viral proteins. One example of a non-functional indicator gene with a permuted promoter in the case of HIV, places a T7 phage RNA polymerase promoter (herein referred to as T7 promoter) promoter in the 5' LTR in the same transcriptional orientation as the indicator gene. The indicator gene cannot be transcribed by the T7 promoter as the indicator gene cassette is positioned upstream of the T7 promoter. The non-functional indicator gene in the resistance test vector is converted into a functional indicator gene by reverse transcriptase upon infection of the target cells, resulting from the repositioning of the T7 promoter, by copying from the 5' LTR to the 3' LTR, relative to the indicator gene coding region. Following the integration of the repaired indicator gene into the target cell chromosome by HIV integrase, a nuclear T7 RNA polymerase expressed by the target cell transcribes the indicator gene. One example of a non-functional indicator gene with a permuted promoter in the case of HBV, places an enhancer-promoter region downstream or 3' of the indicator gene both having the same transcriptional orientation. The indicator gene cannot be transcribed by the enhancer-promoter as the indicator gene cassette is positioned upstream. The non-functional indicator gene in the resistance test vector is converted into a functional indicator gene by reverse transcription and circularization of the HBV indicator gene viral vector by the repositioning of the enhancer-promoter upstream relative to the indicator gene coding region.

A permuted promoter may be any eukaryotic or prokaryotic promoter which can be transcribed in the target host cell. Preferably the promoter will be small in size to enable insertion in the viral genome without disturbing viral replication. More preferably, a promoter that is small in size and is capable of transcription by a single subunit RNA polymerase introduced into the target host cell, such as a bacteriophage promoter, will be used. Examples of such bacteriophage promoters and their cognate RNA polymerases include those of phages T7, T3 and Sp6. A nuclear localization sequence (NLS) may be attached to the RNA polymerase to localize expression of the RNA polymerase to the nucleus where they may be needed to transcribed the repaired indicator gene. Such an NLS may be obtained from any nuclear-transported protein such as the SV40 T antigen. If a phage RNA polymerase is employed, an internal ribosome entry site (IRES) such as the EMC virus 5' untranslated region (UTR) may be added in front of the indicator gene, for translation of the transcripts which are generally uncapped. In the case of HIV, the permuted promoter itself can be introduced at any position within the 5' LTR that is copied to the 3' LTR during reverse transcription so long as LTR function is not disrupted, preferably within the U5 and R portions of the LTR, and most preferably outside of functionally important and highly conserved regions of U5 and R. In the case of HBV, the permuted promoter can be placed at any position that does not disrupt the cis acting elements that are necessary for HBV DNA replication. Blocking sequences may be added at the ends of the resistance test vector should there be inappropriate expression of the non-functional indicator gene due to transfection artifacts (DNA concatenation). In the HIV example of the permuted T7 promoter given above, such a blocking sequence may consist of a T7 transcriptional terminator, positioned to block readthrough transcription resulting from DNA concatenation, but not transcription resulting from repositioning of the permuted T7 promoter from the 5' LTR to the 3' LTR during reverse transcription.

2. Permuted Coding Region

In a second embodiment, an indicator gene is rendered non-functional due to the relative location of the 5' and 3' coding regions of the indicator gene, in that, the 3' coding region precedes rather than follows the 5' coding region. This misplaced coding region is referred to as a "permuted coding region." The orientation of the non-functional indicator gene may be the same or opposite to that of the native or foreign promoter/enhancer of the viral vector, as MFNA coding for a functional indicator gene will be produced in the event of either orientation. The non-functional indicator gene and its permuted coding region is rendered functional by the action of one or more of the patient-derived segment products. A second example of a non-functional indicator gene with a permuted coding region in the case of HIV, places a 5' indicator gene coding region with an associated promoter in the 3' LTR U3 region and a 3' indicator gene coding region in an upstream location of the HIV genome, with each coding region having the same transcriptional orientation as the viral LTRs. In both examples, the 5' and 3' coding regions may also have associated splice donor and acceptor sequences, respectively, which may be heterologous or artificial splicing signals. The indicator gene cannot be functionally transcribed either by the associated promoter or viral promoters, as the permuted coding region prevents the formation of functionally spliced transcripts. The non-functional indicator gene in the resistance test vector is converted into a functional indicator gene by reverse transcriptase upon infection of the target cells, resulting from the repositioning of the 5' and 3' indicator gene coding regions relative to one another, by copying of the 3' LTR to the 5' LTR. Following transcription by the promoter associated with the 5' coding region, RNA splicing can join the 5' and 3' coding regions to produce a functional indicator gene product. One example of a non-functional indicator gene with a permuted coding region in the case of HBV, places a 3' indicator gene coding region upstream or 5' of the enhancer-promoter and the 5' coding region of the indicator gene. The transcriptional orientation of the indicator gene 5' and 3' coding regions are identical to one another, and the same as that of the indicator gene viral vector. However, as the indicator gene 5' and 3' coding regions are permuted in the resistance test vectors (i.e., the 5' coding region is downstream of the 3' coding region), no mRNA is transcribed which can be spliced to generate a functional indicator gene coding region. Following reverse transcription and circularization of the indicator gene viral vector, the indicator gene 3' coding region is positioned downstream or 3' to the enhancer-promoter and 5' coding regions thus permitting the transcription of mRNA which can be spliced to generate a functional indicator gene coding region.

3. Inverted Intron

In a third embodiment, the indicator gene is rendered non-functional through use of an "inverted intron," i.e. an intron inserted into the coding sequence of the indicator gene with a transcriptional orientation opposite to that of the indicator gene. The overall transcriptional orientation of the indicator gene cassette including its own, linked promoter, is opposite to that of the viral control elements, while the orientation of the artificial intron is the same as the viral control elements. Transcription of the indicator gene by its own linked promoter does not lead to the production of functional transcripts as the inverted intron cannot be spliced in this orientation. Transcription of the indicator gene by the viral control elements does, however, lead to the removal of the inverted intron by RNA splicing, although the indicator gene is still not functionally expressed as the resulting transcript has an antisense orientation. Following the reverse transcription of this transcript and integration of the resultant retroviral DNA, or the circularization of hepadnavirus DNA, the indicator gene can be functionally transcribed using its own linked promoter as the inverted intron has been previously removed. In this case, the indicator gene itself may contain its own functional promoter with the entire transcriptional unit oriented opposite to the viral control elements. Thus the non-functional indicator gene is in the wrong orientation to be transcribed by the viral control elements and it cannot be functionally transcribed by its own promoter, as the inverted intron cannot be properly excised by splicing. However, in the case of a retrovirus and HIV specifically and hepadnaviruses, and HBV specifically, transcription by the viral promoters (HIV LTR or HBV enhancer-promoter) results in the removal of the inverted intron by splicing. As a consequence of reverse transcription of the resulting spliced transcript and the integration of the resulting provirus into the host cell chromosome or circularization of the HBV vector, the indicator gene can now be functionally transcribed by its own promoter. The inverted intron, consisting of a splice donor and acceptor site to remove the intron, is preferably located in the coding region of the indicator gene in order to disrupt translation of the indicator gene. The splice donor and acceptor may be any splice donor and acceptor. A preferred splice donor-receptor is the CMV IE splice donor and the splice acceptor of the second exon of the human alpha globin gene ("intron A").

Indicator Gene Viral Vector—Construction

As used herein, "indicator gene viral vector" refers to a vector(s) comprising an indicator gene and its control elements and one or more viral genes. The indicator gene viral vector is assembled from an indicator gene cassette and a "viral vector," defined below. The indicator gene viral vector may additionally include an enhancer, splicing signals, polyadenylation sequences, transcriptional terminators, or other regulatory sequences. Additionally the indicator gene viral vector may be functional or nonfunctional. In the event that the viral segments which are the target of the anti-viral drug are not included in the indicator gene viral vector they are provided in a second vector. An "indicator gene cassette" comprises an indicator gene and control elements. "Viral vector" refers to a vector comprising some or all of the following: viral genes encoding a gene product, control sequences, viral packaging sequences, and in the case of a retrovirus, integration sequences. The viral vector may additionally include one or more viral segments one or more of which may be the target of an anti-viral drug. Two examples of a viral vector which contain viral genes are referred to herein as an "genomic viral vector" and a "subgenomic viral vector." A "genomic viral vector" is a vector which may comprise a deletion of a one or more viral genes to render the virus replication incompetent, but which otherwise preserves the mRNA expression and processing characteristics of the complete virus. In one embodiment for an HIV drug susceptibility and resistance test, the genomic viral vector comprises the HIV gag-pol, vif, vpr, tat, rev, vpu, and nef genes (some, most or all of env may be deleted). A "subgenomic viral vector" refers to a vector comprising the coding region of one or more viral genes which may encode the proteins that are the target(s) of the anti-viral drug. In the case of HIV, a preferred embodiment is a subgenomic viral vector comprising the HIV gag-pol gene. In the case of HBV a preferred embodiment is a subgenomic viral vector comprising the HBV P gene. In the case of HIV, two examples of proviral clones used for viral vector construction are: HXB2 (Fisher et al., (1986) Nature, 320, 367–371) and NL4-3, (Adachi et al., (1986) J. Virol., 59, 284–291). In the case of HBV, a large number of full length genomic sequences have been characterized and could be used for construction of HBV viral vectors: GenBank Nos. M54923, M38636, J02203 and X59795. The viral coding genes may be under the control of a native enhancer/promoter or a foreign viral or cellular enhancer/promoter. A preferred embodiment for an HIV drug susceptibility and resistance test, is to place the genomic or subgenomic viral coding regions under the control of the native enhancer/promoter of the HIV-LTR U3 region or the CMV immediate-early (IE) enhancer/promoter. A preferred embodiment for an HBV drug susceptibility and resistance test, is to place the genomic or subgenomic viral coding regions under the control of the CMV immediate-early (IE) enhancer/promoter. In the case of an indicator gene viral vector that contains one or more viral genes which are the targets or encode proteins which are the targets of an anti-viral drug(s) then said vector contains the patient sequence acceptor sites. The patient-derived segments are inserted in the patient sequence acceptor site in the indicator gene viral vector which is then referred to as the resistance test vector, as described above.

"Patient sequence acceptor sites" are sites in a vector for insertion of patient-derived segments and said sites may be: 1) unique restriction sites introduced by site-directed mutagenesis into a vector; 2) naturally occurring unique restriction sites in the vector; or 3) selected sites into which a patient-derived segment may be inserted using alternative cloning methods (e.g. UDG cloning). In one embodiment the patient sequence acceptor site is introduced into the indicator gene viral vector. The patient sequence acceptor sites are preferably located within or near the coding region of the viral protein which is the target of the anti-viral drug. The viral sequences used for the introduction of patient sequence acceptor sites are preferably chosen so that no change, or a conservative change, is made in the amino acid coding sequence found at that position. Preferably the patient sequence acceptor sites are located within a relatively conserved region of the viral genome to facilitate introduction of the patient-derived segments. Alternatively, the patient sequence acceptor sites are located between functionally important genes or regulatory sequences. Patient-sequence acceptor sites may be located at or near regions in the viral genome that are relatively conserved to permit priming by the primer used to introduce the corresponding restriction site into the patient-derived segment. To improve the representation of patient-derived segments further, such primers may be designed as degenerate pools to accommodate viral sequence heterogeneity, or may incorporate residues such as deoxyinosine (I) which have multiple base-pairing capabilities. Sets of resistance test vectors having patient sequence acceptor sites that define the same or overlapping restriction site intervals may be used together in the drug resistance and susceptibility tests to provide representation of patient-derived segments that contain internal restriction sites identical to a given patient sequence acceptor site, and would thus be underrepresented in either resistance test vector alone.

Host Cells

The resistance test vector is introduced into a host cell. Suitable host cells are mammalian cells. Preferred host cells are derived from human tissues and cells which are the principle targets of viral infection. In the case of HIV these include human cells such as human T cells, monocytes, macrophage, dendritic cells, Langerhans cells, hematopoeitic stem cells or precursor cells, and other cells. In the case of HPV, suitable host cells include hepatoma cell lines (HepG2, Huh 7) primary human hepatocytes, mammalian cells which can beinfected by pseudotyped HBV, and other cells. Human derived host cells will assure that the anti-viral drug will enter the cell efficiently and be converted by the cellular enzymatic machinery into the metabolically relevant form of the anti-viral inhibitor. Host cells are referred to herein as a "packaging host cells," "resistance test vector host cells," or "target host cells." A "packaging host cell" refers to a host cell that provides the trans-acting factors and viral packaging proteins required by the replication defective viral vectors used herein, such as the resistance test vectors, to produce resistance test vector viral particles. The packaging proteins may be provided for by the expression of viral genes contained within the resistance test vector itself, a packaging expression vector(s), or both. A packaging host cell is a host cell which is transfected with one or more packaging expression vectors and when transfected with a resistance test vector is then referred to herein as a "resistance test vector host cell" and is sometimes referred to as a packaging host cell/resistance test vector host cell. Preferred host cells for use as packaging host cells for HIV include 293 human embryonic kidney cells (293, Graham, F. L. et al., J. Gen Virol. 36: 59, 1977), BOSC23 (Pear et al., Proc. Natl. Acad. Sci. 90, 8392, 1993), tsa54 and tsa201 cell lines (Heinzel et al., J. Virol. 62, 3738,1988), for HBV HepG2 (Galle and Theilmann, L. Arzheim.-Forschy Drug Res. (1990) 40, 1380–1382). (Huh, Ueda, K et al. Virology *1989) 169, 213–216). A "target host cell" refers to a cell to be infected by resistance test vector viral particles produced by the resistance test vector host cell in which expression or inhibition of the indicator gene takes place. Preferred host cells for use as target host cells include human T cell leukemia cell lines including Jurkat (ATCC T1B-152), H9 (ATCC HTB-176), CEM (ATCC CCL-119), HUT78 (ATCC T1B-161), and derivatives thereof.

This invention is illustrated in the Experimental Details section which follows. These sections are set forth to aid in an understanding of the invention but are not intended to, and should not be construed to, limit in any way the invention as set forth in the claims which follow thereafter.

EXPERIMENTAL DETAILS

EXAMPLE 1

Phenotypic Drug Susceptibility and Resistance Test Using Resistance Test Vectors Phenotypic drug susceptibility and resistance tests are carried out using the means and methods described in PCT International Application No. PCT/US97/01609, filed Jan. 29, 1997 which is hereby incorporated by reference.

In these experiments patient-derived segment (PDS) corresponding to the HIV protease(PR) and reverse transcriptase coding regions were either patient-derived segments amplified by the reverse transcription-polymerase chain reaction method (RT-PCR) using viral RNA isolated from viral particles present in the serum of HIV-infected individuals or were mutants of wild type HIV-1 made by site directed mutagenesis of a parental clone of resistance test vector DNA. Isolation of viral RNA was performed using standard procedures (e.g. RNAgents Total RNA Isolation System, Promega, Madison Wis. or RNAzol, Tel-Test, Friendswood, Tex.). The RT-PCR protocol was divided into two steps. A retroviral reverse transcriptase [e.g. Moloney MuLV reverse transcriptase (Roche Molecular Systems, Inc., Branchburg, N.J.), or avian myeloblastosis virus (AMV) reverse transcriptase, (Boehringer Mannheim, Indianapolis, Ind.)] was used to transcribe viral RNA into cDNA. The cDNA was then amplified using a thermostable DNA polymerase [e.g. Taq (Roche Molecular Systems, Inc., Branchburg, N.J.), Tth (Roche Molecular Systems, Inc., Branchburg, N.J.), PrimeZyme (isolated from *Thermus brockianus*, Biometra, Gottingen, Germany)] or a combination of thermostable polymerases as described for the performance of "long PCR" (Barnes, W. M., (1994) Proc. Natl. Acad. Sci, USA 91, 2216–2220) [e.g. Expand High Fidelity PCR System (Taq+Pwo), (Boehringer Mannheim. Indianapolis, Ind.) OR GeneAmp XL PCR kit (Tth+Vent), (Roche Molecular Systems, Inc., Branchburg, N.J.)].

The primers, ApaI primer (PDSApa) and AgeI primer (PDSAge), used to amplify the "test" patient-derived segments contained sequences resulting in ApaI and AgeI recognition sites being introduced into the 5' and 3' termini of the PCR product, respectively as described in PCT International Application No. PCT/US97/01609, filed Jan. 29, 1997.

Resistance test vectors incorporating the "test" patient-derived segments were constructed as described in PCT International Application No. PCT/US97/01609, filed Jan. 29, 1997, using an amplified DNA product of 1.5 kB prepared by RT-PCR using viral RNA as a template and oligonucleotides PDSApa (1) and PDSAge (2) as primers, followed by digestion with ApaI and AgeI)or the isoschizimer PINAI.) To ensure that the plasmid DNA corresponding to the resultant resistance test vector comprises a representative sample of the HIV viral quasi-species present in the serum of a given patient, many (>100) independent *E. coli* transformants obtained in the construction of a given resistance test vector were pooled and used for the preparation of plasmid DNA.

A packaging expression vector encoding an amphotrophic MuLV 4070A env gene product enables production in a resistance test vector host cell of resistance test vector viral particles which can efficiently infect human target cells. Resistance test vectors encoding all HIV genes with the exception of env were used to transfect a packaging host cell (once transfected, the host cell is referred to as a "resistance test vector host cell"). The packaging expression vector which encodes the amphotrophic MuLV 4070A env gene product is used with the resistance test vector to enable production in the resistance test vector host cell of infectious pseudotyped resistance test vector viral particles.

Resistance tests performed with resistance test vectors were carried out using packaging host and target host cells consisting of the human embryonic kidney cell line 293 (Cell Culture Facility, UC San Francisco, SF, Calif.) or the Jurkat leukemic T-cell line (Arthur Weiss, UC San Francisco, SF, Calif.).

Resistance tests were carried out with resistance test vectors using two host cell types. Resistance test vector viral particles were produced by a first host cell (the resistance test vector host cell) that was prepared by transfecting a packaging host cell with the resistance test vector and the packaging expression vector. The resistance test vector viral particles were then used to infect a second host cell (the target host cell) in which the expression of the indicator gene is measured.

The resistance test vectors containing a functional luciferase gene cassette were constructed and host cells were transfected with the resistance test vector DNA. The resistant test vectors contained patient-derived reverse transcriptase and protease sequences that were either susceptible or resistant to the antiretroviral agents, such as nucleoside reverse transcriptase inhibitors, (NRTIs) non-nucleoside reverse transcriptase inhibitors (NRTIs) and protease inhibitors. The resistance test vector viral particles produced by transfecting the resistance test vector DNA into host cells, either in the presence or absence of PRIs, were used to infect target host cells grown either in the absence of NRTIs or NNRTIs, or in the presence of increasing concentrations of the drug. The amount of luciferase activity produced in infected target host cells in the presence of varying concentrations of drug was compared to the amount of luciferase produced in infected target host cells in the absence of drug. "Drug resistance" was measured as the amount of drug required to inhibit by 50% the luciferase activity detected in the absence of drug (inhibitory concentration 50%, IC50). The IC50 values were determined by plotting percent drug inhibition vs. log10 drug concentration. Stimulation of viral replication was measured as the percent increase in luciferase activity detected when infection occurs in the presence of drug as compared to in the absence of drug.

Figure 3:
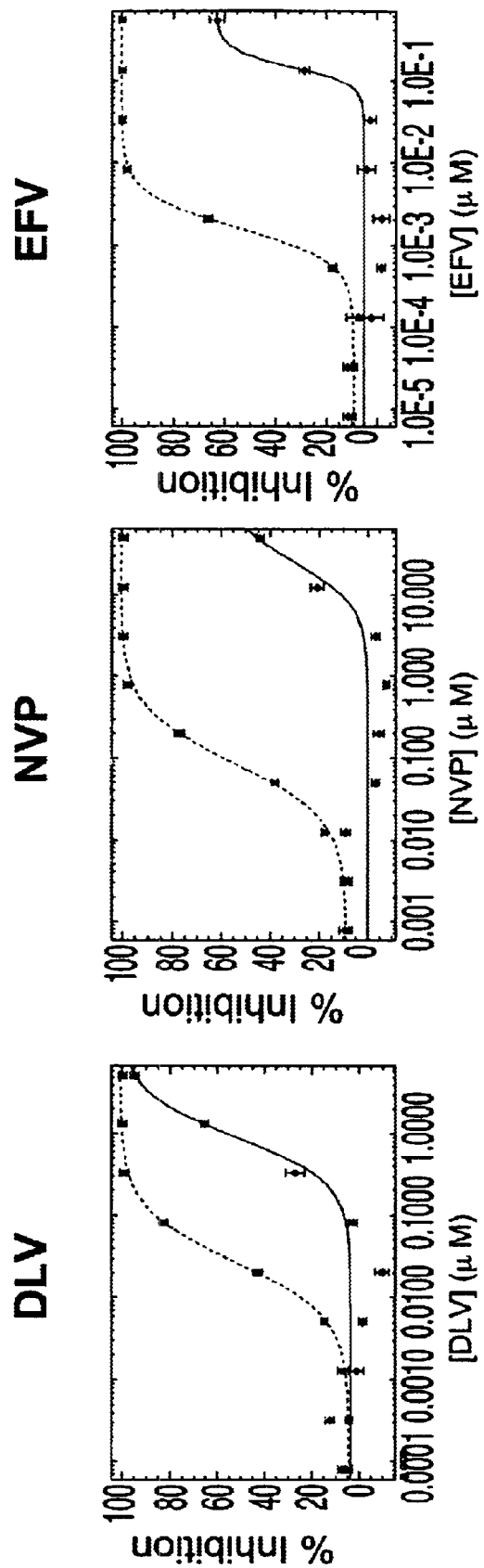
FIG. 3. Examples of phenotypic drug susceptibility profiles. Data are analyzed by plotting the percent inhibition of luciferase activity vs. $\log_{10}$ drug concentration. This plot is used to calculate the drug concentration that are required to inhibit virus replication by 50% ($IC_{50}$) and by 95% ($IC_{95}$). Shifts in the inhibition curves towards higher drug concentrations are interpreted as evidence of decreased drug susceptibility, ("drug resistance"). Three typical curves for the NNRTI's delavirdine (DLV), nevirapine (NVP) and efavirenz (EFV) are shown. A reduction in drug susceptibility (or "increased resistance") manifests as a shift in the drug susceptibility curve toward higher drug concentrations (to the right) as compared to a baseline (pre-treatment) sample, or as compared to a drug susceptible virus control, such as PNL4-3 or HXB-2.
Figure 4:
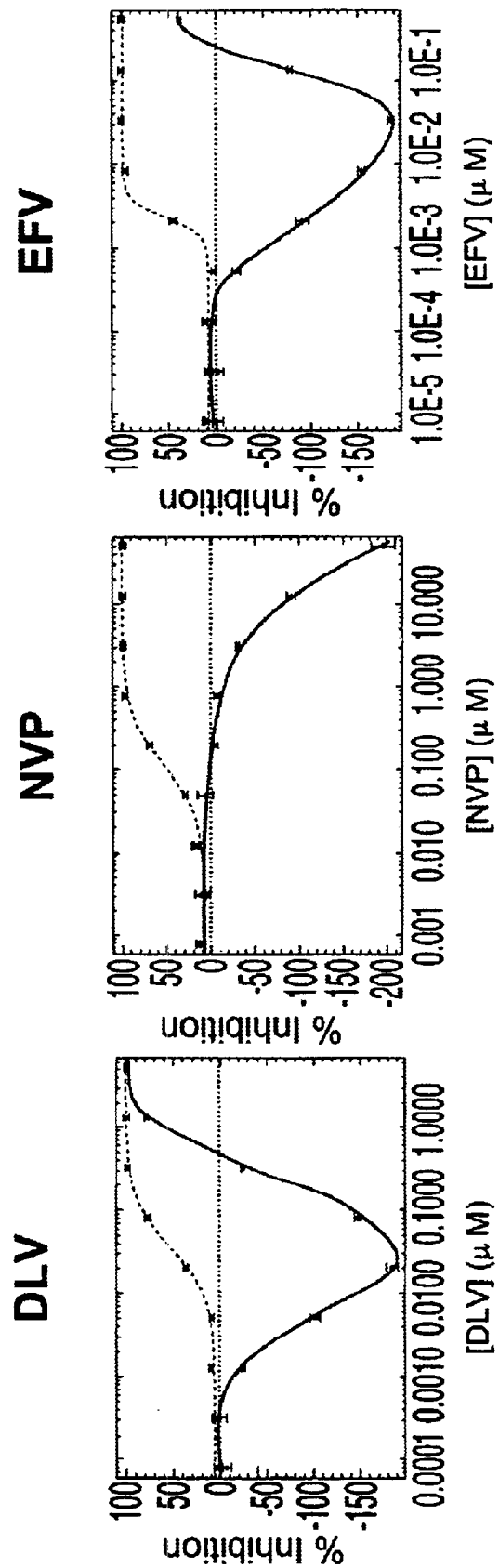
FIG. 4. Examples of phenotypic drug susceptibility profiles showing drug-dependent stimulation of viral replication. Data are analyzed by plotting the percent inhibition of luciferase activity vs. $\log_{10}$ drug concentration. This plot is used to calculate the drug concentration that are required to inhibit virus replication by 50% ($IC_{50}$) and by 95% ($IC_{95}$). In these graphs, stimulation of viral replication manifests as percent inhibition less than zero (i.e. negative inhibition). Three typical curves showing drug-dependent stimulation of viral replication in the presence of the NNRTI's delavirdine (DLV), nevirapine (NVP) and efavirenz (EFV) are shown. The results obtained from the patientderived or site-directed mutant resistance test vectors are compared to results obtained from a drug susceptible virus control, such as PNL4-3 or HXB-2.
Figure 6:
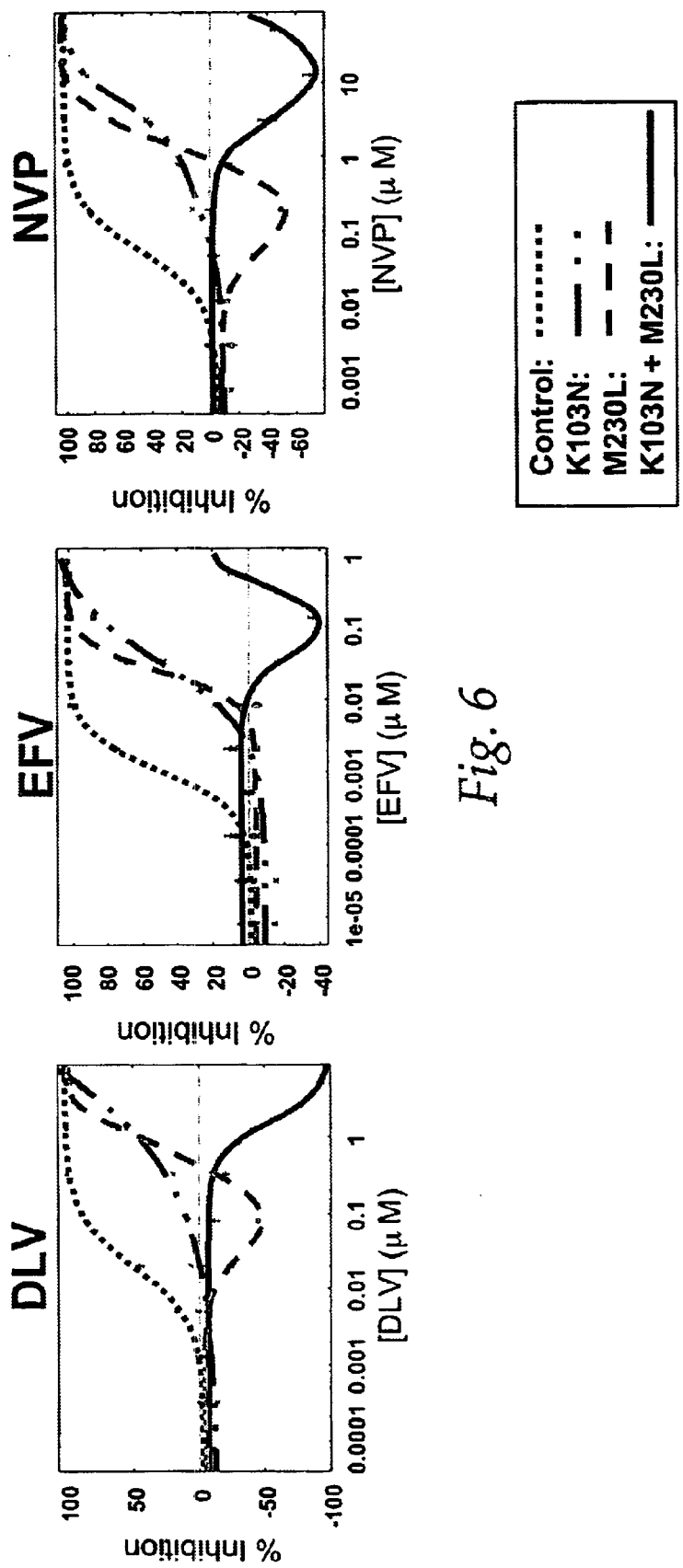
FIG. 6. Reduced susceptibility and drug-dependent stimulation of viral replication of three site-directed mutants: K103N, M230L, and K103N combined with K230L, as described in Example 4. The results from each sitedirected mutant are compared to each other, as well as to those results obtained from a drug susceptible virus control, such as PNL4-3, or HXB-2. In these graphs, stimulation of viral replication manifests as percent inhibition less than zero (i.e. negative inhibition).
Figure 7:
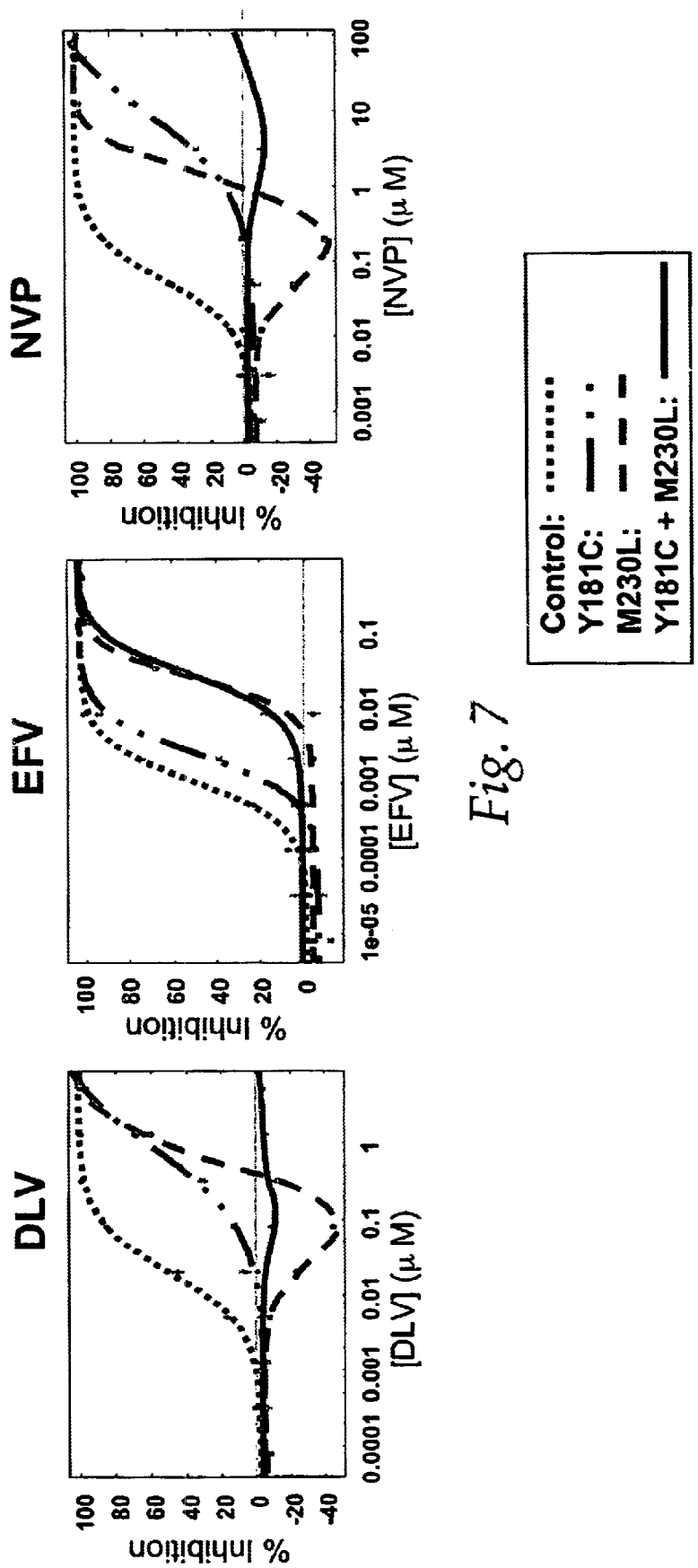
FIG. 7. Reduced susceptibility and drug-dependent stimulation of viral replication for three site-directed mutants: Y181C, M230L, and Y181C combined with K230L, as described in Example 3. The results from each sitedirected mutant for each NNRTI (delavirdine, efavirenz, and nevirapine) are compared to each other, as well as to those results obtained from a drug susceptible virus control, such as PNL4-3, or HXB-2. In these graphs, stimulation of viral replication manifests as percent inhibition less than zero (i.e. negative inhibition).
Figure 8:
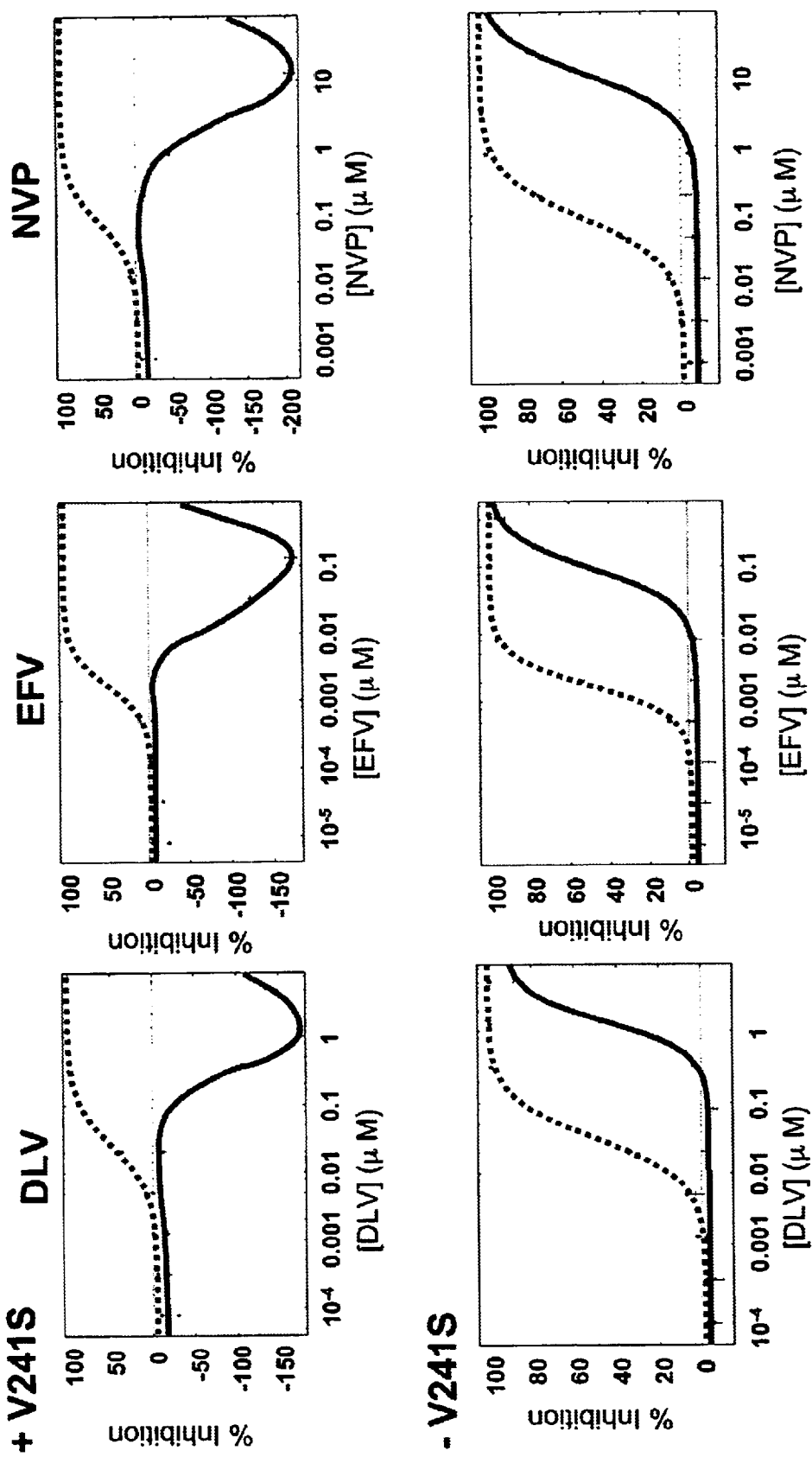
FIG. 8. Reverse mutagenesis of HIV RT codon positions 241 and 277 in Patient 11073, as described in Example 6. The top panel of the figure shows the graphs from the patient sample, which contains the V241S mutation. In these graphs, stimulation of viral replication manifests as percent inhibition less than zero (i.e. negative inhibition) for all three NNRTIs (delavirdine, efavirenz, and nevirapine). The bottom panel shows the results of site-directed reversion of the mutation to 241V. In this graph, there is no longer negative inhibition (stimulation of viral replication) in any of the three NNRTIs (delavirdine, efavirenz, or nevirapine).
Figure 9:
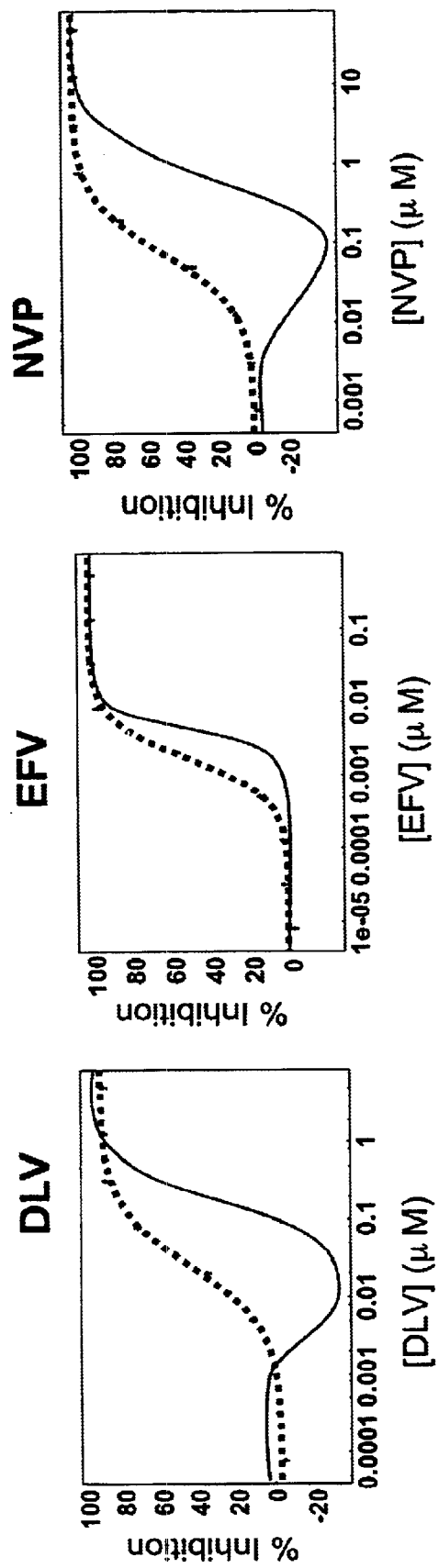
FIG. 9. Susceptibility curves of two time-points separated by 32 weeks in the course of therapy of Patient 014451, as described in Example 7. The top panel of the figure shows susceptibility curves from patient sample 014459, (week 0). The bottom panel shows susceptibility curves from patient sample 014451, (week 32), which show both reduced susceptibility as well as drug-dependent stimulation of viral replication in the presence of all three NNRTIs, which coincides with the emergence of HIV RT mutations at codons 101, 106, and 190.
Figure 10:
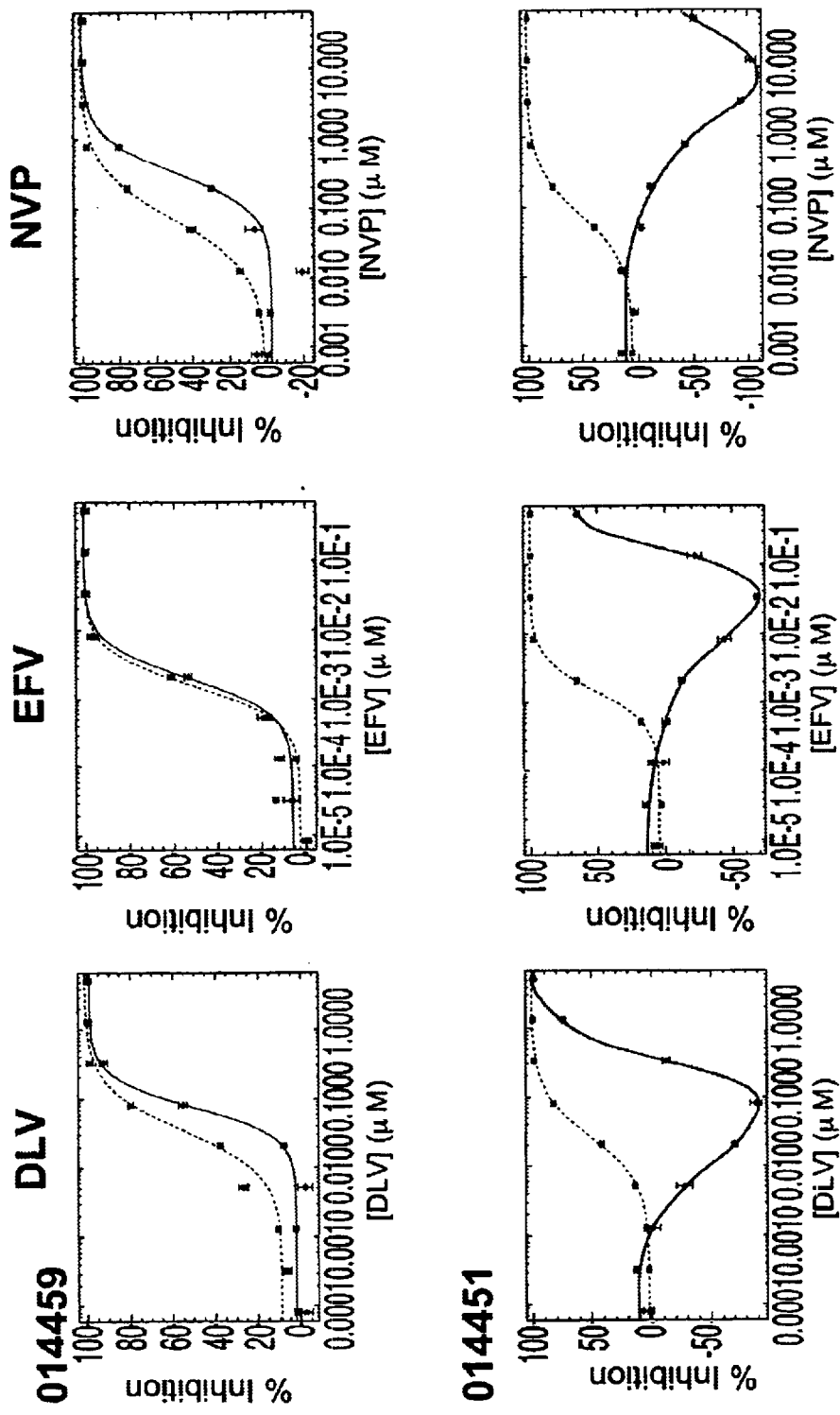
FIG. 10. Table of patient viruses containing mutations at HIV RT codon position 245, as described in Examples 8, 9, 10 and 11.
Figure 12A:
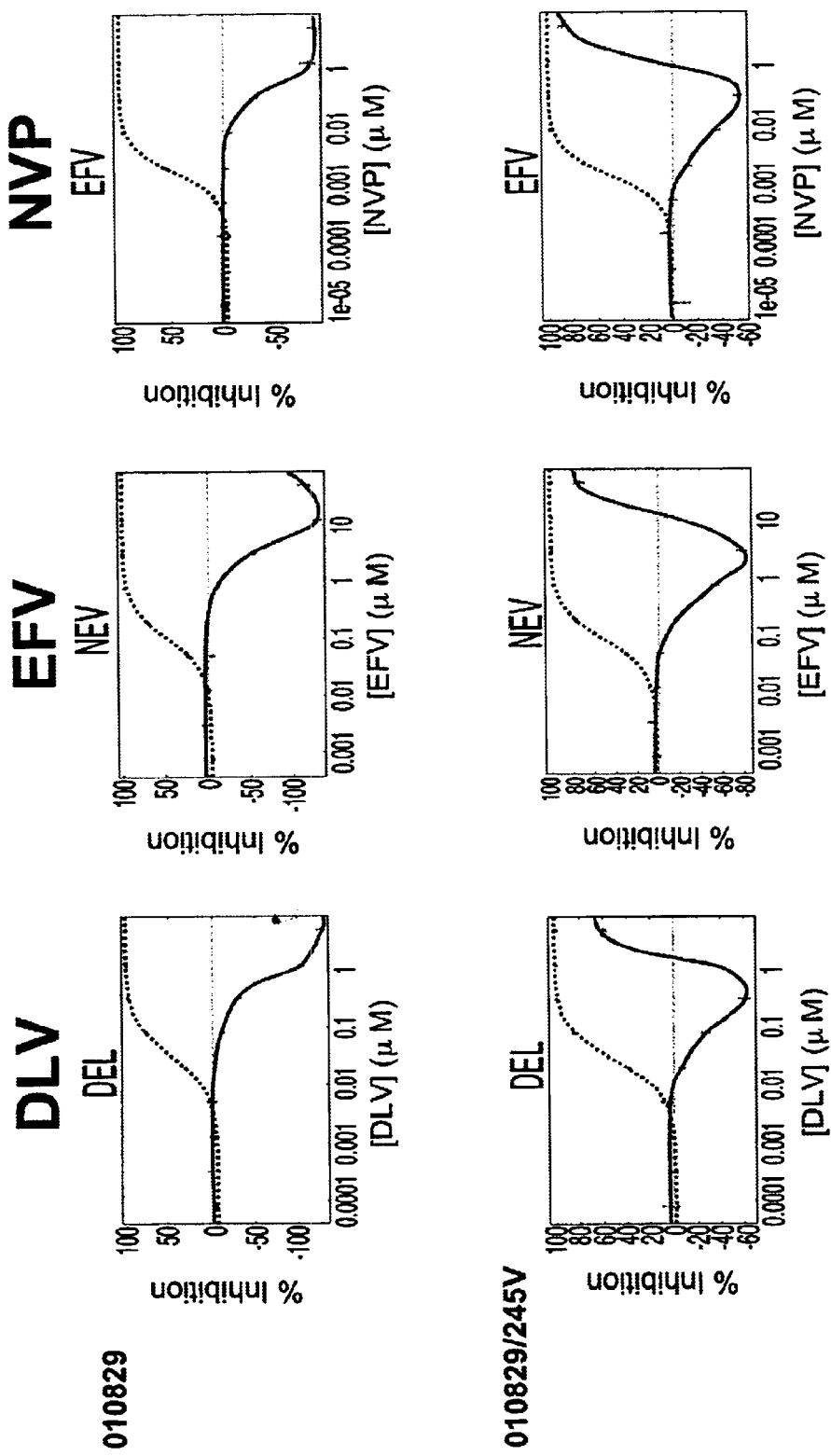
FIGS. 12A and 12B. Reduced susceptibility and drug-dependent stimulation of viral replication in of a site-directed mutants with HIV RT mutations K103N, 135T, and V245T, as described in Example 13. The results from each mutant are compared to results obtained from a drug susceptible virus control, such as PNL4-3, or HXB-2. Although mutations at each HIV RT codon position alone did not result in drug-dependent stimulation, the triple mutant exhibits drug-dependent stimulation for all three NNRTIs (delavirdine, efavirenz, or nevirapine), In these graphs, stimulation of viral replication manifests as percent inhibition less than zero (i.e. negative inhibition).
Figure 12B:
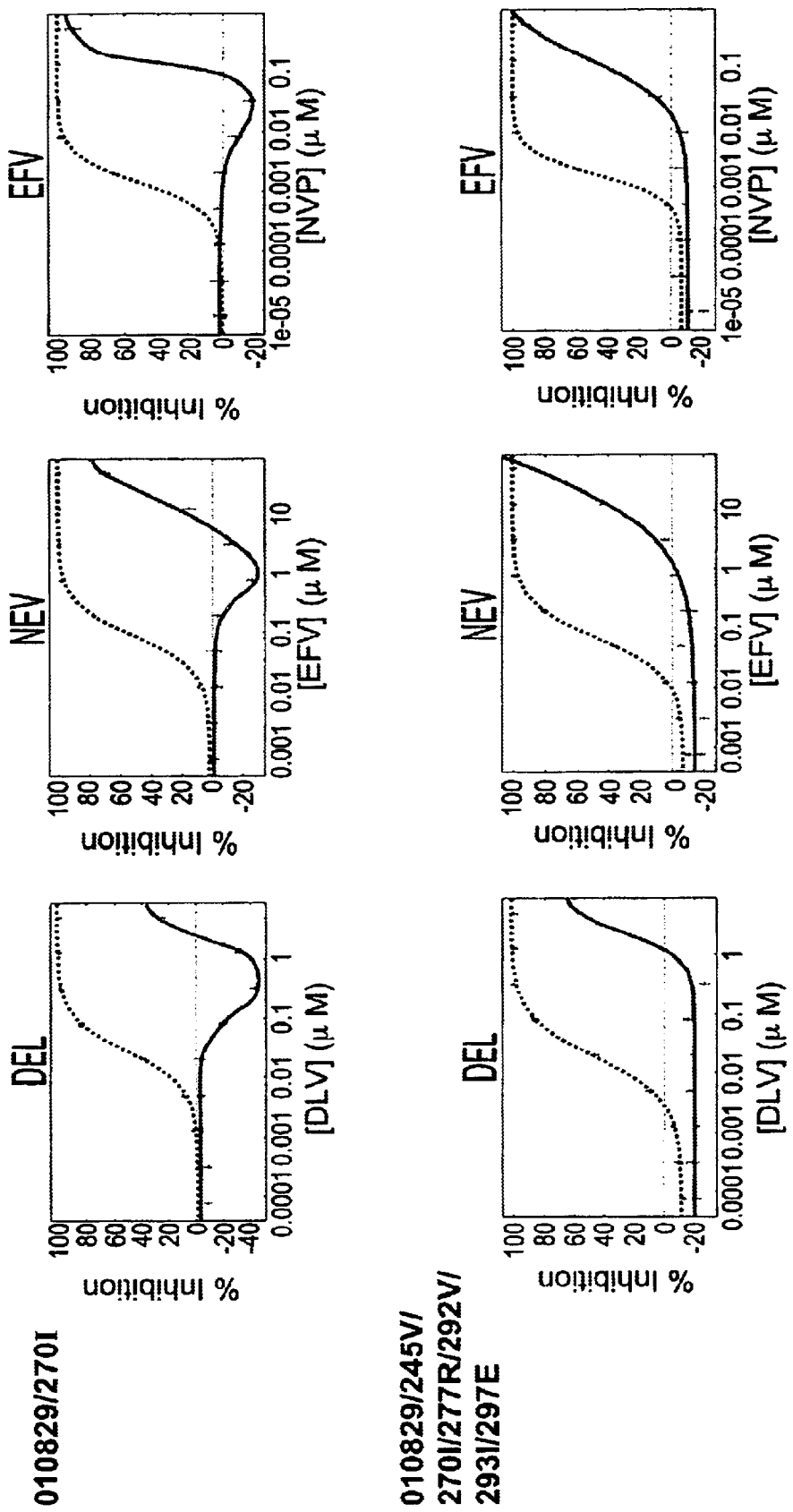
Figure 13:
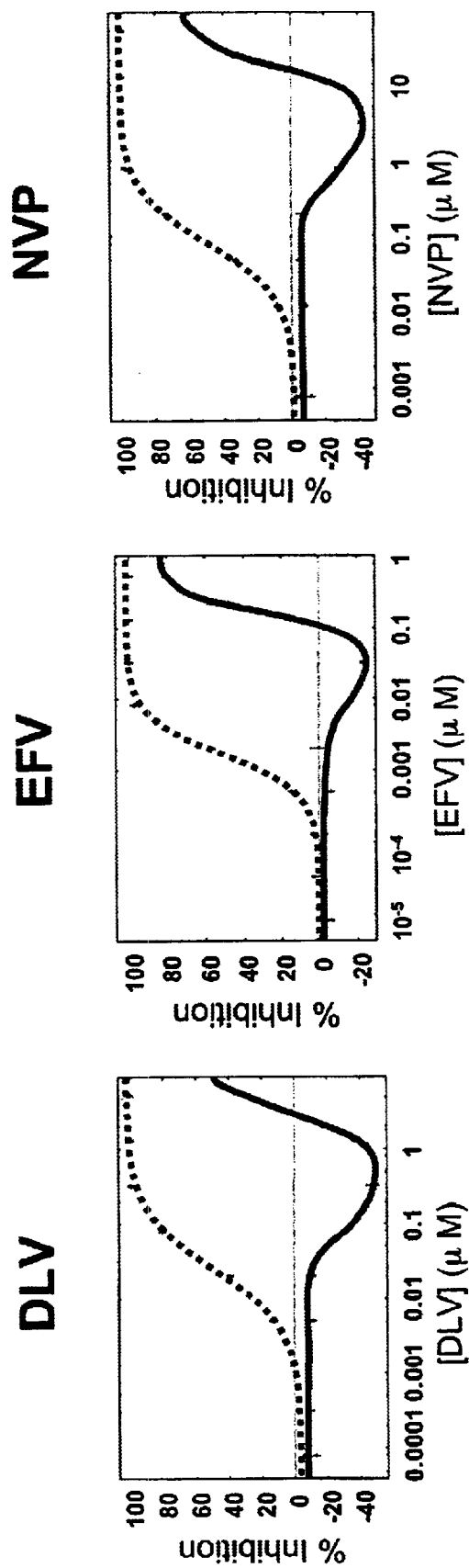
FIG. 13. Reverse mutagenesis of HIV RT codon position 270 in Patient 13522 as described in Example 12. The results from each mutant are compared to results obtained from a drug susceptible virus control, such as PNL4-3, or HXB-2. The top panel of the figure shows the graphs from the patient sample, containing the I270S mutation. In these graphs, stimulation of viral replication manifests as percent inhibition less than zero (i.e. negative inhibition) for all three NNRTIs (delavirdine, efavirenz, and nevirapine). The second panel of graphs shows the site-directed reversion of the mutation at codon 270. Although no longer exhibiting negative inhibition (stimulation of viral replication) for any of the three NNRTIs (delavirdine, efavirenz, or nevirapine), the site-directed mutant retains reduced drug susceptibility (drug resistance) to all three NNRTIs.

Host cells were seeded in 10-cm-diameter dishes and were transfected several days after plating with resistance test vector plasmid DNA and the envelope expression vector. Transfections were performed using a calcium-phosphate precipitation procedure. The cell culture media containing the DNA precipitate was replaced with fresh medium, from one to 24 hours, after transfection. Cell culture media containing resistance test vector viral particles was harvested one to four days after transfection and was passed through a 0.45-mm filter before being used to infect target host cells, or being stored at −80° C. HIV capsid protein (p24) levels in the harvested cell culture media were determined by an EIA method as described by the manufacturer (SAIC; Frederick, Md.). Before infection, target cells (293 and 293/T) were plated in cell culture media. Control infections were performed using cell culture media from mock transfections (no DNA) or transfections containing the resistance test vector plasmid DNA without the envelope expression plasmid. One to three or more days after infection, the media was removed and cell lysis buffer (Promega) was added to each well. Cell lysates were assayed for luciferase activity (FIG. 3). The inhibitory effect of the drug was determined using the following equation:

% luciferase inhibition=1−(RLUluc[drug]÷RLUluc)×100 where RLUluc [drug] is the Relative Light Unit of luciferase activity in infected cells in the presence of drug, and RLUluc is the Relative Light Unit of luciferase activity in infected cells in the absence of drug. IC50values were obtained from the sigmoidal curves that were generated from the data by plotting the percent inhibition of luciferase activity vs. the log10 drug concentration. The drug inhibition curves are shown in FIG. 3. The percent luciferase stimulation is the negative of the % inhibition calculated using the formula above. Curves showing drug-dependent stimulation of viral replication are shown in FIG. 4.

EXAMPLE 2

Correlating Phenotypic Susceptibility and Genotypic Analysis

Phenotypic susceptibility analysis of patient HIV samples

Resistance test vectors are constructed as described in Example 1. Resistance test vectors, or clones derived from the resistance test vector pools, are tested in a phenotypic assay to determine accurately and quantitatively the level of susceptibility to a panel of anti-retroviral drugs. This panel of anti-retroviral drugs may comprise members of the classes known as nucleoside reverse transcriptase inhibitors (NRTIs), non-nucleoside reverse transcriptase inhibitors (NNRTIs), and protease inhibitors (PRIs). The panel of drugs can be expanded as new drugs or new drug targets become available. An IC50 is determined for each resistance test vector pool for each drug tested. The pattern of susceptibility to all of the drugs tested is examined and compared to known patterns of susceptibility. The effect of drug on viral replication (i.e. luciferase activity) is further analyzed for any evidence of drug-dependent stimulation of viral replication, which would appear as a negative percent inhibition in the drug susceptibility graph. A patient sample may be further examined for genotypic changes correlated with the pattern of susceptibility observed.

Genotypic analysis of patient HIV samples

Resistance test vector DNAs, either pools or clones, are analyzed by any of the genotyping methods known to one of ordinaryt standing in the art (see PCT International Application No. PCT/US97/01609, filed Jan. 29, 1997). In one embodiment of the invention, patient HIV sample sequences are determined using viral RNA purification, RT/PCR and ABI chain terminator automated sequencing. The sequence that is determined is compared to control sequences present in the database or is compared to a sample from the patient prior to initiation of therapy, if available. The genotype is examined for sequences that are different from the control or pre-treatment sequence and correlated to the observed phenotype.

Phenotypic susceptibility analysis of site directed mutants

Genotypic changes that are observed to correlate with changes in phenotypic patterns of drug susceptibility are evaluated by construction of resistance test vectors containing the specific mutation on a defined, wild-type (drug susceptible) genetic background. Mutations may be incorporated alone and/or in combination with other known drug resistance mutations that are thought to modulate the susceptibility of HIV to a certain drugs or class of drugs. Mutations are introduced into the resistance test vector through any of the widely known methods for site-directed mutagenesis. In one embodiment of this invention the megaprimer PCR method for site-directed mutagenesis is used (Sarkar G, Sommer S S. (1990). Biotechniques 8:404–407). A resistance test vector containing the specific mutation or group of mutations is then tested using the phenotypic susceptibility assay described above and the susceptibility profile is compared to that of a genetically defined wild-type (drug susceptible) resistance test vector which lacks the specific mutations. Observed changes in the pattern of phenotypic susceptibility to the antiretroviral drugs tested are attributed to the specific mutations introduced into the resistance test vector.

EXAMPLE 3

Using Resistance Test Vectors and Site Directed Mutants to Correlate Genotypes and Phenotypes Associated with NNRTI Drug Susceptibility and Resistance, and Drug-Dependent Stimulation of Replication in HIV: M230L+Y181C Preparation of resistant test vectors and phenotypic analysis of patient ARG-014 HIV samples Resistance test vectors were constructed as described in Example 1 from virus samples obtained from an individual patient at three separate time points over a 16-week period. This patient had been previously treated with two NRTIs (didanosine and lamivudine) and a PRI indinavir. At the time the first sample (designated 98–773) was obtained, the patient began taking a new anti-viral regimen including an NRTI (abacavir) an NNRTI (nevirapine) and two PRI's (nelfinavir and saquinavir) (PRIs). The second sample (98–1046) was obtained 8 weeks later and a third sample (98–887) was obtained 16 weeks later. Viral load measurements showed that the patient experienced a transient reduction in viral load (at week 4) followed by a return to baseline viral load (~60,000 copies/ml) at weeks 8 and 16. Isolation of viral RNA and RT/PCR was used to generate patient derived segments (PDSs) that comprised viral sequences coding for all of PR and aa 1–313 of RT.

The PDS were inserted into an indicator gene viral vector to generate resistance test vectors designated RTV-773, RTV-1046 and RTV-887. These RTVs were then tested in a phenotypic assay to determine accurately and quantitatively the level of susceptibility to a panel of anti-retroviral drugs. This panel of anti-retroviral drugs comprised members of the classes known as NRTIs (zidovudine, lamivudine, Stavudine, didanosine, zalcitabine, and abacavir), NNRTIs (delavirdine, efavirenz and nevirapine), and PRIs (amprenavir, indinavir, nelfinavir, ritonavir, and saquinavir). An IC50 was determined for the resistance test vector pool for each drug tested. The pattern of susceptibility to all of the drugs tested was examined and compared to known patterns of susceptibility. A pattern of susceptibility to the NNRTIs was observed for patient samples RTV-1046 and RTV-887, in which there was a moderate decrease (5-fold) in efavirenz susceptibility and a significant decrease in nevirapine (>600-fold) and delavirdine (>250-fold) susceptibility.

Determination of genotype of patient HIV samples

RTV-773, RTV-1046 and RTV-887 DNA were analyzed by ABI chain terminator automated sequencing. The nucleotide sequence was compared to the consensus sequence of a wild type clade B HIV-1 (HIV Sequence Database Los Alamos, N. Mex.). The genotype was examined for sequences that are different from the control sequence. In RTV-773 (baseline sample) mutations were noted at HIV RE codons 41, 74, 184, 210, 211, 215, 228, and 296 compared to the control sequence. Mutations M41L, L74I, M184V, L210W and T215Y are associated with NRTI resistance. The mutations R211K and T296S are known sequence polymorphisms found among different wild-type (drug-sensitive) variants of HIV. In RTV-1046 and RTV-887 two additional mutations appeared at 181 and 230. The mutation Y181C has been previously shown to be associated with resistance to the NNRTIs nevirapine and delavirdine but not efavirenz. We examined the mutation, M230L, alone, and in combination with Y181C, using site directed mutagenesis and in vitro phenotypic susceptibility testing to correlate the observed changes in genotype with phenotype.

Site directed mutagenesis used to confirm the role of specific mutations in phenotypic susceptibility to anti-retroviral drugs in HIV The M230L mutation was introduced into a wild-type (drug sensitive) resistance test vector using the mega-primer method for site-directed mutagenesis (Sakar and Sommar, Ibid.). The resulting resistance test vector containing the M230L mutation (M230L-RTV) was then tested using the phenotypic assay described earlier, and the results were compared to those determined using a genetically defined resistance test vector that was wild type at position 230. We determined the pattern of phenotypic susceptibility to the NNRTIs, delavirdine, nevirapine and efavirenz, in the M230L-RTV. On a wild type background (i.e. M230L mutation alone) the M230L-RTV displayed a moderate loss of susceptibility to efavirenz (23-fold), nevirapine (39-fold) and delavirdine (58-fold) compared to a wild type control RTV. The M230L-RTV showed a drug-dependent stimulation of viral replication in the presence of delavirdine (~50%) and nevirapine (~50%) but not efavirenz. A resistance test vector containing the M230L mutation and the Y181C mutation (Y181C/M230L-RTV) was constructed and tested using the phenotypic assay described earlier and the results were compared to those determined using a genetically defined resistance test vector that was wild type at positions 181 and 230. We determined the pattern of phenotypic susceptibility to the NNRTIs, delavirdine, nevirapine and efavirenz, in the Y181C/M230L-RTV. The Y181C/M230L-RTV displayed a moderate reduction in susceptibility to efavirenz (25-fold), and high-level reductions in susceptibility to nevirapine (>600-fold) and delavirdine (>250-fold) compared to a wild type control RTV. The Y181C/M230L-RTV showed no drug-dependent stimulation of viral replication in the presence of any of the NNRTIs.

EXAMPLE 4

Using Resistance Test Vectors and Site Directed Mutants to Correlate Genotypes and Phenotypes Associated with NNRTI Drug Susceptibility and Resistance and Drug-Dependent Stimulation of Replication in HIV: M230L+K103N Preparation of resistant test vectors and phenotypic analysis of patient CCTG-2165 HIV samples Resistance test vectors were constructed as described in Example 1 from virus samples obtained from an individual patient at two separate time points over an 15-week period. This patient had been previously treated with two NRTIs (stavudine, laminvudine and a PRI nelfinavir). At the time the first sample (designated 99-2-009089) was obtained, the patient began taking a new anti-viral regimen including two NRI's (zidovudine, lamivudine and an NNRTI). A second sample (99-2-009839) was obtained 4 weeks when viral loads were undetectable, later and a third sample (99-2-010835) was obtained 15 weeks after baseline. A brief cessation of therapy was noted (8 days) between the second (wk 4) and third (wk 15) visits. Viral load measurements showed that the patient experienced a transient reduction in viral load (at week 4), followed by a return to baseline viral load (~2,000 copies/ml) at week 15. Isolation of viral RNA and RT/PCR was used to generate patient derived segments (PDS) that comprised viral sequences coding for all of PR and aa 1–313 of RT from the baseline and week 15 samples. The PDS were inserted into an indicator gene viral vector to generate resistance test vectors designated RTV-009089 and RTV-010835. These RTVs were then tested in a phenotypic assay to determine accurately and quantitatively the level of susceptibility to a panel of anti-retroviral drugs. This panel of anti-retroviral drugs comprised members of the classes known as NRTIs zidovudine, lamivudine, stavudine, didanosine, zalcitabine, and abacavir) NNRTIs (delavirdine, efavirenz and nevirapine), and PRIs (amprenavir, indinavir, nelfinavir, ritonavir, and saquinavir). An IC50 was determined for each resistance test vector pool for each drug tested. The pattern of susceptibility to all of the drugs tested was examined and compared to known patterns of susceptibility. A pattern of susceptibility to the NNRTIs was observed for patient sample RTV-010835 in which there was a significant decrease in efavirenz (270-fold), nevirapine (>600-fold) and delavirdine (>250-fold) susceptibility.

Determination of genotype of patient HIV samples

RTV-009089, and RTV-010835 DNA were analyzed by ABI chain terminator automated sequencing. The nucleotide sequence was compared to the consensus sequence of a wild type clade B HIV-1 (HIV Sequence Database Los Alamos, N. Mex.). The genotype was examined for sequences that are different from the control sequence. In RTV-009089 mutations were noted at positions 49, 102, 122, 169, 178, 184, 195, 200, 211, 245, 250, 275, 276, 277, 286, and 294 compared to the control sequence. In RTV-010835 additional mutations appeared at codons 103 and 230. The mutation K103N has been previously shown to be associated with resistance to the NNRTIs nevirapine, delavirdine and efavirenz. We examined the mutation, M230L, alone, and in combination with K103N, using site directed mutagenesis and in vitro phenotypic susceptibility testing to correlate the observed changes in genotype with phenotype.

Site directed mutagenesis is used to confirm the role of specific mutations in phenotypic susceptibility to anti-retroviral drugs in HIV The M230L mutation was tested alone and is described in Example 3 above. A resistance test vector containing the M230L mutation and the K103N mutation (K103N/M230L-RTV) was constructed and tested using the phenotypic assay described earlier, and the results were compared to those determined using a genetically defined resistance test vector that was wild type at positions 103 and 230. We determined the pattern of phenotypic susceptibility to the NNRTIs, delavirdine, nevirapine and efavirenz, in the K103N/M230L-RTV. The K103N/M230L-RTV displayed high-level reductions in susceptibility to nevirapine (>600-fold), efavirenz (>470-fold) and delavirdine (>250-fold) compared to a wild type control RTV. The K103N/M230L-RTV also showed significant drug-dependent stimulation of viral replication in the presence of nevirapine (~70%), efavirenz (~40%) and delavirdine (~100%). A resistance test vector containing the M230L, K103N and the M184V mutations (K103N/M230L/M184V-RTV) was constructed and tested using the phenotypic assay described earlier and the results were compared to those determined using a genetically defined resistance test vector that was wild type at positions 103, 184 and 230. The addition of the M184V mutation onto the K103N, M230L backbone results in a reversal of the drug-dependent stimulation of viral replication.

EXAMPLE 5

Using Resistance Test Vectors to Correlate Genotypes and Phenotypes Associated with NNRTI Drug Susceptibility And Resistance and Drug-Dependent Stimulation of Replication in HIV: M230L+K101L+K103N+G190S Preparation of resistant test vectors and phenotypic analysis of patient CCTG-1025 HIV samples Resistance test vectors were constructed as described in Example 1 from virus samples obtained from an individual patient at two separate time points over a 48-week period. This patient had been previously treated with four NRTIs (zidovudine, stavudine, didanosine, lamivudine, and a PRI nelfinavir. At the time the first sample (designated AA2919) was obtained, the patient began taking a new anti-viral regimen including two NRTIs (stavudine and abacavir) and one PRI (indinavir). The viral load in this patient fell below detectable and remained undetectable for an additional 48 weeks. Efavirenz was added to the regimen after 9 weeks. A second sample (00-2-012090) was obtained 48 weeks after the initiation of study when the viral load increased to 455. Isolation of viral RNA and RT/PCR was used to generate patient derived segments (PDS) that comprised viral sequences coding for all of PR and aa 1–313 of RT from all three samples. The PDS were inserted into an indicator gene viral vector to generate resistance test vectors designated RTV-2919 and RTV-012090. These RTVs were then tested in a phenotypic assay to determine accurately and quantitatively the level of susceptibility to a panel of anti-retroviral drugs. This panel of anti-retroviral drugs comprised members of the classes known as NRTIs (zidovudine, lamivudine, stavudine, didanosine, zalcitabine, and abacavir) NNRTIs (delavirdine, efavirenz and nevirapine), and PRIs (amprenavir, indinavir, nelfinavir, ritonavir, and saquinavir). An IC50 was determined for each resistance test vector pool for each drug tested. The pattern of susceptibility to all of the drugs tested was examined and compared to known patterns of susceptibility. A pattern of susceptibility to the NNRTIs was observed for patient RTV-012090 in which there was a significant decrease in susceptibility to efavirenz (>450-fold), nevirapine (>600-fold) and delavirdine (144-fold) susceptibility and significant drug-dependent stimulation of viral replication in the presence of nevirapine (~80%), delavirdine (~30%) and efavirenz (~40%).

Determination of genotype of patient HIV samples

RTV-2919 and RTV-012090 DNA were analyzed by ABI chain terminator automated sequencing. The nucleotide sequence was compared to the consensus sequence of a wild type clade B HIV-1 (HIV Sequence Database Los Alamos, N. Mex.). The genotype was examined for sequences that are different from the control sequence. In RTV-2919 mutations were noted at HIV RT codons 67, 86, 102, 118, 122, 158, 162, 174, 177, 211, 214, 215, 272, 275, 276, 277, 278, 281, 286 and 293 compared to the control sequence. In RTV-012090 additional mutations appeared at codons 101, 103, 190 and 230. The mutations K101E, K103N and G190S have been previously shown to be associated with resistance to the NNRTIs nevirapine, delavirdine and efavirenz. In this patient sample the appearance of the mutations K101E, K103N, G190S and M230L are correlated with the significant drug-dependent stimulation of viral replication in response to all three NNRTIs.

EXAMPLE 6

Using Resistance Test Vectors to Correlate Genotypes and Phenotypes Associated with NNRTI Drug Susceptibility and Resistance and Drug-Dependent Stimulation of Replication in HIV: V241S+K103N+I135T Preparation of resistant test vectors and phenotypic analysis of patient 011073 HIV samples A resistance test vector was constructed as described in Example 1 from a virus sample obtained from patient 011073. The prior and current treatment regimens are unknown. Isolation of viral RNA and RT/PCR was used to generate a patient derived segment (PDS) that comprised viral sequences coding for all of PR and aa 1–313 of RT. The PDS was inserted into an indicator gene viral vector to generate a resistance test vector designated RTV-011073. RTV-011073 was then tested in a phenotypic assay to determine accurately and quantitatively the level of susceptibility to a panel of anti-retroviral drugs. This panel of anti-retroviral drugs comprised members of the classes known as NRTIs (zidovudine, lamivudine, stavudine, didanosine, zalcitabine and abacavir), NNRTIs (delavirdine, efavirenz and nevirapine), and PRIs (amprenavir, indinavir, nelfinavir, ritonavir, and saquinavir). An IC50 was determined for each resistance test vector pool for each drug tested. The pattern of susceptibility to all of the drugs tested was examined and compared to known patterns of susceptibility. A pattern of susceptibility to the NNRTIs was observed for patient RTV-011073 in which there was a significant decrease in efavirenz (>450-fold), nevirapine (>600-fold) and delavirdine (>250-fold) susceptibility and a significant drug-dependent stimulation of viral replication in the presence of nevirapine (~70%), delavirdine (~90%) and efavirenz (~80%).

Determination of genotype of patient HIV samples

RTV-011073 DNA was analyzed by ABI chain terminator automated sequencing. The nucleotide sequence was compared to the consensus sequence of a wild type clade B HIV-1 (HIV Sequence Database Los Alamos, N. Mex.). The genotype was examined for sequences that are different from the control sequence. In RTV-011073 mutations were noted at HIV RT codons 20, 67, 69, 70, 102, 103, 118, I135T, 162, 211, 214, 218, 219, 241 and 277 compared to the control sequence.

Site directed mutagenesis used to confirm the role of specific mutations in phenotypic susceptibility to anti-retroviral drugs in HIV A resistance test vector containing all of the mutations present in RTV-011073 except for the V241S and the T277K was constructed and tested using the phenotypic assay described earlier. The results were compared to those determined using the parent RTV-011073. We determined the pattern of phenotypic susceptibility to the NNRTIs, delavirdine, nevirapine and efavirenz, in the reverted vector RTV-011073/241V/277T. The RTV-011073/241V/277T displayed high-level reductions in susceptibility to nevirapine (126-fold), efavirenz (54-fold) and delavirdine (50-fold) compared to a wild type control RTV. The RTV-011073/241V/277T showed no drug-dependent stimulation of viral replication in the presence of any NNRTI tested. A resistance test vector containing all of the mutations present in RTV-011073 except for the V241S was constructed and tested using the phenotypic assay described earlier. The results were compared to those determined using the parent RTV-011073. We determined the pattern of phenotypic susceptibility to the NNRTIs, delavirdine, nevirapine and efavirenz, in the reverted vector RTV-011073/241V. The RTV-011073/241V displayed high-level reductions in susceptibility to nevirapine (146-fold), efavirenz (54-fold) and delavirdine (59-fold) compared to a wild type control RTV. The RTV-011073/241V showed no drug-dependent stimulation of viral replication in the presence of any NNRTI tested. In this patient sample the correlation of drug-dependent stimulation of viral replication with the mutation at V241S is very striking. A resistance test vector containing a single mutation at V241S (RTV-V241S) was constructed and tested in the phenotypic assay described earlier. The results were compared to those determined using a wild type control RTV. We determined the pattern of phenotypic susceptibility to the NNRTIS, delavirdine, nevirapine and efavirenz, in the RTV-V241S. The RTV-V241S displayed small reductions in susceptibility to nevirapine (9-fold), efavirenz (3-fold) and delavirdine (6-fold) compared to a wild type control RTV. The RTV-V241S showed drug-dependent stimulation of viral replication in the presence of nevirapine (~30%), delavirdine (~25%) but no drug-dependent stimulation of viral replication in the presence of efavirenz.

EXAMPLE EXAMPLE 7
Using Resistance Test Vectors to Correlate Genotypes and Phenotypes Associated with NNRTI Drug Susceptibility And Resistance and Drug-Dependent Stimulation of Replication in HIV: V241S+K101E+V106M+I135T+E138A+G190A Preparation of resistant test vectors and phenotypic analysis of patient 014451 HIV samples Resistance test vectors were constructed as described in Example 1 from virus samples obtained from an individual patient at two separate time points separated by a 32-week period. The prior and current treatment regimens are unknown. Isolation of viral RNA and RT/PCR was used to generate patient derived segments (PDS) that comprised viral sequences coding for all of PR and aa 1–13 of RT from all three samples. The PDS were inserted into an indicator gene viral vector to generate resistance test vectors designated RTV-014459 and RTV-014451. These RTVs were then tested in a phenotypic assay to determine accurately and quantitatively the level of susceptibility to a panel of anti-retroviral drugs. This panel of anti-retroviral drugs comprised members of the classes known as NRTIs zidovudine, lamivudine, stavudine, didanosine, zalcitabine, and abacavir) NNRTIs (delavirdine, efavirenz and nevirapine), and PRIs (amprenavir, indinavir, nelfinavir, ritonavir, and saquinavir). An IC50 was determined for each resistance test vector pool for each drug tested. The pattern of susceptibility to all of the drugs tested was examined and compared to known patterns of susceptibility. A pattern of susceptibility to the NNRTIs was observed for patient RTV-014451 in which there was a significant decrease in efavirenz (>450-fold) nevirapine (>600-fold) and delavirdine (41-fold) susceptibility and a significant drug-dependent stimulation of viral replication in the presence of nevirapine (~100%), delavirdine (~90%) and efavirenz (~70%).

Determination of genotype of patient HIV samples

RTV-014459 and RTV-014459 DNA were analyzed by ABI chain terminator automated sequencing. The nucleotide sequence was compared to the consensus sequence of a wild type clade B HIV-1 (HIV Sequence Database Los Alamos, N. Mex.). The genotype was examined for sequences that are different from the control sequence. In RTV-014459 mutations were noted at HIV RT 35I, 41, 49, 83, 102, 123, 135, 138, 174, 177, 178, 184, 215, 241, 257, 261, 277, 286, 293 and 297 compared to the control NL4-3 sequence. In RTV-014451 additional mutations appeared at codons 101, 106 and 190. The mutations K101E, V106M and G190A have been previously shown to be associated with resistance to the NNRTIs nevirapine, delavirdine and efavirenz, but not with stimulation of viral replication. In this patient sample, the appearance of the mutations K101E, V106M and G190A on the specific genetic backbone present in this virus is correlated with the significant drug-dependent stimulation of viral replication in response to all three NNRTIs. The results shown in Example 6 above suggest that the mutation V241I may contribute to the stimulation of viral replication seen in this virus.

EXAMPLE 8
Using Resistance Test Vectors to Correlate Genotypes and Phenotypes Associated with NNRTI Drug Susceptibility and Resistance and Drug-Dependent Stimulation of Replication in HIV: V245E in Combination with Multiple Other Mutations Preparation of resistant test vectors and phenotypic analysis of patient 005738 HIV samples A resistance test vector was constructed as described in Example 1 from a virus sample obtained from patient 005738. The prior and current treatment regimens are unknown. Isolation of viral RNA and RT/PCR was used to generate a patient derived segment (PDS) that comprised viral sequences coding for all of PR and aa 1–313 of RT from both samples. The PDS were inserted into an indicator gene viral vector to generate a resistance test vector designated RTV-005738. RTV-005738 was then tested in a phenotypic assay to determine accurately and quantitatively the level of susceptibility to a panel of anti-retroviral drugs. This panel of anti-retroviral drugs comprised members of the classes known as NRTIs zidovudine, lamivudine, stavudine, didanosine, zalcitabine, and abacavir) NNRTIs (delavirdine, efavirenz and nevirapine), and PRIs (amprenavir, indinavir, nelfinavir, ritonavir, and saquinavir). An IC50 was determined for each resistance test vector pool for each drug tested. The pattern of susceptibility to all of the drugs tested was examined and compared to known patterns of susceptibility. A pattern of susceptibility to the NNRTIs was observed for patient sample RTV-005738 in which there was a moderate decrease in efavirenz (17-fold) nevirapine (>600-fold) and delavirdine (63-fold) susceptibility and a significant drug-dependent stimulation of viral replication in the presence of nevirapine (~20%), delavirdine (~40%) and efavirenz (~20%).

Determination of genotype of patient HIV samples

RTV-005738 DNA was analyzed by ABI chain terminator automated sequencing. The nucleotide sequence was compared to the consensus sequence of a wild type clade B HIV-1 (HIV Sequence Database Los Alamos, N. Mex.). The genotype was examined for sequences that are different from the control sequence. In RTV-005738 mutations were noted at positions D67N, K70R, R83K, A98G, Q102K, K122P, I135T, I142V, C162S, K173Q, I178L, Y181C, G196E, I202V, T215F, D218E, K219Q, V245E, A272P, R277K, V293I and E297Q compared to the control sequence.

Preparation of resistant test vectors and phenotypic analysis of patient 007130 HIV samples A resistance test vector was constructed as described in Example 1 from a virus sample obtained from patient 007130. The prior and current treatment regimens are unknown. Isolation of viral RNA and RT/PCR was used to generate a patient derived segment (PDS) that comprised viral sequences coding for all of PR and aa 1–313 of RT. The PDS were inserted into an indicator gene viral vector to generate a resistance test vector designated RTV-007130. RTV-007130 was then tested in a phenotypic assay to determine accurately and quantitatively the level of susceptibility to a panel of anti-retroviral drugs. This panel of anti-retroviral drugs comprised members of the classes known as NRTIs zidovudine, lamivudine, stavudine, didanosine, zalcitabine, and abacavir) NNRTIs (delavirdine, efavirenz and nevirapine), and PRIs (amprenavir, indinavir, nelfinavir, ritonavir, and saquinavir). An IC50 was determined for the resistance test vector pool for each drug tested. The pattern of susceptibility to all of the drugs tested was examined and compared to known patterns of susceptibility. A pattern of susceptibility to the NNRTIs was observed for patient RTV-007130 in which there was a significant decrease in efavirenz (>450-fold), nevirapine (>600-fold) and delavirdine (>250-fold) susceptibility and a significant drug-dependent stimulation of viral replication in the presence of nevirapine (~50%), delavirdine (~30%) and efavirenz (~40%).

Determination of genotype of patient HIV samples

RTV-007130 DNA was analyzed by ABI chain terminator automated sequencing. The nucleotide sequence was compared to the consensus sequence of a wild type clade B HIV-1 (HIV Sequence Database Los Alamos, N. Mex.). The genotype was examined for sequences that are different from the control sequence. In RTV-007130 mutations were noted at codons 67, 101, 102, 103, 122, 135, 162, 174, 184, 190, 208, 221, 245, 272, 277, 283, 293 compared to the control sequence.

EXAMPLE 9

Using Resistance Test Vectors to Correlate Genotypes and Phenotypes Associated with NNRTI Drug Susceptibility and Resistance and Drug-Dependent Stimulation of Replication in HIV: V245T in Combination with Multiple Other Mutations Preparation of resistant test vectors and phenotypic analysis of patient 006782 HIV samples A resistance test vector was constructed as described in Example 1 from a virus sample obtained from patient 006782. The prior and current treatment regimens are unknown. Isolation of viral RNA and RT/PCR was used to generate a patient derived segment (PDS) that comprised viral sequences coding for all of PR and aa 1–313 of RT. The PDS were inserted into an indicator gene viral vector to generate a resistance test vector designated RTV-006782. RTV-006782 was then tested in a phenotypic assay to determine accurately and quantitatively the level of susceptibility to a panel of anti-retroviral drugs. This panel of anti-retroviral drugs comprised members of the classes known as NRTIs zidovudine, lamivudine, stavudine, didanosine, zalcitabine, and abacavir) NNRTIs (delavirdine, efavirenz and nevirapine), and PRIs (amprenavir, indinavir, nelfinavir, ritonavir, and saquinavir). An IC50 was determined for the resistance test vector pool for each drug tested. The pattern of susceptibility to all of the drugs tested was examined and compared to known patterns of susceptibility. A pattern of susceptibility to the NNRTIs was observed for patient RTV-007130 in which there was a small decrease in efavirenz (5-fold), nevirapine (8-fold) and delavirdine (18.5-fold) susceptibility and a significant drug-dependent stimulation of viral replication in the presence of nevirapine (~60%), delavirdine (~70%) and efavirenz (~25%).

Determination of genotype of patient HIV samples

RTV-006782 DNA was analyzed by ABI chain terminator automated sequencing. The nucleotide sequence was compared to the consensus sequence of a wild type clade B HIV-1 (HIV Sequence Database Los Alamos, N. Mex.). The genotype was examined for sequences that are different from the control sequence. In RTV-006782 mutations were noted at HIV RT codons Q102K, D123E, I135T, E138A, C162S, G196E, I202V, V245T, R277K, T286A, V293I, P294T and E297K compared to the control sequence.

Preparation of resistant test vectors and phenotypic analysis of patient 012123 HIV samples A resistance test vector was constructed as described in Example 1 from a virus sample obtained from patient 012123. The prior and current treatment regimens are unknown. Isolation of viral RNA and RT/PCR was used to generate a patient derived segment (PDS) that comprised viral sequences coding for all of PR and aa 1–313 of RT. The PDS were inserted into an indicator gene viral vector to generate a resistance test vector designated RTV-012123. RTV-012123 was then tested in a phenotypic assay to determine accurately and quantitatively the level of susceptibility to a panel of anti-retroviral drugs. This panel of anti-retroviral drugs comprised members of the classes known as NRTIs zidovudine, lamivudine, stavudine, didanosine, zalcitabine, and abacavir) NNRTIs (delavirdine, efavirenz and nevirapine), and PRIs (amprenavir, indinavir, nelfinavir, ritonavir, and saquinavir). An IC50 was determined for the resistance test vector pool for each drug tested. The pattern of susceptibility to all of the drugs tested was examined and compared to known patterns of susceptibility. A pattern of susceptibility to the NNRTIs was observed for patient RTV-012123 in which there was a significant decrease in efavirenz (>450-fold), nevirapine (>600-fold) and delavirdine (>250-fold) susceptibility, and a significant drug-dependent stimulation of viral replication in the presence of nevirapine (~20%), delavirdine (~80%) and efavirenz (~70%).

Determination of genotype of patient HIV samples

RTV-012123 DNA was analyzed by ABI chain terminator automated sequencing. The nucleotide sequence was compared to the consensus sequence of a wild type clade B HIV-1 (HIV Sequence Database Los Alamos, N. Mex.). The genotype was examined for sequences that are different from the control sequence. In RTV-012123 mutations were noted at HIV RT codons 20, 39, 41, 44, 60, 67, 98, 102, 103, 118, 122, 135, 142, 162, 173, 181, 190, 196, 202, 210, 215, 221, 245, 272, 277, 293 and 297 compared to the control sequence.

Preparation of resistant test vectors and phenotypic analysis of patient 014397 HIV samples A resistance test vector was constructed as described in Example 1 from a virus sample obtained from patient 014397. The prior and current treatment regimens are unknown. Isolation of viral RNA and RT/PCR was used to generate a patient derived segment (PDS) that comprised viral sequences coding for all of PR and aa 1–313 of RT. The PDS were inserted into an indicator gene viral vector to generate a resistance test vector designated RTV-014397. RTV-014397 was then tested in a phenotypic assay to determine accurately and quantitatively the level of susceptibility to a panel of anti-retroviral drugs. This panel of anti-retroviral drugs comprised members of the classes known as NRTIs zidovudine, lamivudine, stavudine, didanosine, zalcitabine, and abacavir) NNRTIs (delavirdine, efavirenz and nevirapine), and PRIs (amprenavir, indinavir, nelfinavir, ritonavir, and saquinavir). An IC50 was determined for the resistance test vector pool for each drug tested. The pattern of susceptibility to all of the drugs tested was examined and compared to known patterns of susceptibility. A pattern of susceptibility to the NNRTIs was observed for patient RTV-014397 in which there was a significant decrease in efavirenz (>450-fold), nevirapine (>600-fold) and delavirdine (>250-fold) susceptibility and a significant drug-dependent stimulation of viral replication in the presence of nevirapine (~100%), delavirdine (~100%) and efavirenz (~70%).

Determination of genotype of patient HIV samples

RTV-014397 DNA was analyzed by ABI chain terminator automated sequencing. The nucleotide sequence was compared to the consensus sequence of a wild type clade B HIV-1 (HIV Sequence Database Los Alamos, N. Mex.). The genotype was examined for sequences that are different from the control sequence. In RTV-014397 mutations were noted at HIV RT codons 31, 102, 103, 123, 162, 166, 177, 211, 215, 228, 245, 272 and 277 compared to the control sequence.

EXAMPLE 10
Using Resistance Test Vectors to Correlate Genotypes and Phenotypes Associated with NNRTI Drug Susceptibility And Resistance and Drug-Dependent Stimulation of Replication in HIV: V245M in Combination with Multiple Other Mutations Preparation of resistant test vectors and phenotypic analysis of patient 013415 HIV samples A resistance test vector was constructed as described in Example 1 from a virus sample obtained from patient 013415. The prior and current treatment regimens are unknown. Isolation of viral RNA and RT/PCR was used to generate a patient derived segment (PDS) that comprised viral sequences coding for all of PR and aa 1–313 of RT. The PDS were inserted into an indicator gene viral vector to generate a resistance test vector designated RTV-013415. RTV-013415 was then tested in a phenotypic assay to determine accurately and quantitatively the level of susceptibility to a panel of anti-retroviral drugs. This panel of anti-retroviral drugs comprised members of the classes known as NRTIs zidovudine, lamivudine, stavudine, didanosine, zalcitabine, and abacavir) NNRTIs (delavirdine, efavirenz and nevirapine), and PRIs (amprenavir, indinavir, nelfinavir, ritonavir, and saquinavir). An IC50 was determined for the resistance test vector pool for each drug tested. The pattern of susceptibility to all of the drugs tested was examined and compared to known patterns of susceptibility. A pattern of susceptibility to the NNRTIs was observed for patient RTV-013415 in which there was a significant decrease in efavirenz (>450-fold), nevirapine (>600-fold) and delavirdine (>250-fold) susceptibility and a significant drug-dependent stimulation of viral replication in the presence of nevirapine (~20%), delavirdine (~30%) and efavirenz (~20%).

Determination of genotype of patient HIV samples

RTV-013415 DNA was analyzed by ABI chain terminator automated sequencing. The nucleotide sequence was compared to the consensus sequence of a wild type clade B HIV-1 (HIV Sequence Database Los Alamos, N. Mex.). The genotype was examined for sequences that are different from the control sequence. In RTV-013415 mutations were noted at HIV RT codons 35, 102, 103, 122, 123, 135, 162, 177, 200, 207, 211, 225, 245, 264, 277 and 290 compared to the control sequence.

EXAMPLE 11
Using Resistance Test Vectors to Correlate Genotypes and Phenotypes Associated with NNRTI Drug Susceptibility And Resistance and Drug-Dependent Stimulation of Replication in HIV: K103N+V245E+I270M Preparation of resistant test vectors and phenotypic analysis of patient 10829 HIV samples A resistance test vector was constructed as described in Example 1 from a virus sample obtained from patient 10829. The prior and current treatment regimens are unknown. Isolation of viral RNA and RT/PCR was used to generate a patient derived segment (PDS) that comprised viral sequences coding for all of PR and aa 1–313 of RT. The PDS were inserted into an indicator gene viral vector to generate a resistance test vector designated RTV-010829. RTV-010829 was then tested in a phenotypic assay to determine accurately and quantitatively the level of susceptibility to a panel of anti-retroviral drugs. This panel of anti-retroviral drugs comprised members of the classes known as NRTIs zidovudine, lamivudine, stavudine, didanosine, zalcitabine, and abacavir) NNRTIs (delavirdine, efavirenz and nevirapine), and PRIs (amprenavir, indinavir, nelfinavir, ritonavir, and saquinavir). An IC50 was determined for the resistance test vector pool for each drug tested. The pattern of susceptibility to all of the drugs tested was examined and compared to known patterns of susceptibility. A pattern of susceptibility to the NNRTIs was observed for patient RTV-011073 in which there was a sigificant decrease in efavirenz (>450-fold), nevirapine (>600-fold) and delavirdine (>250-fold) susceptibility and a significant drug-dependent stimulation of viral replication in the presence of nevirapine (~100%), delavirdine (~100%) and efavirenz (~80%).

Determination of genotype of patient HIV samples

RTV-010829 DNA was analyzed by ABI chain terminator automated sequencing. The nucleotide sequence was compared to the consensus sequence of a wild type clade B HIV-1 (HIV Sequence Database Los Alamos, N. Mex.). The genotype was examined for sequences that are different from the control sequence. In RTV-010829 mutations were noted at HIV codons 31, 35, 90, 102, 103, 122, 162, 196, 211, 214, 215, 228, 245, 270, 276, 277, 292, 293 and 297 compared to the control sequence.

Site directed revese-mutagenesis used to confirm the role of specific mutations in phenotypic susceptibility to anti-retroviral drugs in HIV A resistance test vector containing all of the mutations present in RTV-010829 except for the V245E mutation (RTV-010829/245V) was constructed and tested using the phenotypic assay described earlier. The results were compared to those determined using the parent RTV-010829. We determined the pattern of phenotypic susceptibility to the NNRTIs, delavirdine, nevirapine and efavirenz, in the reverted vector RTV-010829/245V. The RTV-010829/245V displayed high-level reductions in susceptibility to nevirapine (505-fold), efavirenz (189-fold) and delavirdine (182-fold) compared to a wild type control RTV. The RTV-010829/245V showed drug-dependent stimulation of viral replication in the presence of nevirapine (~80%), efavirenz (~60%) and delavirdine (~60%). A resistance test vector containing all of the mutations present in RTV-010829 except for the I270M (RTV-010829/270I) was constructed and tested using the phenotypic assay described earlier. The results were compared to those determined using the parent RTV-010829. We determined the pattern of phenotypic susceptibility to the NNRTIs, delavirdine, nevirapine and efavirenz, in the reverted vector RTV-010829/270I. The RTV-010829/270I displayed high-level reductions in susceptibility to nevirapine (341-fold), efavirenz (145-fold) and delavirdine (247-fold) compared to a wild type control RTV. The RTV-010829/245V showed drug-dependent stimulation of viral replication in the presence of nevirapine (~30%), efavirenz (~20%) and delavirdine (~40%). A resistance test vector containing all of the mutations present in RTV-010829 except for V245E, I270M, V276I, R277K, V292I, V293I and E297K (RTV-010829/245V-297E) was constructed and tested using the phenotypic assay described earlier. The results were compared to those determined using the parent RTV-010829. We determined the pattern of phenotypic susceptibility to the NNRTIs, delavirdine, nevirapine and efavirenz, in the reverted vector RTV-010829/245V-297E. The RTV-010829/245V-297E displayed high-level reductions in susceptibility to nevirapine (233-fold), efavirenz (76-fold) and delavirdine (198-fold) compared to a wild type control RTV. The RTV-010829/245V-297E showed no drug-dependent stimulation of viral replication in the presence of nevirapine, efavirenz, or delavirdine. In this patient sample, drug-dependent stimulation of viral replication is modulated by the presence of the mutations V245E and I270M. Drug-dependent stimulation of viral replication can be completely abrogated by reversion of mutations V245E, I270M, V276I, R277K, V292I, V293I and E297K.

EXAMPLE 12

Using Resistance Test Vectors to Correlate Genotypes and Phenotypes Associated with NNRTI Drug Susceptibility And Resistance and Drug-Dependent Stimulation of Replication in HIV: K103N+I135T+I270S Preparation of resistant test vectors and phenotypic analysis of patient 013522 HIV samples A resistance test vector was constructed as described in Example 1 from a virus sample obtained from patient 013522. The prior and current treatment regimens are unknown. Isolation of viral RNA and RT/PCR was used to generate a patient derived segment (PDS) that comprised viral sequences coding for all of PR and aa 1–313 of RT from all three samples. The PDS were inserted into an indicator gene viral vector to generate a resistance test vector designated RTV-013522. RTV-013522 was then tested in a phenotypic assay to determine accurately and quantitatively the level of susceptibility to a panel of anti-retroviral drugs. This panel of anti-retroviral drugs comprised members of the classes known as NRTIs (zidovudine, lamivudine, stavudine, didanosine, zalcitabine and abacavir), NNRTIs (delavirdine, efavirenz and nevirapine), and PRIs (amprenavir, indinavir, nelfinavir, ritonavir, and saquinavir). An IC50 was determined for each resistance test vector pool for each drug tested. The pattern of susceptibility to all of the drugs tested was examined and compared to known patterns of susceptibility. A pattern of susceptibility to the NNRTIs was observed for patient RTV-013522 in which there was a sigificant decrease in efavirenz (>450-fold), nevirapine (>600-fold) and delavirdine (>250-fold) susceptibility and a significant drug-dependent stimulation of viral replication in the presence of nevirapine (~90%), delavirdine (~110%) and efavirenz (~100%)

Determination of genotype of patient HIV samples

RTV-013522 DNA was analyzed by ABI chain terminator automated sequencing. The nucleotide sequence was compared to the consensus sequence of a wild type clade B HIV-1 (HIV Sequence Database Los Alamos, N. Mex.). The genotype was examined for sequences that are different from the control sequence. In RTV-013522 mutations were noted at HIV RT codons 35, 60, 68, 102, 103, 135, 162, K166R, 184, 196, 204, 211, 248, 250, 270, 286, 293 and 297 compared to the control sequence.

Site directed revese-mutagenesis is used to confirm the role of specific mutations in phenotypic susceptibility to anti-retroviral drugs in HIV A resistance test vector containing all of the mutations present in RTV-010829 except for the I270S (RTV-013522/270I) was constructed and tested using the phenotypic assay described earlier. The results were compared to those determined using the parent RTV-013522. We determined the pattern of phenotypic susceptibility to the NNRTIs, delavirdine, nevirapine and efavirenz, in the reverted vector RTV-013522/270I. The RTV-013522/270I displayed moderate reductions in nevirapine (14-fold) and efavirenz (8-fold) susceptibility and a significant reduction in delavirdine (40-fold) susceptibility compared to a wild type control RTV. The RTV-013522/270I showed no drug-dependent stimulation of viral replication in the presence of any of the NNRTI tested. In this patient sample the correlation of drug-dependent stimulation of viral replication with the mutation at I270S is very striking. A resistance test vector containing a single mutation at I270S (RTV-I270S) was constructed and tested in the phenotypic assay described earlier. The results were compared to those determined using a wild type control RTV. We determined the pattern of phenotypic susceptibility to the NNRTIs, delavirdine, nevirapine and efavirenz, in the RTV-V241S. The RTVI270S exhibited small reductions in susceptibility to nevirapine (15-fold), efavirenz (4-fold) and delavirdine (13-fold) compared to a wild type control RTV. The RTV-I270S showed drug-dependent stimulation of viral replication in the presence of nevirapine (~60%), delavirdine (~60%) and efavirenz (~40%).

EXAMPLE 13

Site Directed Mutagenesis Used to Confirm the Role of Specific Mutations in Phenotypic Susceptibility to Anti-Retroviral Drugs in HIV

V245E

A resistance test vector containing a single mutation, V245E, (RTV-V245E) was constructed and tested in the phenotypic assay described earlier. The results were compared to those determined using a genetically defined resistance test vector that was wild type at position 245. We determined the pattern of phenotypic susceptibility to the NNRTIs, delavirdine, nevirapine and efavirenz, in RTV-V245E. The RTV-V245E displayed no reductions in susceptibility to nevirapine, efavirenz or delavirdine compared to a wild type control RTV. The RTV-V245E showed no drug-dependent stimulation of viral replication in the presence of nevirapine, efavirenz, or delavirdine.

V245T

A resistance test vector containing a single mutation, V245T, (RTV-V245T) was constructed and tested in the phenotypic assay described earlier. The results were compared to those determined using a genetically defined resistance test vector that was wild type at position 245. We determined the pattern of phenotypic susceptibility to the NNRTIs, delavirdine, nevirapine and efavirenz, in RTV-V245E. The RTV-V245T displayed no reductions in susceptibility to nevirapine, efavirenz or delavirdine compared to a wild type control RTV. The RTV-V245T showed no drug-dependent stimulation of viral replication in the presence of nevirapine, efavirenz, or delavirdine.

I135T

A resistance test vector containing a single mutation, I135T, (RTV-I135T) was constructed and tested in the phenotypic assay described earlier. The results were compared to those determined using a genetically defined resistance test vector that was wild type at position 135. We determined the pattern of phenotypic susceptibility to the NNRTIs, delavirdine, nevirapine and efavirenz, in RTV-I135T. The RTV-I135T displayed no reductions in susceptibility to nevirapine, efavirenz or delavirdine compared to a wild type control RTV. The RTV-I135T showed no drug-dependent stimulation of viral replication in the presence of nevirapine, efavirenz, or delavirdine.

K103N

A resistance test vector containing a single mutation, K103N, (RTV-K103N) was constructed and tested in the phenotypic assay described earlier. The results were compared to those determined using a genetically defined resistance test vector that was wild type at positions 103. We determined the pattern of phenotypic susceptibility to the NNRTIs, delavirdine, nevirapine and efavirenz, in RTV-K103N. The RTV-K103N displayed reductions in susceptibility to nevirapine (67-fold), efavirenz (29-fold) and delavirdine (87-fold) compared to a wild type control RTV. The RTV-K103N exhibited no drug-dependent stimulation of viral replication in the presence of nevirapine, efavirenz, or delavirdine.

K103N+I135T

A resistance test vector containing two mutations, K103N and I135T (RTV-K103N/I135T) was constructed and tested in the phenotypic assay described earlier. The results were compared to those determined using a genetically defined resistance test vector that was wild type at position 103 and 135. We determined the pattern of phenotypic susceptibility to the NNRTIs, delavirdine, nevirapine and efavirenz, in RTV-K103N/I135T. The RTV-K103N/I135T displayed reductions in susceptibility to nevirapine (171-fold), efavirenz (80-fold) and delavirdine (121-fold) compared to a wild type control RTV. The RTVK103N/I135T exhibited no drug-dependent stimulation of viral replication in the presence of nevirapine, efavirenz, or delavirdine.

I135T+V245E

A resistance test vector containing two mutations, I135T and V245E (RTV-I135T/V245E) was constructed and tested in the phenotypic assay described earlier. The results were compared to those determined using a genetically defined resistance test vector that was wild type at positions 135 and 245. We determined the pattern of phenotypic susceptibility to the NNRTIs, delavirdine, nevirapine and efavirenz, in RTV-I135T/V245E. The RTV-I135T/V245E displayed minor reductions in susceptibility to nevirapine (2.5-fold), efavirenz (2-fold) and delavirdine (2-fold) compared to a wild type control RTV. The RTV-I135T/V245E exhibited no drug-dependent stimulation of viral replication in the presence of nevirapine, efavirenz, or delavirdine.

I135T +V245T

A resistance test vector containing two mutations, I135T and V245T (RTV-I135T/V245T) was constructed and tested in the phenotypic assay described earlier. The results were compared to those determined using a genetically defined resistance test vector that was wild type at positions 135 and 245. We determined the pattern of phenotypic susceptibility to the NNRTIs, delavirdine, nevirapine and efavirenz, in RTV-I135T/V245T. The RTV-I135T/V245T displayed minor reductions in susceptibility to nevirapine (4-fold), efavirenz (2.4-fold) and delavirdine (2.5-fold) compared to a wild type control RTV. The RTV-I135T/V245T exhibited no drug-dependent stimulation of viral replication in the presence of efavirenz and only minor stimulation of viral replication in the presence of nevirapine (~10%) or delavirdine (~10%).

K103N+I135T+V245E

A resistance test vector containing three mutations, K103N, I135T and V245E (RTV-K103N/I135T/V245E) was constructed and tested in the phenotypic assay described earlier. The results were compared to those determined using a genetically defined resistance test vector that was wild type at positions 103, 135 and 245. We determined the pattern of phenotypic susceptibility to the NNRTIs, delavirdine, nevirapine and efavirenz, in RTV-K103N. The RTV-K103N/I135T/V245E displayed reductions in susceptibility to nevirapine (244-fold), efavirenz (93-fold) and delavirdine (169-fold) compared to a wild type control RTV. The RTV-K103N/I135T/V245E showed no drug-dependent stimulation of viral replication in the presence of efavirenz but showed moderate levels of viral stimulation of replication in the presence of nevirapine (~15%) and delavirdine (~20%).

K103N+I135T+V245T

A resistance test vector containing three mutations, K103N, I135T and V245T (RTV-K103N/I135T/V245T) was constructed and tested in the phenotypic assay described earlier. The results were compared to those determined using a genetically defined resistance test vector that was wild type at positions 103, 135 and 245. We determined the pattern of phenotypic susceptibility to the NNRTIs, delavirdine, nevirapine and efavirenz, in RTV-K103N. The RTV-K103N/I135T/V245T displayed significant reductions in susceptibility to nevirapine (594-fold), efavirenz (174-fold) and delavirdine (>250-fold) compared to a wild type control RTV. The RTV-K103N/I135T/V245T showed drug-dependent stimulation of viral replication in the presence of efavirenz (~25%), nevirapine (~40%) and delavirdine (~50%).

EXAMPLE 14

Figure 14:
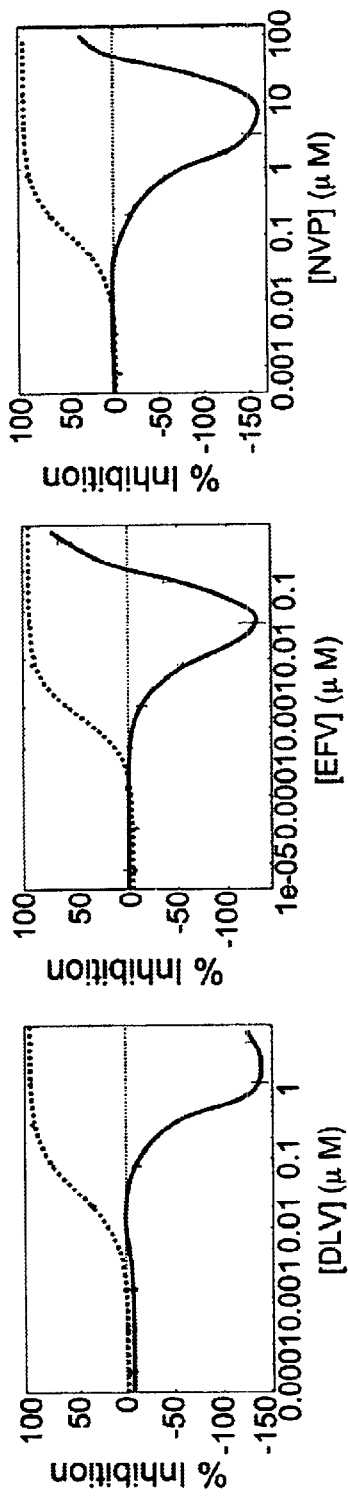
FIG. 14. Table of clinical history of twelve viral samples from Patient 1033, as described in Example 14. Data include: drug regimen, duration of drug regimen, viral load, phenotypic fold-change in susceptibility values relative to a drug sensitive virus control, such as PNL4-3, or HXB-2, and percent negative inhibition for those samples exhibiting drug-dependent stimulation of virus production.
Figure 15:
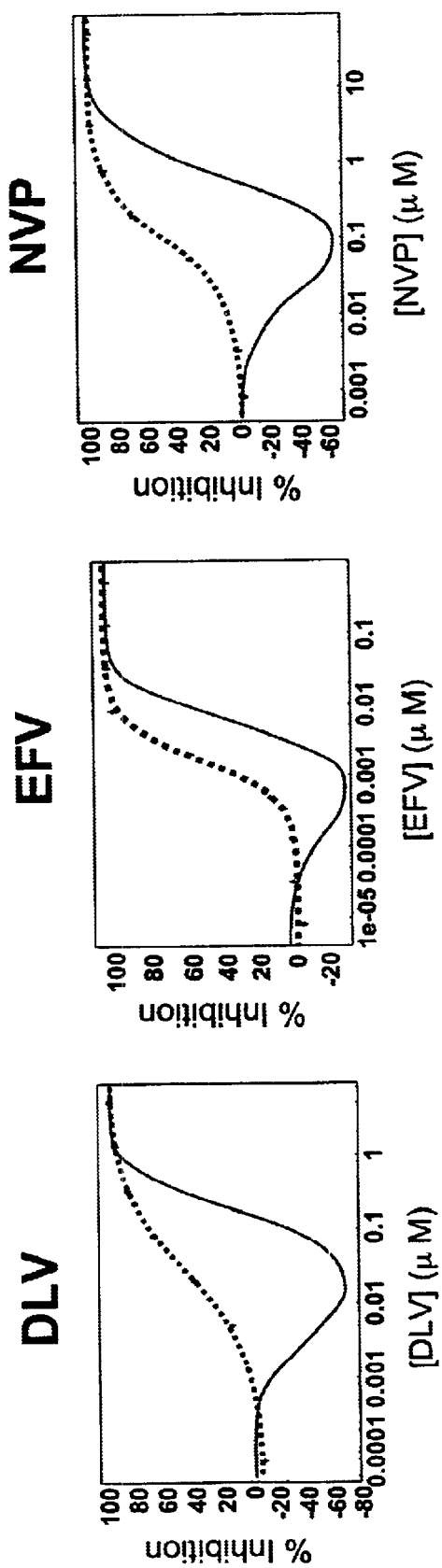
FIG. 15. Table of HIV-RT amino acid mutations for twelve viral samples from Patient 1033, as described in Example 14.
Figure 18A:
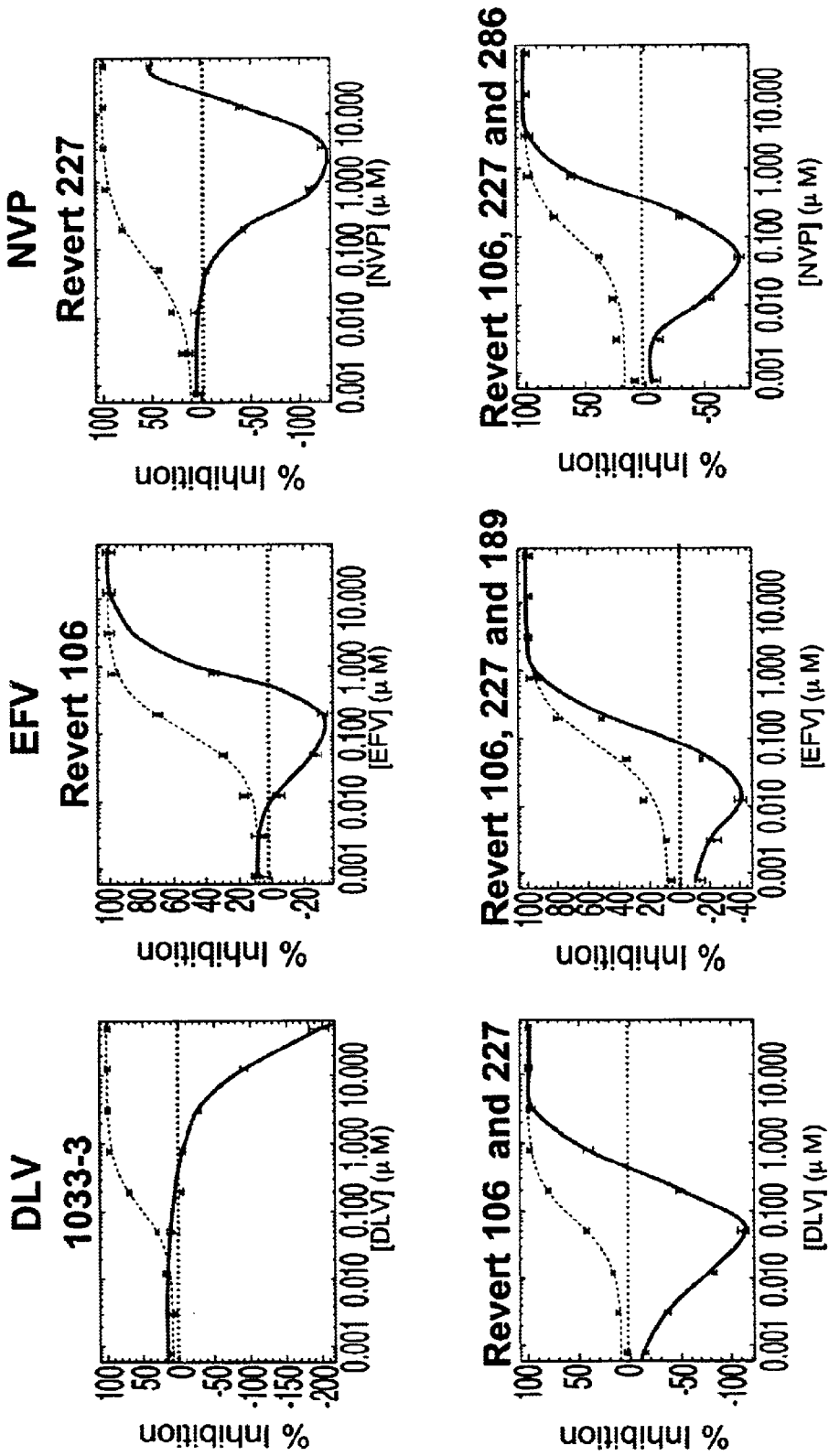
FIGS. 18A and 18B. Patient 014451, reduced susceptibility to an NNRTI drug dependent stimulation of viral replication associated with mutations at codon 101, codon 106 and codon 190 (Example 7).
Figure 18B:
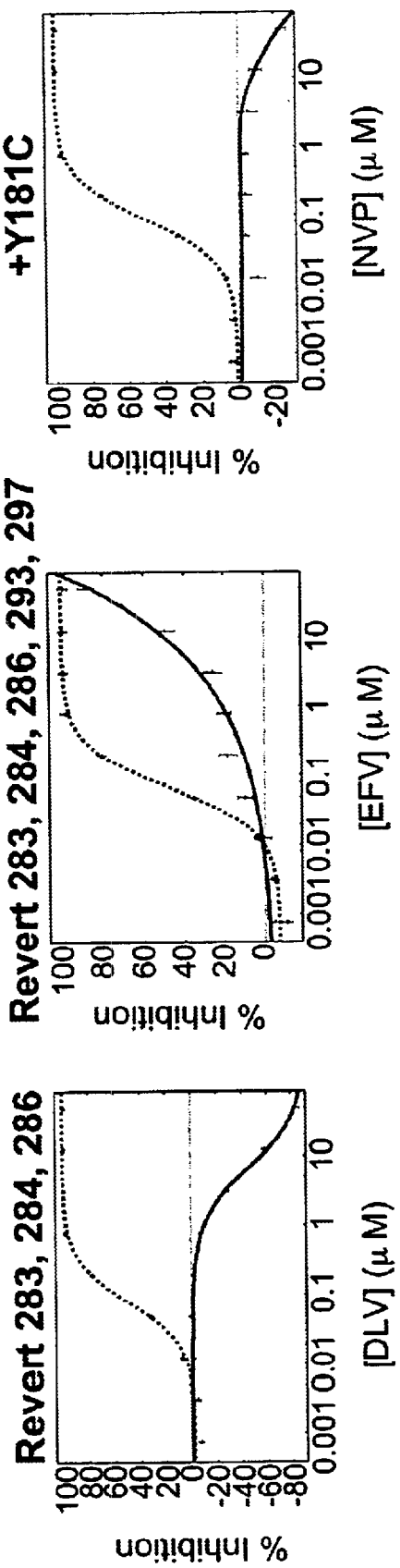
Figure 19:
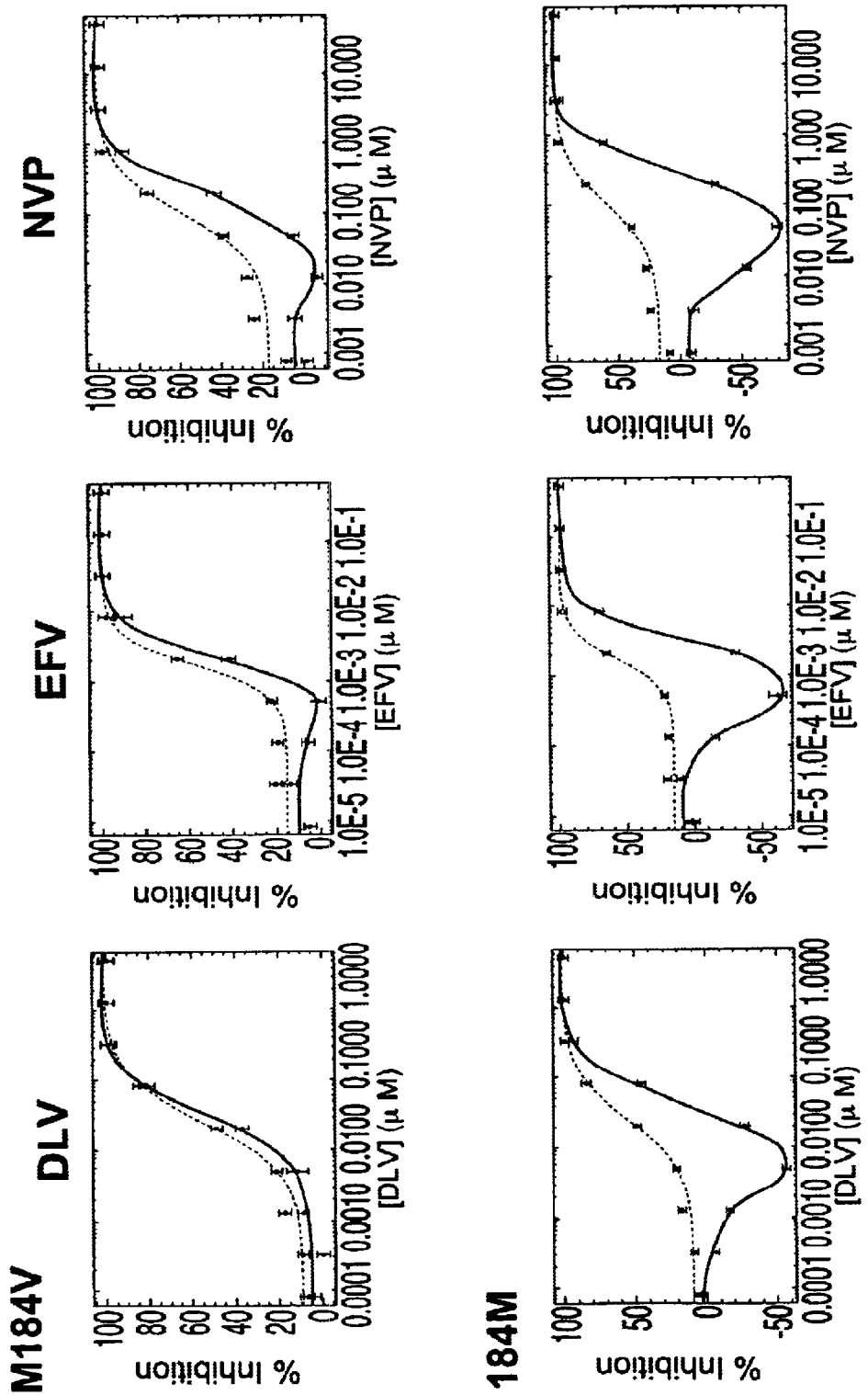
FIG. 19. Effect of M184V mutation on drug-dependent stimulation of viral replication: RTV-309

Using Resistance Test Vectors to Correlate Genotypes and Phenotypes Associated with NNRTI Drug Susceptibility And Resistance and Drug-Dependent Stimulation of Replication in HIV: Multiple Mutations Can Modulate Both Susceptibility and Stimulation Profiles Preparation of resistant test vectors and phenotypic analysis of patient 97–309 HIV samples Resistance test vectors were constructed as described in Example 1 from virus samples obtained from an individual patient at thirteen separate time points over a 2½-year period. This patient had been previously treated with two NRTIs (zidovudine and lamivudine) AZT, 3TC (NRTIS), and a PRI (indinavir) for a period of approximately 2 years at the time the first (97–309) and second (98–754) samples were obtained. The patient began taking a new anti-viral regimen including an NRTI (stavudine), an NNRTI (nevirapine), and two PRIs (nelfinavir and saquinavir) at the time the third sample (98–1032) was obtained. Additional samples were obtained 4, 5 and 10 weeks later (00-2-011658, 00-2-011659 and 98–1033, respectively). The patient then stopped taking nevirapine, and additional samples were obtained after 12, 16, 24 and 36 weeks (99-2-008973, 98-757, 99-2-8980 and 98-1080, respectively). The patient then switched therapy again to zidovudine, lamivudine and indinavir, and additional samples were obtained after 5 months (AA1264) and 10 months (99-2-006174). Viral load measurements, patient therapy, and dates of draw are shown in FIG. 14. Following initiation of d4T, nevirapine, nelfinavir and saquinavir, the patient experienced a transient reduction in viral load followed by a return to baseline viral load (~1,200,000 copies/ml). Removal of nevirapine from the regimen led to a reduction in viral load to <300,000 copies/ml (a 4-fold reduction). Isolation of viral RNA and RT/PCR was used to generate patient derived segments that comprised viral sequences coding for all of PR and aa 1–313 of RT from all twelve samples. The PDS were inserted into an indicator gene viral vector to generate resistance test vectors designated RTV-309, RTV-754, RTV-1032, RTV-011658, RTV-011659, RTV-1033, RTV-008973, RTV-757, RTV-008980, RTV1080, RTV1264 and RTV-006174. These RTVs were tested in a phenotypic assay to determine accurately and quantitatively the level of susceptibility to a panel of anti-retroviral drugs. This panel of anti-retroviral drugs comprised members of the classes known as NRTIs zidovudine, lamivudine, stavudine, didanosine, zalcitabine, and abacavir) NNRTIs (delavirdine, efavirenz and nevirapine), and PRIs (amprenavir, indinavir, nelfinavir, ritonavir, and saquinavir). An IC50 was determined for each resistance test vector pool for each drug tested. The pattern of susceptibility to all of the drugs tested was examined and compared to known patterns of susceptibility. A pattern of susceptibility to the NNRTIs was observed for patient RTV-1033, RTV-008973, RTV-757, RTV-008980 and RTV-1080 in which there were reductions in nevirapine (>600-fold), delavirdine (from 3 to 18-fold) and efavirenz (from 16 to 300-fold) susceptibility. Furthermore, RTV-1033, RTV-008973, RTV-757, RTV-008980 and RTV-1080 showed drug-dependent stimulation of viral replication in response to nevirapine (40 to 250%), delavirdine (20 to 180%) and efavirenz (30 to 170%). The actual fold change in susceptibility and the percent stimulation of viral replication for each RTV is shown in FIG. 14a.

Determination of genotype of patient HIV samples

RTV-309, RTV-754, RTV-1032, RTV-011658, RTV-011659, RTV-1033, RTV-008973, RTV-757, RTV-008980, RTV1080, RTV1264 and RTV-006174 DNA were analyzed by ABI chain terminator automated sequencing. The nucleotide sequence was compared to the consensus sequence of a wild type clade B HIV-1 (HIV Sequence Database Los Alamos, N. Mex.). The genotype was examined for sequences that are different from the control sequence. Mutations were observed at the positions listed in FIG. 14b.

Site directed mutagenesis is used to confirm the role of specific mutations in phenotypic susceptibility to antiretroviral drugs in HIV RTV-1033 displayed the most dramatic drug-dependent stimulation of viral replication of all of the samples tested from this patient. A single clone (RTV-1033-3) was obtained from the patient-derived RTV pool that had mutations and phenotypic patterns of NNRTI susceptibility and drug-dependent stimulation of viral replication characteristic of the RTV-1033 pool. The RTV-1033-3 had the following mutations present in the revere transcriptase: V35I, D67N, T69D, K70R, V106A, D123G, V189L, T200A, I202T, H208Y, R211K, T215F, D218E, K219Q, H221Y, L228H, L283I, R284K, T286A, V293I and E297K. RTV-1033-3 showed dramatic reductions in susceptibility to delavirdine (27-fold), efavirenz (>450-fold) and nevirapine (>600-fold) and dramatic drug-dependent stimulation of viral replication in the presence of delavirdine (190%), efavirenz (180%) and nevirapine (200%).

V106A

A resistance test vector containing all of the mutations present in RTV-1033-3 except for V106A (RTV-1033-3/106V) was constructed and tested using the phenotypic assay described earlier. The results were compared to those determined using the parent RTV-1033-3. We determined the pattern of phenotypic susceptibility to the NNRTIs, delavirdine, nevirapine and efavirenz, in the reverted vector, RTV-1033-3/106V. The RTV-1033-3/106V displayed a moderate reduction in nevirapine (9-fold) susceptibility, no reduction in efavirenz susceptibility and a significant increase in delavirdine (20-fold) susceptibility (hyper-susceptibility) compared to a wild type control RTV. The RTV-1033-3/106V showed no drug-dependent stimulation of viral replication in the presence of delavirdine but showed low levels of drug-dependent stimulation of viral replication in the presence of efavirenz (~20%) and nevirapine (~40%).

F227L

A resistance test vector containing all of the mutations present in RTV-1033-3 except for F227L (RTV-1033-3/227F) was constructed and tested using the phenotypic assay described earlier. The results were compared to those determined using the parent RTV-1033-3. We determined the pattern of phenotypic susceptibility to the NNRTIs, delavirdine, nevirapine and efavirenz, in the reverted vector, RTV-1033-3/227F. The RTV-1033-3/227F displayed significant reductions in nevirapine (>600-fold), efavirenz (18-fold) and delavirdine (72-fold) susceptibility compared to a wild type control RTV. The RTV-1033-3/227F showed drug-dependent stimulation of viral replication in the presence of delavirdine (~100%), efavirenz (~100%) and nevirapine (~120%).

V106A and F227L

A resistance test vector containing all of the mutations present in RTV-1033-3 except for V106A and F227L (RTV-1033-3/106V/227F) was constructed and tested using the phenotypic assay described earlier. The results were compared to those determined using the parent RTV-1033-3. We determined the pattern of phenotypic susceptibility to the NNRTIs, delavirdine, nevirapine and efavirenz, in the reverted vector, RTV-1033-3/106V/227F. The RTV-1033-3/106V/227F displayed moderate reductions in nevirapine (13-fold), efavirenz (6-fold) and delavirdine (6-fold) susceptibility compared to a wild type control RTV. The RTV-1033-3/106V/227F showed drug-dependent stimulation of viral replication in the presence of delavirdine (~80%), efavirenz (~80%) and nevirapine (~110%).

V106A, V189L and F227L

A resistance test vector containing all of the mutations present in RTV-1033-3 except for V106A, V189L and F227L (RTV-1033-3/106V/189V/227F) was constructed and tested using the phenotypic assay described earlier. The results were compared to those determined using the parent RTV-1033-3. We determined the pattern of phenotypic susceptibility to the NNRTIs, delavirdine, nevirapine and efavirenz, in the reverted vector, RTV-1033-3/106V/189V/227F. The RTV-1033-3/106V/189V/227F displayed small reductions in nevirapine (2.8-fold), efavirenz (2-fold) and delavirdine (2.7-fold) susceptibility compared to a wild type control RTV. The RTV-1033-3/106V/189V/227F showed drug-dependent stimulation of viral replication in the presence of delavirdine (~35%), efavirenz (~30%) and nevirapine (~40%).

V106A, F227L and T286A

A resistance test vector containing all of the mutations present in RTV-1033-3 except for V106A, F227L and T286A (RTV-1033-3/106V/227F/286T) was constructed and tested using the phenotypic assay described earlier. The results were compared to those determined using the parent RTV-1033-3. We determined the pattern of phenotypic susceptibility to the NNRTIs, delavirdine, nevirapine and efavirenz, in the reverted vector, RTV-1033-3/106V/227F/286T. The RTV-1033-3/106V/227F/286T displayed moderate reductions in nevirapine (6-fold), efavirenz (5-fold) and delavirdine (3-fold) susceptibility compared to a wild type control RTV. The RTV-1033-3/106V/227F/286T showed drug-dependent stimulation of viral replication in the presence of delavirdine (~60%), efavirenz (~50%) and nevirapine (~70%)

L283I, R284K and T286A

A resistance test vector containing all of the mutations present in RTV-1033-3 except for L283I, R284K and T286A (RTV-1033-3/283L/284R/286T) was constructed and tested using the phenotypic assay described earlier. The results were compared to those determined using the parent RTV-1033-3. We determined the pattern of phenotypic susceptibility to the NNRTIs, delavirdine, nevirapine and efavirenz, in the reverted vector, RTV-1033-3/283L/284R/286T. The RTV-1033-3/283L/284R/286T displayed significant reductions in nevirapine (>600-fold), efavirenz (85-fold) and delavirdine (7-fold) susceptibility compared to a wild type control RTV. The RTV-1033-3/283L/284R/286T showed drug-dependent stimulation of viral replication in the presence of delavirdine (~40%), efavirenz (~30%) and nevirapine (~80%).

L283I. R284K. T286A, V293I and E297K

A resistance test vector containing all of the mutations present in RTV-1033-3 except for L283I, R284K, T286A, V293I and E297K (RTV-1033-3/283L/284R/286T/293V/297E) was constructed and tested using the phenotypic assay described earlier. The results were compared to those determined using the parent RTV-1033-3. We determined the pattern of phenotypic susceptibility to the NNRTIs, delavirdine, nevirapine and efavirenz, in the reverted vector, RTV-1033-3/283L/284R/286T/293V/297E. The RTV-1033-3/283L/284R/286T/293V/297E displayed significant reductions in nevirapine (144-fold), efavirenz (5-fold) and delavirdine (16-fold) susceptibility compared to a wild type control RTV. The RTV-1033-3/283L/284R/286T/293V/297E showed no drug-dependent stimulation of viral replication in the presence of delavirdine, efavirenz or nevirapine.

Y181C

A resistance test vector containing all of the mutations present in RTV-1033-3, in addition to Y181C (RTV-1033-3/181C) was constructed and tested using the phenotypic assay described earlier. The results were compared to those determined using the parent RTV-1033-3. We determined the pattern of phenotypic susceptibility to the NNRTIs, delavirdine, nevirapine and efavirenz, in the mutated vector, RTV-1033-3/181C. The RTV-1033-3/181C displayed a significant reduction in nevirapine (>600-fold), efavirenz (>450-fold) and delavirdine (>250-fold) susceptibility compared to a wild type control RTV. The RTV-1033-3/181C showed no drug-dependent stimulation of viral replication in the presence of nevirapine but showed drug-dependent stimulation of viral replication in the presence of efavirenz (~100%) and nevirapine (~100%).

M184V

A resistance test vector containing all of the mutations present in RTV-1033-3 in addition to M184V (RTV-1033-3/184V) was constructed and tested using the phenotypic assay described earlier. The results were compared to those determined using the parent RTV-1033-3. We determined the pattern of phenotypic susceptibility to the NNRTIs, delavirdine, nevirapine and efavirenz, in the mutated vector, RTV-1033-3/184V. The RTV-1033-3/184V displayed a significant reduction in nevirapine (>600-fold), efavirenz (28-fold) and a moderate reduction in delavirdine (5-fold) susceptibility compared to a wild type control RTV. The RTV-1033-3/184V showed drug-dependent stimulation of viral replication in the presence of delavirdine (~100%), efavirenz (~80%) and nevirapine (~100%).

Clone 309-1

RTV-309 was derived from a virus sample from patient 1033 before the patient had received any NNRTI inhibitors. RTV-309 exhibited a wild type pattern of susceptibility to delavirdine and efavirenz and a small reduction in susceptibility to nevirapine (3-fold) and no drug-dependent stimulation of viral replication in the presence of NNRTIs. A single clone (RTV-309-3) was obtained from the patient-derived RTV pool that had mutations and phenotypic patterns of NNRTI susceptibility and drug-dependent stimulation of viral replication characteristic of the RTV-1033 pool. The RTV-309-3 had the following mutations present in the revere transcriptase: V35I, D67N, T69D, K70R, L109I, M184V, V189L, T200A, I202T, H208Y, R211K, T215F, D218E, K219Q, H221Y, L228H, L283I, R284K, T286A and E297K. RTV-309-3 exhibited a wild type pattern of susceptibility to delavirdine and efavirenz and a small reduction in susceptibility to nevirapine (3-fold) and no drug-dependent stimulation of viral replication in the presence of NNRTIs.

M184V

A resistance test vector containing all of the mutations present in RTV-309-3 except for the M184V (RTV-309-3/184M) was constructed and tested using the phenotypic assay described earlier. The results were compared to those determined using the parent RTV-309-3. We determined the pattern of phenotypic susceptibility to the NNRTIs, delavirdine, nevirapine and efavirenz, in the reverted vector, RTV-309-3/184M. The RTV-309-3/184M displayed a moderate reduction in delavirdine (4-fold), efavirenz (5-fold) and nevirapine (9-fold) susceptibility compared to a wild type control RTV. The RTV-309-3/184M showed drug-dependent stimulation of viral replication in the presence of delavirdine (~50%), efavirenz (~60%) and nevirapine (~80%).

The invention further relates to novel vectors, host cells and compositions for isolation and identification of the non-nucleoside HIV-1 reverse transcriptase inhibitor resistance mutant and using such vectors, host cells and compositions to carry out anti-viral drug screening. This invention also relates to the screening of candidate drugs for their capacity to inhibit/stimulate said mutant.

What is claimed is:

1. A method of assessing the effectiveness of a non nucleoside reverse transcriptase inhibitor ("NNRTI") on an HIV-infected patient comprising detecting, in a biological sample of the HIV-infected patient, the presence of a mutation at codon 230 of the nucleic acid encoding HIV reverse transcriptase, wherein the presence of such a mutation correlates with a decrease in NNRTI susceptibility or with a drug-dependant stimulation of viral replication.

2. The method of claim 1, wherein the presence of such a mutation correlates with a decrease in NNRTI susceptibility and drug-dependant stimulation of viral replication.

3. The method of claim 1, wherein the mutated codon 230 encodes a leucine (L).

4. The method of claim 1, further comprising evaluating whether the biological sample of the HIV-infected patient comprises nucleic acid encoding HIV reverse transcriptase having a mutation at at least one of codon 101, codon 103, codon 181, codon 190, codon 221 or codon 238, wherein the presence of such a mutation correlates with a decrease in NNRTI susceptibility.

5. The method of claim 2, further comprising evaluating whether the biological sample of the HIV-infected patient rises nucleic acid encoding HIV reverse transcriptase having a mutation at at least one of codon 101, codon 103 or codon 190, wherein the presence of a mutation at codon 230 and a mutation at codon 101, codon 103 or codon 190 correlates with a decrease in NNRTI susceptibility and drug-dependant stimulation of viral replication.

6. The method of claim 1, wherein the mutated codon 101 encodes a glutamic acid (E), the mutated codon 103 encodes an asparagine (N), the mutated codon 181 encodes a cysteine (C), the mutated codon 190 encodes a serine (S), the mutated codon 221 encodes a tyrosine (Y), or the mutated codon 238 encodes a threonine (T).

7. The method of claim 1, wherein the HIV-infected patient is being treated with an antiretroviral agent.

8. The method of claim 1, wherein the presence of said mutation is detected by determining a nucleic acid sequence encoding said mutation.

9. The method of claim 1, wherein the HIV-infected patient is undergoing or has undergone prior treatment with an NNRTI or other antiretroviral agent.

10. The method of claim 9, wherein the HIV-infected patient is undergoing or has undergone NNRTI therapy and the presence of a mutation at codon 230 is determined relative to reverse transcriptase codon 230 present in the HIV-infected patient prior to NNRTI therapy.

11. The method of claim 1, wherein the NNRTI is delavirdine, efavirenz or nevirapine.

12. The method of claim 2, wherein the NNRTI is delavirdine, efavirenz or nevirapine.

* * * * *

UNITED STATES PATENT AND TRADEMARK OFFICE
CERTIFICATE OF CORRECTION

PATENT NO. : 6,653,081 B1
DATED : November 25, 2003
INVENTOR(S) : Jeannette Whitcomb It is certified that error appears in the above-identified patent and that said Letters Patent is hereby corrected as shown below:

<u>Title page,</u>
Item [54], Title, should read:
-- METHODS FOR MONITORING ANTIRETROVIRAL THERAPY AND GUIDING THERAPEUTIC DECISIONS IN THE TREATMENT OF HIV/AIDS --.

Signed and Sealed this

Third Day of February, 2004

JON W. DUDAS
*Acting Director of the United States Patent and Trademark Office*